(12) United States Patent
Rodley

(10) Patent No.: US 11,566,346 B2
(45) Date of Patent: Jan. 31, 2023

(54) PROTEIN SCAFFOLD

(71) Applicant: Philip David Rodley, Tokyo (JP)

(72) Inventor: Philip David Rodley, Tokyo (JP)

( * ) Notice: Subject to any disclaimer, the term of this patent is extended or adjusted under 35 U.S.C. 154(b) by 271 days.

(21) Appl. No.: 16/911,398

(22) Filed: Jun. 25, 2020

(65) Prior Publication Data

US 2021/0403900 A1    Dec. 30, 2021

(51) Int. Cl.
*C40B 40/10* (2006.01)
*C12N 15/10* (2006.01)

(52) U.S. Cl.
CPC .......... *C40B 40/10* (2013.01); *C12N 15/1037* (2013.01); *C12N 15/1044* (2013.01)

(58) Field of Classification Search
None
See application file for complete search history.

(56) References Cited

U.S. PATENT DOCUMENTS

| 2007/0281006 | A1 | 12/2007 | Nicolau et al. |
| 2016/0090400 | A1 | 3/2016 | Longo et al. |
| 2017/0088602 | A1 | 3/2017 | Cload et al. |

FOREIGN PATENT DOCUMENTS

WO    WO 2009/058379 A2 *   5/2009   ............. C40B 40/10

* cited by examiner

*Primary Examiner* — Christian C Boesen

(57) ABSTRACT

The invention provides a protein scaffold and methods of preparing, screening, engineering and using the protein scaffold.

7 Claims, 27 Drawing Sheets

Specification includes a Sequence Listing.

Fig. 2
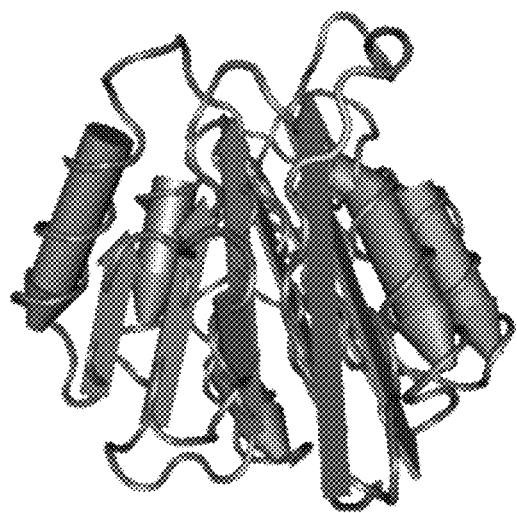 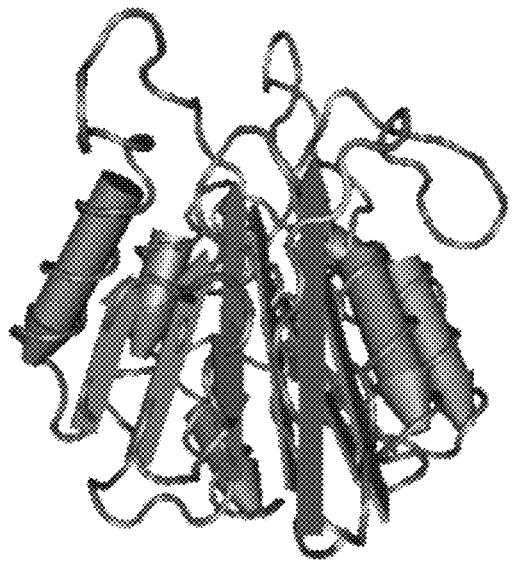
A
(SEQ ID NO: 80)
B
(SEQ ID NO: 11)

Fig. 4

```
1   GSHMVSGKIVVIGSSTGGPRSLDMIIPNLPKNFPAPIVVVQHMPPGFTKSLAQRLDSTSE     60
          β1       α1        β2         α2

61  LTVKEAEDGEEVKPGFVYIAPGDFHLGLKAQNGKVFFFLDKSDKINNVRPAVDPTLDKAAEIY  123
       β3         β4      β5      β6              α3

124 KEKTIAVILTGMGKDGTKGAFKVKFYGGTVIAEDKETSVVFGMPKSVIEEGYADYVL        180
       β7         α4       β8  3₁₀    α5       β9

181 PAYKIPEKLIELV 193
         α6
```

Fig. 5

```
  1 GSHMVSGKIVVIGSSTGGPRSLDMIIPNLPKNFPAPIVVVQHMPPGFTKSLAQRLDSTSE  60
 61 LTVKEAEDGEEVKPGFVYIAPGDFHLGLKAQNGKVFFFLDKSDKINNVRPAVDFTLDKAA 120
121 EIYKEKTIAVILTGMGKDGTKGAFKVKFYGGTVIAEDKETSVVFGMPKSVIEEGYADYVL 180
181 PAYKIPEKLIELV                                                193
```

Fig. 6

```
GSHMVSGKIVVIGSSTGGPRSLDMIIPNLPKNFPAPIVVVQHMP------PGFTKSLAQR      54  SEQ ID NO: 1
GSHMVSGKIVVIGSSTGGPRSLDMIIPNLPKNFPAPIVVVQHGGLDNGSYTGGTKSLAQR      60  SEQ ID NO: 10
GSHMVSGKIVVIGSSTGGPRSLDMIIPNLPKNFPAPIVVVQHMP------PGFTKSLAQR      54  SEQ ID NO: 8
GSHMVSGKIVVIGSSTGGPRSLDMIIPNLPKNFPAPIVVVQHGGLDNGSYTGGTKSLAQR      60  SEQ ID NO: 9
GSHMVSGKIVVIGSSTGGPRSLDMIIPNLPKNFPAPIVVVQHGGLDNGSYTGGTKSLAQR      60  SEQ ID NO: 11
                                        1

LDSTSELTVKEAEDGEEVKPGFVYIAPGDFHLGLKAQNGKVFFFLDKSDK------INNV     108  SEQ ID NO: 1
LDSTSELTVKEAEDGEEVKPGFVYIAPGDFHLGLKAQNGKVFFFLDKSDK------INNV     114  SEQ ID NO: 10
LDSTSELTVKEAEDGEEVKPGFVYIAPGDFHLGLKAQNGKVFFFLDKSGGDRNGYSAGGV     114  SEQ ID NO: 8
LDSTSELTVKEAEDGEEVKPGFVYIAPGDFHLGLKAQNGKVFFFLDKSGGDRNGYSAGGV     120  SEQ ID NO: 9
LDSTSELTVKEAEDGEEVKPGFVYIAPGDFHLGLKAQNGKVFFFLDKSGGDRNGYSAGGV     120  SEQ ID NO: 11
                                             2

RPAVDFTLDKAAEIYKEKTIAVILTG--------MGKDGTKGAFKVKFYGGTVIAEDKETS    161  SEQ ID NO: 1
RPAVDFTLDKAAEIYKEKTIAVILTGGLVDGREAGGDGTKGAFKVKFYGGTVIAEDKETS    174  SEQ ID NO: 10
RPAVDFTLDKAAEIYKEKTIAVILTGGLVDGREAGGDGTKGAFKVKFYGGTVIAEDKETS    174  SEQ ID NO: 8
RPAVDFTLDKAAEIYKEKTIAVILTG--------MGKDGTKGAFKVKFYGGTVIAEDKETS    173  SEQ ID NO: 9
RPAVDFTLDKAAEIYKEKTIAVILTGGLVDGREAGGDGTKGAFKVKFYGGTVIAEDKETS    180  SEQ ID NO: 11
                         3

VVFGMPKSVIEEGYADYVLPAYKIPEKLIELV   193  SEQ ID NO: 1
VVFGMPKSVIEEGYADYVLPAYKIPEKLIELV   206  SEQ ID NO: 10
VVFGMPKSVIEEGYADYVLPAYKIPEKLIELV   206  SEQ ID NO: 8
VVFGMPKSVIEEGYADYVLPAYKIPEKLIELV   205  SEQ ID NO: 9
VVFGMPKSVIEEGYADYVLPAYKIPEKLIELV   212  SEQ ID NO: 11
```

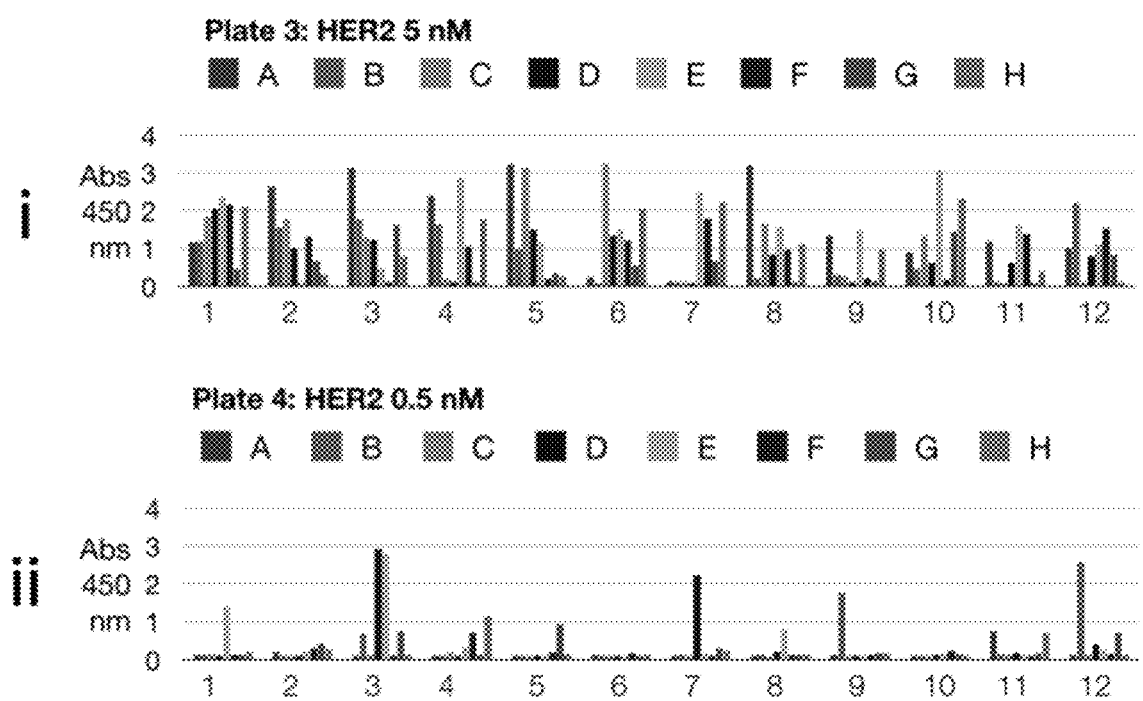

Fig. 18

```
>chemotaxis protein CheY [Fervidobacterium pennivorans]
Sequence ID: ANE42371.1 Length: 337
Range 1: 147 to 337

Score:308 bits(788), Expect:7e-107,
Method:Compositional matrix adjust.,
Identities:149/191(78%), Positives:173/191(90%), Gaps:1/191(0%)

Query   4    MVSGKIVVIGSSTGPRSLDMIIPNLPKNFPAPIVVVQHMPPGFTKSLAQRLDSTSELTV   63
             +VSGK+VVIGSSTGGPRSLD++IP LPK+FPAPI++VQHMPPGFTKSLAQRLD  S L+V
Sbjct 147    IVSGKVVVIGSSTGGPRSLDLVIPPLPKDFPAPILLVQHMPPGFTKSLAQRLDRISNLSV  206

Query  64    KEAEDGEEVKPGFVYIAPGDFHLGLKAQNGKVFFFLDK-SDKINNVRPAVDFTLDKAAEI  122
             KEAE+G+ +KPG+VY+APGD+H+G+K Q+ K   +LDK  +KINN RPAVD+TLDK AEI
Sbjct 207    KEAEEGDVLKPGWVYVAPGDYHMGIKYQDKKGIIYLDKNTEKINNVRPAVDYTLDKVAEI  266

Query 123    YKEKTIAVILTGMGKDGTKGAFKVKFYGGTVIAEDKETSVVFGMPKSVIEEGYADYVLPA  182
             YKE TIAVILTGMGK GTKGAFKVKF+ G VIAE +ET VVFGMPKSVIEEGYADYVLPA
Sbjct 267    YKENTIAVILTGMGKDGTKGAFKVKFFKGVVIAESQETCVVFGMPKSVIEEGYADYVLPA  326

Query 183    YKIPEKLIELV  193
             KIPEKL+ELV
Sbjct 327    DKIPEKLVELV  337
```

```
  1 IVSGKVVVIGSSTGGPRSLDLVIPPLPKDFPAPILLVQHMPPGFTKSLAQRL   52
 53 DRISNLSVKEAEEGDVLKPGWVYVAPGDYHMGIKYQDKKGIIYLDKNTEKIN  104
105 NVRPAVDYTLDKVAEIYKENTIAVILTGMGKDGTKGAFKVKFFKGVVIAESQ  156
157 ETCVVFGMPKSVIEEGYADYVLPADKIPEKLVELV                  191
```

B

```
  1 IVSGKVVVIGSSTGGPRSLDLVIPPLPKDFPAPILLVQHGGLDNGSYTGGT   51
 52 KSLAQRLDRISNLSVKEAEEGDVLKPGWVYVAPGDYHMGIKYQDKKGIIYL  102
103 DKSGGDRNGYSAGGVRPAVDYTLDKVAEIYKENTIAVILTGGLVDGREAGG  153
154 DGTKGAFKVKFFKGVVIAESQETSVVFGMPKSVIEEGYADYVLPADKIPEK  204
205 LVELV                                               209
```

Fig. 20

```
>chemotaxis protein CheY [Fervidobacterium pennivorans]
Sequence ID: ANE42371.1 Length: 337
Range 1: 147 to 337

Score:334 bits(857), Expect:2e-112,
Method:Compositional matrix adjust.,
Identities:178/209(85%), Positives:178/209(85%), Gaps:18/209(8%)

Query   1    IVSGKVVVIGSSTGGPRSLDLVIPPLPKDFPAPILLVQHGGLDNGSYTGGTKSLAQRLDR    60
             IVSGKVVVIGSSTGGPRSLDLVIPPLPKDFPAPILLVQH       G TKSLAQRLDR
Sbjct   147  IVSGKVVVIGSSTGGPRSLDLVIPPLPKDFPAPILLVQHMP-------PGFTKSLAQRLDR  200

Query   61   ISNLSVKEAEEGDVLKPGWVYVAPGDYHMGIKYQDKKGIIYLDKSGGDRNGYSAGGVRPA   120
             ISNLSVKEAEEGDVLKPGWVYVAPGDYHMGIKYQDKKGIIYLDK    N     VRPA
Sbjct   201  ISNLSVKEAEEGDVLKPGWVYVAPGDYHMGIKYQDKKGIIYLDK------NTEKINNVRPA  255

Query   121  VDYTLDKVAEIYKENTIAVILTGGLVDGREAGGDGTKGAFKVKFFKGVVIAESQETSVVF   180
             VDYTLDKVAEIYKENTIAVILTG       G DGTKGAFKVKFFKGVVIAESQET VVF
Sbjct   256  VDYTLDKVAEIYKENTIAVILTG--------MGKDGTKGAFKVKFFKGVVIAESQETCVVF  308

Query   181  GMPKSVIEEGYADYVLPADKIPEKLVELV                                 209
             GMPKSVIEEGYADYVLPADKIPEKLVELV
Sbjct   309  GMPKSVIEEGYADYVLPADKIPEKLVELV                                 337
```

PROTEIN SCAFFOLD

CROSS-REFERENCE TO RELATED APPLICATIONS

N/A

STATEMENT REGARDING FEDERALLY SPONSORED RESEARCH OR DEVELOPMENT

N/A

NAMES OF THE PARTIES TO A JOINT RESEARCH AGREEMENT

N/A

REFERENCE TO THE SEQUENCE LISTING

This application incorporates by reference a Sequence Listing submitted Jul. 8, 2020 as a text file entitled "Seqlisting.txt" created on Jul. 8, 2020 and having a size of 100 kilobytes.

STATEMENT REGARDING PRIOR DISCLOSURES BY THE INVENTOR OR JOINT INVENTOR

N/A

FIELD OF THE INVENTION

The invention provides a protein scaffold and methods of preparing, screening, engineering and using the protein scaffold.

BACKGROUND OF THE INVENTION

This invention relates to a protein scaffold useful, for example, for the generation of products having novel binding characteristics.

Interactions between molecules such as proteins and ligands are essential to multiple functions in organisms. The ability to obtain protein molecules with binding properties to a target of interest is of importance in biological sciences and medicine.

For example, the ability to diagnose disease can be facilitated by the ability to detect the presence of a target of interest associated with the diseased state. In another example, modulation of interactions between molecules within the body are known to have therapeutic effects and many drugs are developed by making use of molecules which bind to ligands, receptors, enzymes and other targets of therapeutic interest. Antibodies, by virtue of their relatively large and complex binding surfaces are known to generally have higher specificity for their targets than small molecule drugs, and in therapeutic applications they have been known to have a lower probability of inducing toxicity from indiscriminate binding. However it is known that the use of antibodies sometimes suffers from disadvantages, such as the typical need for mammalian cell production to obtain full length antibodies for therapeutic use, and the generally lower tissue penetration of full length antibodies compared to smaller molecules.

Although the use of antibody fragments can overcome some of these disadvantages, antibody fragments have a tendency to aggregate and be less stable than full-length antibodies. For example, because of instability issues of scFv molecules, for some applications time consuming stability maturation is sometimes necessary (Honegger A. et al., 2009), and lack of thermal stability can sometimes render scFv molecules useless in vivo (Willuda J. et al., 1999). In some situations, the instability of scFv can be an impediment to their use in engineering bispecific and multispecific constructs (Miller B. et al., 2010, Xu L. et al., 2013). This has generated an interest in engineering non-immunoglobulin protein molecules to overcome some of these disadvantages.

There have been efforts to develop non-immunoglobulin protein molecules by randomizing protein surfaces to generate libraries of novel binding proteins (for example, Binz H. et al., 2003, Vogt M., Skerra A., 2004). However, in some cases, engineering difficulties encountered during randomization can result in scaffold library members with stabilities only marginally better than those of antibody fragments. It is also generally thought that differences in the structure of individual scaffold proteins and the topography of the scaffold binding surfaces results in bias in the types of epitopes that each scaffold efficiently recognizes (Gilbreth R., Koide S., 2012). For example, the rigid and concave binding surface of DARPins is thought to limit the structural diversity of epitopes that are able to be recognized by this scaffold. (Schilling J. et al., 2014, Gilbreth R., Koide S., 2012). In a related example, the LoopDARPin scaffold replaces the concave binding surface of the DARPin by one with a protrusion in the middle, and is expected to bind to different shaped epitopes than DARPins (Schilling J. et al., 2014). In other examples, the basket like structure of the anticalin scaffold tends to cradle the bound target, and affibodies have a flat binding site architecture which tends to recognize similarly flat surfaces in their targets (Gilbreth R., Koide S., 2012). The topography of a scaffold binding surface is generally correlated with the types of epitopes that are recognized with high affinity.

Thus, there is a need to develop small, stable, artificial antibody-like molecules for a variety of therapeutic, diagnostic and industrial applications.

Citation or discussion of a reference herein shall not be construed as an admission that such is prior art to the present invention.

SUMMARY OF THE INVENTION

The present invention provides a recombinant, non-naturally occurring protein scaffold which can be used to obtain binding activity to a compound of interest. In particular, the scaffold described herein may be used to display defined loops which are analogous to the complimentary determining regions ("CDRs") of an antibody variable region. These loops may be subjected to randomization or restricted evolution to generate diversity required to bind a variety of target compounds. The invention provides a recombinant, non-naturally occurring polypeptide scaffold comprising a recombinant $CheB_c$ domain, comprising a plurality of alpha helices and beta strands and a $3_{10}$ helix linked by a plurality of loop regions (a modified doubly-wound a/P sandwich fold) wherein at least one loop regions is a non-naturally occurring variant of the cognate loop region.

In a specific embodiment, the recombinant scaffold protein (herein after known as the "scaffold of the invention") comprises a recombinant $CheB_c$ domain having at least 50%, at least 60%, at least 70%, at least 75%, at least 80%, at least 90%, at least 95%, or at least 99% amino acid sequence identity outside the loop regions to SEQ ID NO: 1, and wherein at least one loop regions is a non-naturally occurring variant of the cognate loop region of SEQ ID NO: 1.

In another embodiment, the invention also provides polypeptide display libraries comprising a plurality of scaffolds of the invention. The libraries of the invention are useful for capturing and identifying target binding scaffolds of the invention.

In another embodiment the invention also provides isolated nucleic acid molecules encoding the scaffolds and libraries of the invention.

In another embodiment, the invention also provides methods of making, using, screening, optimizing, and engineering the scaffolds and libraries of the invention.

In yet another embodiment, the invention also provides pharmaceutical compositions comprising the scaffold of the invention.

In another embodiment, the invention also provides methods of treating, preventing, ameliorating, detecting, diagnosing, or monitoring a disease or symptoms thereof, in a patient by administering therapeutically effective amounts of the scaffold of the invention or pharmaceutical compositions comprising the scaffold of the invention.

BRIEF DESCRIPTION OF THE FIGURES

For the purpose of illustrating the invention, there are depicted in the drawings certain embodiments of the invention. However, the invention is not limited to the precise arrangements and instrumentalities of the embodiments depicted in the drawings.

FIG. 2. A structural comparison of the wildtype $CheB_c$ domain with an example of a scaffold of the invention. (A) A diagrammatic representation of the structure of a polypeptide comprising the wildtype $CheB_c$ domain (PDB ID: 3SFT) (SEQ ID NO: 80). (B) A diagrammatic representation of a model of a test loop graft construct of the scaffold of the invention with 3 artificial loops grafted (SEQ ID NO: 11).

FIG. 4. A diagrammatic representation of the polypeptide sequence of the $CheB_c$ domain (SEQ ID NO: 1) showing a diagrammatic representation of the regions of secondary structure comprising alpha helices, beta strands and a $3_{10}$ helix, connected by loop regions (based on the annotation of Cho K. et. al, 2011). Candidate loop regions for randomization comprise the amino acid residues underlined in the figure.

FIG. 5. A diagrammatic representation of the polypeptide sequence of the $CheB_c$ domain (SEQ ID NO: 1) with the positions selected for test loop grafting underlined.

FIG. 6. A diagrammatic representation of the aligned polypeptide sequences of the test loop graft constructs of the scaffold of the invention. The sequence identities are shown to the right of their respective sequences in the alignment scheme. The alignment scheme shows constructs with test loop grafts in positions 2 and 3 (SEQ ID NO: 8), test loop grafts in positions 1 and 2 (SEQ ID NO: 9), test loop grafts in positions 1 and 3 (SEQ ID NO: 10), and test loop grafts in positions 1 and 2 and 3 (SEQ ID NO: 11) aligned with the polypeptide sequence of the $CheB_c$ domain (SEQ ID NO: 1) which contains no test loop grafts. The positions of the test loop grafts in the SEQ ID NO: 11 example are underlined and labeled (1), (2) and (3) in the figure to indicate the test loop graft positions 1, 2, and 3 respectively.

FIG. 12B. ELISA screening of individual clones from selection outputs against target HER2. The bar graphs show the ELISA signals obtained from clones obtained from the outputs of the third round of phage display selections carried out with the HER2 target at (i) a concentration of 5 nM and (ii) a concentration of 0.5 nM (Plate 3 and Plate 4, respectively).

1-12C: 91 nM. The sequence identities of the proteins are SEQ ID NO: 75, SEQ ID NO: 74 and SEQ ID NO: 57 respectively.

Figure 17A:
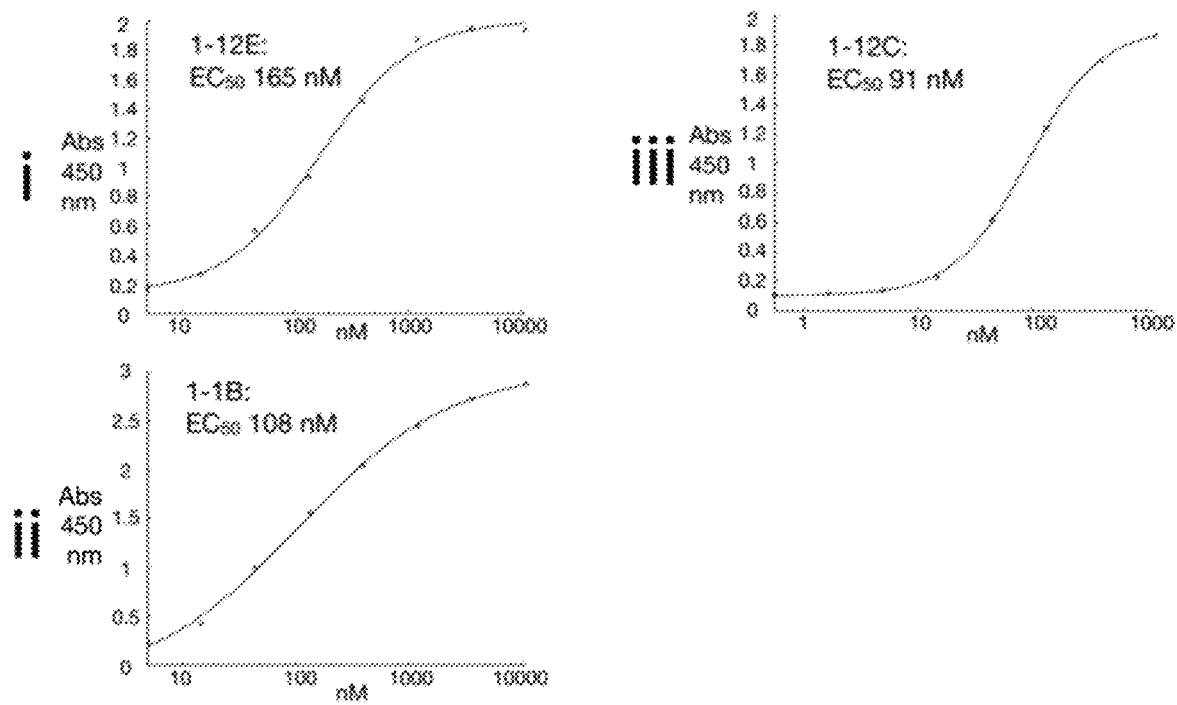
FIG. 17A. Affinity determination of selected purified PD-L1 binding proteins of the scaffold of the invention. $EC_{50}$ was determined by ELISA. The $EC_{50}$ are indicated on the figure as (i) 1-12E: 165 nM; (ii) 1-1B: 108 nM; (iii)
Figure 17B:
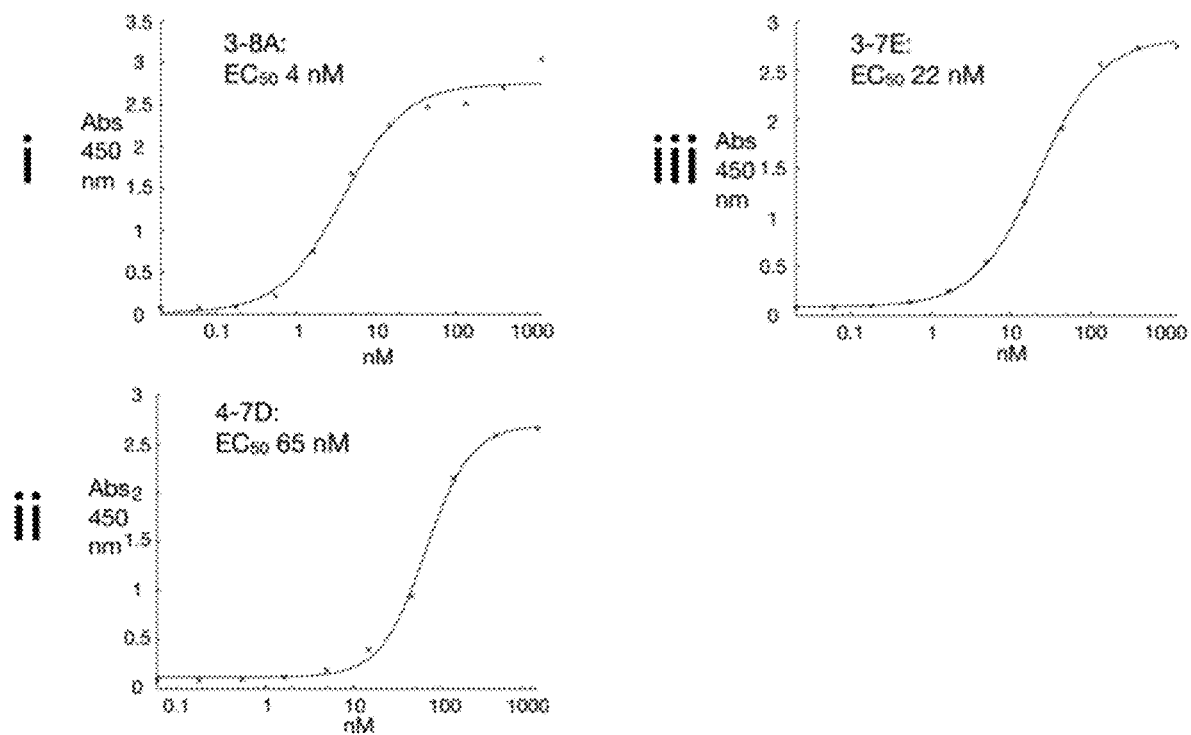

FIG. 17B. Affinity determination of selected purified HER2 binding proteins of the scaffold of the invention. $EC_{50}$ was determined by ELISA. The $EC_{50}$ are indicated on the figure as (i) 3-8A: 4 nM; (ii) 4-7D: 65 nM; (iii) 3-7E: 22 nM. The sequence identities of the proteins are SEQ ID NO: 66, SEQ ID NO: 69, and SEQ ID NO: 65, respectively.

FIG. 18. A diagrammatic representation of part of a computer generated output of a polypeptide sequence alignment of the $CheB_c$ domain SEQ ID NO: 1 (Query) with the orthologous domain in the chemotaxis protein CheY of *Fervidobacterium pennivorans* SEQ ID NO: 48 (Sbjct), GenBank ID: ANE42371.1 amino acid residues 147-337. The positions selected for test loop grafting in Query and Sbjct polypeptides are boxed. A homology of 78% amino acid residue identity was observed between the homologous regions of the two proteins. Sequence alignment was performed with the blastp algorithm on the NCBI (National Center for Biotechnology Information) website. The residue numbering of the *Fervidobacterium* sp. derived protein corresponds to the GenBank ID numbering scheme.

FIG. 19. A diagrammatic representation of test loop grafting of a *Fervidobacterium pennivorans* derived protein domain. (A) A diagrammatic representation of the polypeptide sequence of Chemotaxis protein CheY of *Fervidobacterium pennivorans* (SEQ ID NO: 48) GenBank ID: ANE42371.1 amino acid residues 147-337, with the positions selected for test loop grafting underlined. The residue numbering in the figure corresponds to SEQ ID NO: 48. (B) A diagrammatic representation of the polypeptide sequence of the test loop graft construct (SEQ ID NO: 49), derived from Chemotaxis protein CheY of *Fervidobacterium pennivorans* GenBank ID: ANE42371.1 amino acid residues 147-337, with the artificial test loop grafts underlined. The residue numbering in the figure corresponds to SEQ ID NO: 49.

FIG. 20. A diagrammatic representation of part of a computer generated output of a polypeptide sequence alignment of the wildtype polypeptide sequence of Chemotaxis protein CheY of *Fervidobacterium pennivorans* GenBank ID: ANE42371.1 amino acid residues 147-337 (SEQ ID NO: 48) (Sbjct), with the corresponding test loop graft construct (SEQ ID NO: 49) (Query). Sequence alignment was performed with the blastp algorithm on the NCBI (National Center for Biotechnology Information) website. The residue numbering in the figure of the wildtype CheY polypeptide sequence (Sbjct) corresponds to the GenBank ID numbering scheme, whereas the residue numbering in the figure of the test loop graft construct (Query) corresponds to SEQ ID NO: 49.

Figure 21:
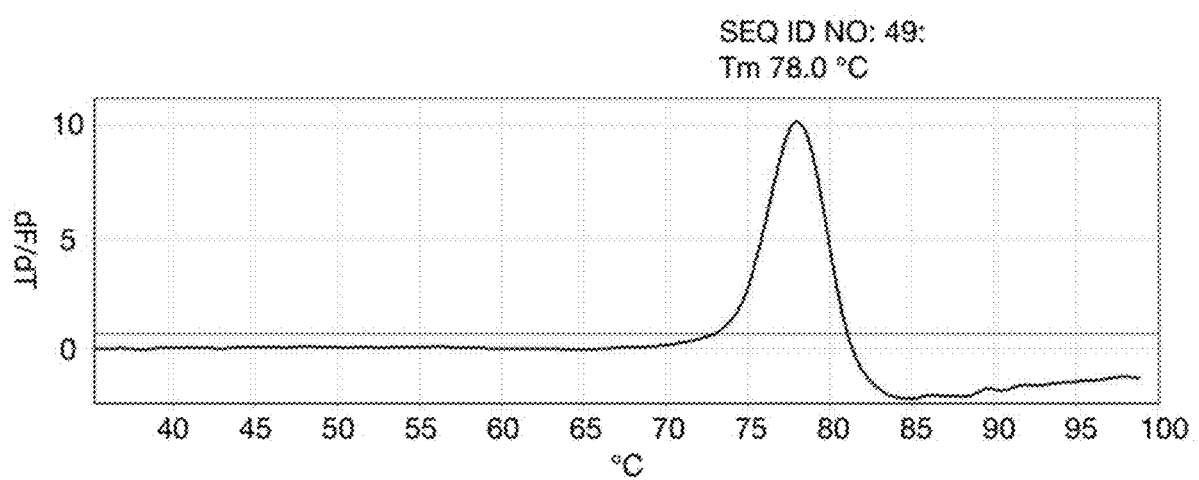

FIG. 21. First derivative curve of fluorescence intensity obtained by differential scanning fluorimetry (DSF) of the purified protein of the test loop graft construct (SEQ ID NO: 49) derived from Chemotaxis protein CheY of *Fervidobacterium pennivorans*. The melting temperature of the protein was 78.0° C.

TABLES

Brief Description of the Tables

Table 1. The nucleotide sequences of the PCR primers used for amplification, assembly, and cloning of the scaffold framework DNA fragments, the test loop graft DNA fragments, and the randomized loop region DNA fragments of the scaffold of the invention.

Table 2. Purification yield and melting temperature of the test loop graft constructs of the scaffold of the invention with test loop grafts in positions 2 and 3 (SEQ ID NO: 8), test loop grafts in positions 1 and 2 (SEQ ID NO: 9), test loop grafts in positions 1 and 3 (SEQ ID NO: 10), and test loop grafts in positions 1 and 2 and 3 (SEQ ID NO: 11). Proteins were purified from 50 mL *E. coli* shake flask cultures in 2×YT medium.

TABLE 1

| Primer name | Sequence | SEQ ID NO |
|---|---|---|
| EcoRIF | ATACAGAATTCTGGTTCTCACATGGTTTCTGGTAAAATCGTTG | SEQ ID NO: 21 |
| FR1F | GGTTCTCACATGGTTTCTGGTAAAATCGTTG | SEQ ID NO: 22 |
| FR1R | TCCGTGCTGAACAACAACGATCGGAGCC | SEQ ID NO: 23 |
| FR2F | GGGACCAAATCTCTGGCTCAGCGTCTGG | SEQ ID NO: 24 |
| FR2R | ACCAGATTTGTCCAGGAAGAAGAAAACTTTACCGTTCTG | SEQ ID NO: 25 |
| FR3F | GGGGTTCGTCCGGCTGTTGACTTCACCCT | SEQ ID NO: 26 |
| FR3R | TCCACCGGTCAGGATAACAGCGATGGTT | SEQ ID NO: 27 |
| FR4F | GGTGGTGACGGTACTAAGGGCGCGTTCLAA | SEQ ID NO: 28 |
| FR4R | AACCAGTTCGATCAGTTTTTCCGG | SEQ ID NO: 29 |
| AscIR | ATCATGGCGCGCCAACCAGTTCGATCAGTTTTTCCGG | SEQ ID NO: 30 |
| L1F | GGCTCCGATCGTTGTTGTTCAGCACGGA | SEQ ID NO: 31 |
| L1R | CCAGACGCTGAGCCAGAGATTTGGTCCC | SEQ ID NO: 32 |
| L2F | CAGAACGGTAAAGTTTTCTTCTTCCTGGACAAATCTGGT | SEQ ID NO: 33 |
| L2R | AGGGTGAAGTCAACAGCCGGACGAACCCC | SEQ ID NO: 34 |

TABLE 1-continued

| Primer name | Sequence | SEQ ID NO |
|---|---|---|
| L3F | AACCATCGCTGTTATCCTGACCGGTGGA | SEQ ID NO: 35 |
| L3R | TTTGAACGCGCCCTTAGTACCGTCACCACC | SEQ ID NO: 36 |

TABLE 2

| Clone | Tm (° C.) | mg protein (50 ml culture) |
|---|---|---|
| SEQ ID NO: 8 | 89.9 | 1.4 |
| SEQ ID NO: 9 | 92.0 | 1.7 |
| SEQ ID NO: 10 | 91.3 | 1.4 |
| SEQ ID NO: 11 | 89.4 | 1.3 |

DETAILED DESCRIPTION

The protein scaffold described herein has been designed to be superior both to antibody-derived fragments and to non-antibody domains. The major advantage of the scaffold of the invention over antibody fragments is structural. The scaffold is derived from a structurally conserved, stable and soluble protein domain found in a wide variety of prokaryotes. Consequently it exhibits better folding and thermostable properties than antibody fragments whose creation involves the removal of parts of the antibody native fold, often exposing amino acid residues that, in an intact antibody, would be buried in a hydrophobic environment, such as an interface between variable and constant domains. Exposure of such hydrophobic residues to solvent increases the likelihood of aggregation.

Moreover, the scaffold of the invention provides the functional advantages of antibody molecules. In particular, despite the fact that the scaffold of the invention is not an immunoglobulin, the artificially engineered binding surface has some designed similarity to that of the variable region of the IgG heavy chain, being comprised of solvent exposed variable loops in an analogous fashion to antibody CDRs. Because of this structure, the scaffold of the invention possesses antigen binding properties that are similar in nature to those of antibodies. As a result, loop randomization and shuffling strategies may be employed in vitro that are similar to the process of affinity maturation of antibodies in vivo.

Figure 1:
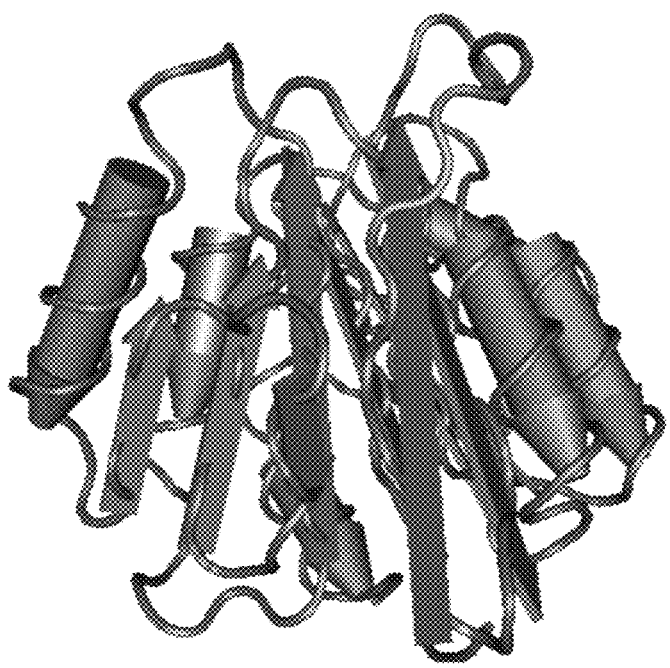
FIG. 1. A diagrammatic representation of the structure of a polypeptide comprising the wildtype $CheB_c$ domain (PDB ID: 3SFT) (SEQ ID NO: 80).

The scaffold of the invention is based on the structure of the CheB methylesterase C-terminal catalytic domain (CheB$_c$), which plays a key role in chemotaxis and is thus observed in many prokaryotes. It was found that the *Thermotoga maritima* CheB$_c$ domain was thermostable, soluble, and easy to produce, properties which facilitate the generation of diverse collections of variants of the scaffold of the invention capable of binding specific targets. Furthermore, analysis of structural data of the wildtype *Thermotoga maritima* CheB$_c$ domain (FIG. 1) indicated the location of several exposed surface residues within the secondary structural elements and connecting loops. These exposed surface residues are attractive candidates for the introduction of structural variation and generation of diverse pools of scaffold molecules with artificial binding surfaces. In the present invention, some of these residues were tested to evaluate their suitability for randomization.

Figure 3:
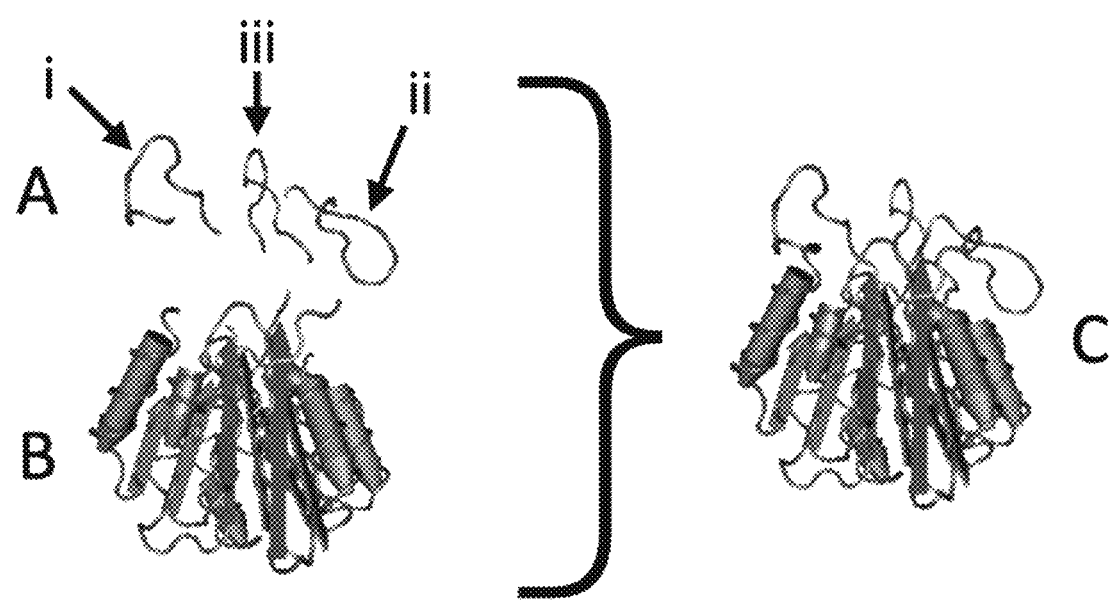
FIG. 3. A diagrammatic representation of an artificially dissected scaffold of the invention derived from a model of a test loop graft construct of the scaffold of the invention with 3 artificial loops grafted. (A) Structural representations of the artificial loops (comprising the three test loop grafts). Depicted in the figure are the individual artificial loops in (i) position 1, (ii) position 2, and (iii) position 3, and consisting of SEQ ID NO: 85, SEQ ID NO: 86 and SEQ ID NO: 87, respectively. (B) A structural representation of the base of the scaffold. (C) A structural representation of a test loop graft construct of the scaffold of the invention, which consists of the three test loop grafts and the base of the scaffold combined, and comprises SEQ ID NO:11.
Figure 7:
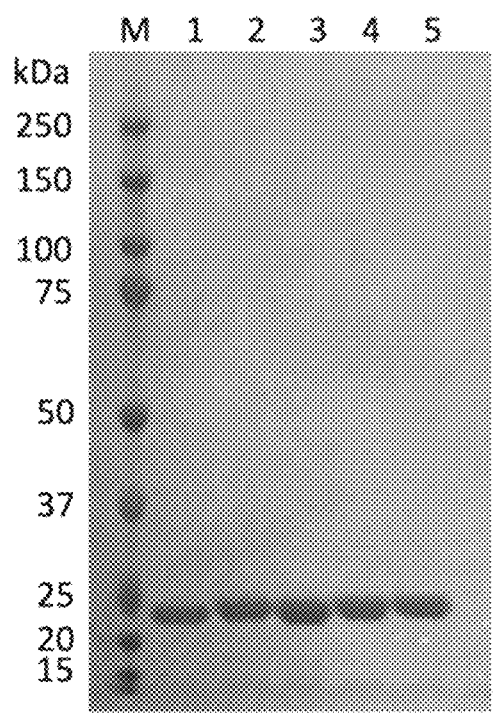
FIG. 7. SDS-PAGE of the purified test loop graft constructs of the scaffold of the invention. The lanes are labeled at the top of the figure. Lane M: Precision Plus Protein Standard (Bio-Rad); Lane 1: the $CheB_c$ domain (SEQ ID NO: 1); Lane 2: construct with test loop grafts in positions 2 and 3 (SEQ ID NO: 8); Lane 3: construct with test loop grafts in positions 1 and 2 (SEQ ID NO: 9); Lane 4: construct with test loop grafts in positions 1 and 3 (SEQ ID NO: 10); Lane 5: construct with test loop grafts in positions 1 and 2 and 3 (SEQ ID NO: 11).
Figure 8:
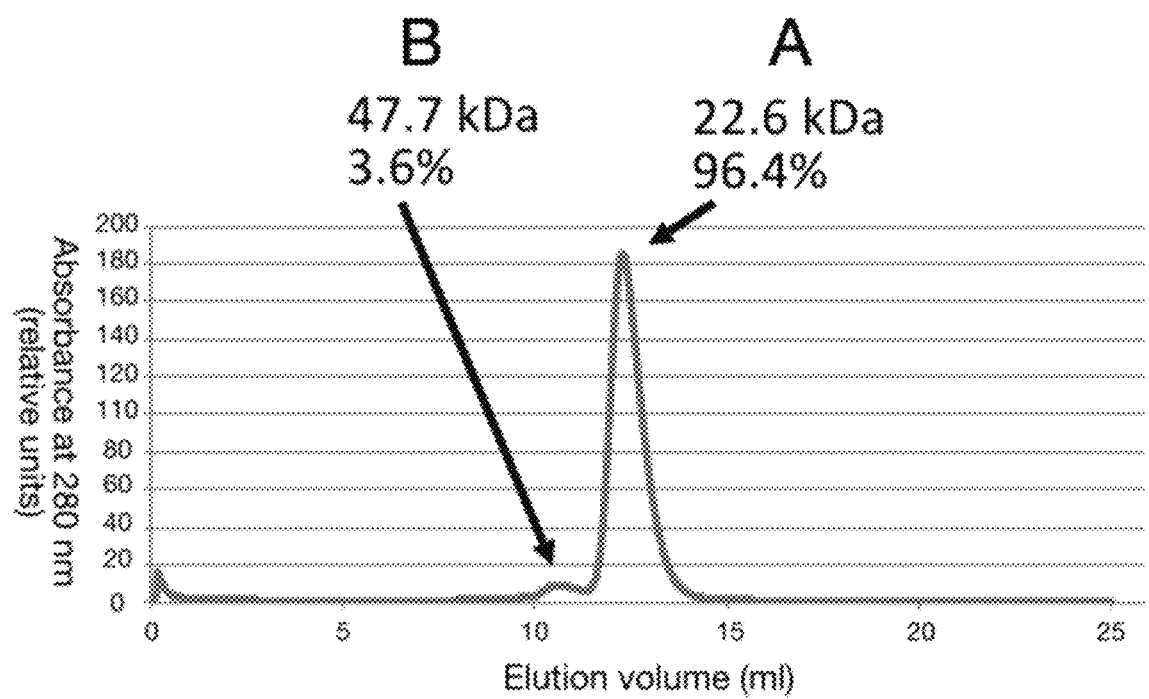
FIG. 8. Size exclusion chromatography profile of a purified test loop graft construct of the scaffold of the invention with test loop grafts in positions 1 and 2 and 3 (SEQ ID NO: 11). The labeled arrows in the figure indicate the SEC chromatogram derived size estimates of the protein species and their relative abundance. (A) shows the 22.6 kDa protein peak species (corresponding to the monomeric fraction) was present at 96.4%. (B) shows the 47.7 kDa protein peak species (corresponding to the dimer) was present at 3.6%.
Figure 9:
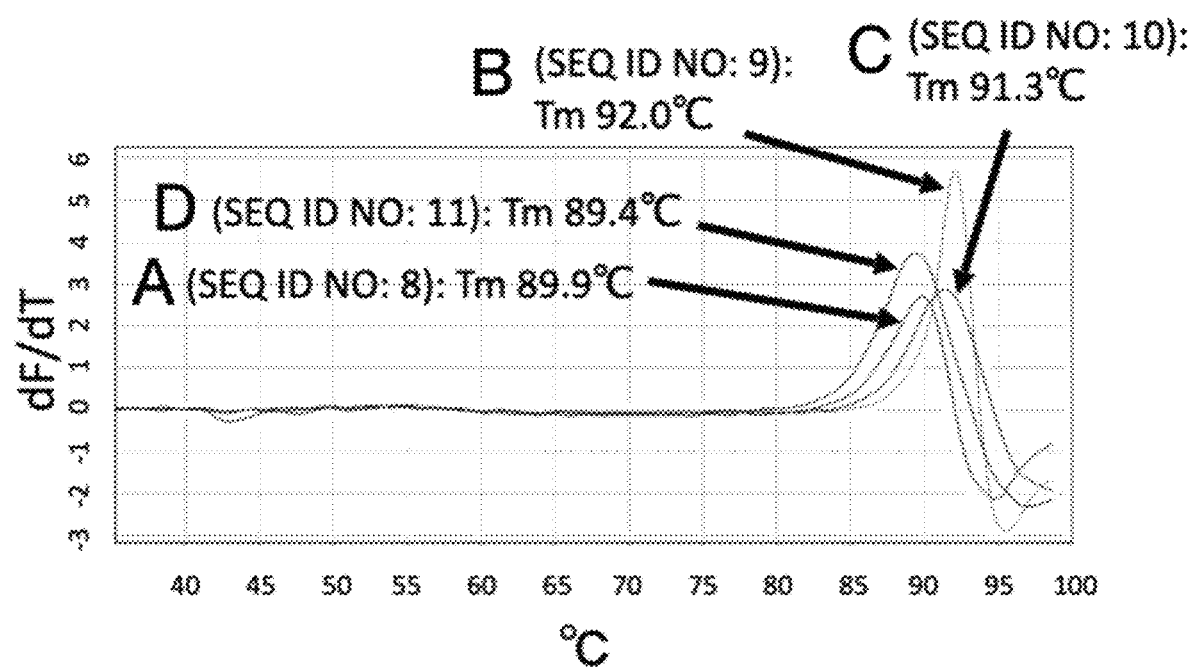
FIG. 9. First derivative curves of fluorescence intensity obtained by differential scanning fluorimetry (DSF) of the purified test loop graft constructs of the scaffold of the invention. (A) The construct with test loop grafts in positions 2 and 3 (SEQ ID NO: 8) had a Tm of 89.9° C. (B) The construct with test loop grafts in positions 1 and 2 (SEQ ID NO: 9) had a Tm of 92.0° C. (C) The construct with test loop grafts in positions 1 and 3 (SEQ ID NO: 10) had a Tm of 91.3° C. (D) The construct with test loop grafts in positions 1 and 2 and 3 (SEQ ID NO: 11) had a Tm of 89.4° C.

In the present invention, it was surprisingly found that the CheB$_c$ domain was remarkably tolerant to the randomization design of the invention, which includes the grafting of unstructured and artificially long loop regions (FIGS. 2 and 3). As reported herein, the scaffold of the invention was found to be monomeric and thermostable with experimental test loop grafting (FIGS. 8 and 9). This is surprising because it is generally expected that insertion of an unnaturally long unstructured loop will destabilize a given domain (Schilling J. et al., 2014, Nagi A., Regan L. 1997, Regan L. 1999). This is also surprising, since in the present invention, the experimental test loops did not include a stabilizing loop stem region (as in, for example Schilling J. et al., 2014), or other engineered loop stabilizing features. Furthermore, the thermostability of the scaffold of the invention was not unreasonably affected by the grafting of two, or even three unstructured test loops, in various grafting positions in the recombinant test protein constructs that were evaluated in the randomization design (FIG. 6), all of which were of similar stability (FIG. 9).

Thus, in the present invention the CheB$_c$ domain was found to be effectively exploitable for the purpose of engineering a highly randomized library of the scaffold of the invention for the isolation of binding proteins.

It was found that the randomization design and random screening approach employed herein provides a facile and efficient means of obtaining specific binders against a target of interest. Thus, the scaffold of the invention is expected to be particularly useful for the development of, for example, but not limited to a variety of therapeutics, diagnostics, and detection reagents against a multitude of targets.

As a result of the above, the present invention relates to a recombinant scaffold protein comprising a recombinant CheB$_c$ domain comprising a plurality of alpha helices and beta strands and a $3_{10}$ helix, linked by a plurality of loop regions (a modified doubly-wound α/β sandwich fold) (FIG. 4), having at least 50%, at least 60%, at least 70%, at least 75%, at least 80%, at least 90%, at least 95%, or at least 99% amino acid sequence identity outside the loop regions to SEQ ID NO: 1; and wherein at least one loop region is a non-naturally occurring variant of the cognate loop region of SEQ ID NO: 1.

It is obvious to one skilled in the art that the $3_{10}$ helix consists of only a few amino acid residues and may be readily inserted, substituted, or deleted, using routine experimentation, to generate variants of the scaffold of the invention lacking a $3_{10}$ helix. Thus, one embodiment of the invention comprises a variant of the scaffold of the invention lacking a $3_{10}$ helix. Similarly, some of the other secondary structural elements, for example β9 (FIG. 4) are also small, and one skilled in the art could with minimal effort and a reasonable expectation of success, derive variants of the scaffold of the invention lacking one or more of these individual secondary structural elements.

In another specific embodiment, the scaffold of the invention comprises fourteen loop regions consisting of amino acid residue positions from 16 to 18 inclusive, from 29 to 37 inclusive, from 43 to 47 inclusive, from 60 to 61 inclusive, from 66 to 75 inclusive, from 80 to 84 inclusive, from 92 to 93 inclusive, from 103 to 107 inclusive, from 124 to 125 inclusive, from 135 to 137 inclusive, from 149 to 150 inclusive, from 160 to 162 inclusive, from 173 to 176 inclusive, and from 180 to 181 inclusive, of SEQ ID NO: 1, linked to secondary structural elements corresponding to the non-loop regions of SEQ ID NO: 1, and; wherein at least one of said loop regions is a non-naturally occurring variant of the cognate loop region of SEQ ID NO: 1, and; having at least 50%, at least 60%, at least 70%, at least 75%, at least 80%, at least 90%, at least 95%, or at least 99% amino acid sequence identity outside the non-naturally occurring variant loop regions to SEQ ID NO: 1.

In another specific embodiment, the scaffold of the invention comprises a sequence of four framework regions FR1 (SEQ ID NO: 40), FR2 (SEQ ID NO: 41), FR3 (SEQ ID NO: 42), and FR4 (SEQ ID NO: 43), wherein the framework region polypeptides have at least 50%, at least 60%, at least 70%, at least 75%, at least 80%, at least 90%, at least 95%, or at least 99% amino acid sequence identity to the cognate regions of SEQ ID NO: 1; connected by loop regions, wherein at least one loop regions is a non-naturally occurring variant of the cognate loop region of SEQ ID NO: 1.

In another embodiment, the invention also concerns the nucleic acids encoding the individual and collective library members of randomized variants of the scaffold of the invention. There are a variety of methods of introducing variations in nucleic acids encoding polypeptide sequences, including, but not limited to incorporating DNA fragments comprising degenerate codons or mixtures of coupled trinucleotides, employment of error-prone PCR, DNA fragment shuffling, and a variety of other methods and combinations of methods, and these methods are well known and readily employable by one who is skilled in the art.

In a specific embodiment, coupling of trinucleotide mixtures is a well known method which enables increased control of the relative frequency and variety of codons incorporated in a randomized DNA fragment. However, because of the incomplete precision of this method, artifactual codons are also incorporated, and random deletions or insertions of trinucleotides also occurs. These events provide additional sources of variation which may fortuitously enable the isolation of additional scaffold variants with useful properties, and thus scaffold variants arising from this well known source of additional variation comprise one embodiment of the invention. Similarly, the method employing degenerate NNK codon encoding oligonucleotides also results in a variety of well known artifacts. Thus, these two methods enable the generation of diverse DNA fragments encoding both controlled and fortuitous variations in polypeptide sequences. As a result of the above, in a specific embodiment of the invention, polynucleotides encoding the framework region polypeptides of the scaffold of the invention are connected to oligonucleotides encoding variant loop region polypeptides, randomized by either trinucleotide coupling or degenerate NNK codons, or combinations thereof.

In another specific embodiment, oligonucleotides encoding variant loop region polypeptides may be randomized by a variety of degenerate codons, for example but not limited to NNK, NNS, NHK, VNK, NNN, or combinations thereof. In other embodiments, oligonucleotides encoding variant loop region polypeptides may be randomized by error prone polymerases such as in error prone PCR, by mutagenic strains of cultured cells or microorganisms, or by a variety of other means of random or targeted mutagenesis known to one skilled in the art.

In a specific embodiment of the invention, DNA fragments comprising sequences encoding randomized loop regions of the scaffold of the invention (for example, those shown in SEQ ID NOs: 16-20) are connected with DNA fragments comprising sequences encoding the framework regions of the scaffold of the invention (for example, those shown in SEQ ID NOs: 81-84), wherein the framework region polypeptides have at least 50%, at least 60%, at least 70%, at least 75%, at least 80%, at least 90%, at least 95%, or at least 99% amino acid sequence identity to the cognate regions of SEQ ID NO: 1. In a specific embodiment, the fragments are connected by overlap extension PCR, by means such as, for example, that represented in the scheme depicted in FIGS. 10 and 11. Of course, other suitable methods of generating recombinant DNA molecules may be substituted and are well known to one skilled in the art. In addition, a multitude of variations in loop lengths and encoded randomized amino acid compositions may be empirically tested by one skilled in the art to generate suitably randomized scaffold variants. Furthermore, it is well known to one skilled in the art that a multitude of possible nucleic acid sequences employing different codons may be utilized to encode the same polypeptide. One who is skilled in the art may select codons known to be utilized with varying frequencies within different organisms as a means, for example, of optimizing the production yield of the scaffold of the invention. Thus, the nucleic acid sequences of the present invention are not limited to the representative examples shown here.

In a specific embodiment, the scaffold of the invention comprises four framework regions FR1 (SEQ ID NO: 40), FR2 (SEQ ID NO: 41), FR3 (SEQ ID NO: 42), and FR4 (SEQ ID NO: 43), wherein the framework region polypeptides have at least 50%, at least 60%, at least 70%, at least 75%, at least 80%, at least 90%, at least 95%, or at least 99% amino acid sequence identity to the cognate regions of SEQ ID NO: 1; and three loop regions L1 (SEQ ID NO: 44), L2 (SEQ ID NO: 44), and L3 (SEQ ID NO: 47) wherein Xaa represents any amino acid; and wherein L1 is linked between FR1 and FR2, L2 is linked between FR2 and FR3, and L3 is linked between FR3 and FR4 to form a contiguous polypeptide comprising the arrangement FR1-L1-FR2-L2-FR3-L3-FR4. In another specific embodiment, in the L1, L2 and L3 loop regions Xaa represents an amino acid taken from a group consisting of serine, aspartic acid, arginine, alanine, leucine, threonine, asparagine, tryptophan, glycine, glutamic acid, valine and tyrosine. In one embodiment, the scaffold of the invention comprises, for example, a polypeptide represented by SEQ ID NO: 2. In another embodiment, this is encoded by a polynucleotide comprising, for example, a polynucleotide represented by SEQ ID NO: 5. One who is skilled in the art can with minimal effort substitute other polynucleotides to obtain a polynucleotide comprising a coding region for a polypeptide represented by SEQ ID NO: 2.

In another specific embodiment, the scaffold of the invention comprises four framework regions FR1 (SEQ ID NO: 40), FR2 (SEQ ID NO: 41), FR3 (SEQ ID NO: 42), and FR4 (SEQ ID NO: 43), wherein the framework region polypeptides have at least 50%, at least 60%, at least 70%, at least 75%, at least 80%, at least 90%, at least 95%, or at least 99% amino acid sequence identity to the cognate regions of SEQ ID NO: 1; and three loop regions L1 (SEQ ID NO: 45), L2 (SEQ ID NO: 46), and L3 (SEQ ID NO: 47) wherein Xaa represents any amino acid; and wherein L1 is linked between FR1 and FR2, L2 is linked between FR2 and FR3, and L3 is linked between FR3 and FR4 to form a contiguous polypeptide comprising the arrangement FR1-L1-FR2-L2-FR3-L3-FR4. In another specific embodiment, in the L1 and L2 loop regions Xaa represents any amino acid, and; for the L3 loop region Xaa represents an amino acid taken from a group consisting of serine, aspartic acid, arginine, alanine, leucine, threonine, asparagine, tryptophan, glycine, glutamic acid, valine and tyrosine. In one embodiment, the scaffold of the invention comprises, for example, a polypeptide represented by SEQ ID NO: 3. In another embodiment, this is encoded by a polynucleotide comprising, for example, a polynucleotide represented by SEQ ID NO: 6. One who is skilled in the art can with minimal effort substitute other polynucleotides to obtain a polynucleotide comprising a coding region for a polypeptide represented by SEQ ID NO: 3.

In some embodiments, the scaffold of the invention may be made to bind to a target by grafting of loop regions obtained from other binding molecules, for example, but not limited to the CDRs of antibodies or the loop regions obtained from other polypeptides with known binding activity. In other embodiments, peptides with known activity, for example, antimicrobial peptides, cell membrane penetrating peptides, platelet aggregation inhibiting peptides, metastasis inhibiting peptides, immunomodulating peptides, and other peptides with known activities may be grafted into the scaffold.

In other embodiments, affinity maturation may be carried out on the scaffold of the invention to obtain binders with stronger or weaker binding affinity or biological activity than a parent clone. There are many methods of introducing sequence variation for affinity maturation purposes which are well known to one skilled in the art, including, but not limited to, loop randomization, error prone PCR, sexual PCR, and other methods. Such methods may also be used to obtain binders with altered biophysical, physiological or other properties.

In other embodiments, the scaffold of the invention may be randomized with, for example a variety of different loop lengths, loop grafting positions, loop amino acid compositions and numbers of grafted loops. Being made aware of the findings herein that the $CheB_c$ domain is remarkably tolerant to the randomization design of the invention, which includes the grafting of unstructured and artificially long loop regions, one who is skilled in the art would reasonably expect that other grafting solutions could also be readily found with minimal effort. It would thus be a trivial matter for one skilled in the art to make use of routine testing to identify alternative randomizing loop grafting schemes with a reasonable expectation of success.

In some embodiments, variation may be introduced into one or more structural regions of the scaffold of the invention outside of the loop regions. Being made aware of the findings disclosed herein, and by making use of, for example, freely available structural data, one skilled in the art would be able to identify and test regions of the scaffold suitable for mutation and randomization by no more than routine trial and error. Thus, in one embodiment, these non-loop regions may be used for the introduction of structural variation and generation of diverse pools of scaffold molecules with artificial binding surfaces.

In another embodiment, randomization methods may be employed to generate diverse pools of scaffold molecules with artificial binding surfaces comprising variants of loop regions, non-loop regions, and combinations thereof.

In some embodiments, variation may be introduced into regions of the scaffold of the invention not previously randomized, to generate further randomized libraries of the invention. Such variants may comprise for example, but not limited to variants of previously unrandomized loop regions or scaffold framework regions, to generate binders to a target with higher or lower affinity, or with altered biophysical, physiological or other properties.

In other embodiments, truncated or elongated versions of the scaffold of the invention may be easily generated. For example, it is known that the first four amino acid residues of SEQ ID NO: 1 are not resolved in a crystal structure of a polypeptide comprising the wildtype $CheB_c$ domain (PDB ID: 3SFT) (SEQ ID NO: 80). Thus it would be obvious to one skilled in the art that these four residues are not essential to the structure of the scaffold of the invention, and one, two, three, four, or more of these N-terminal residues may be freely substituted or deleted. In other embodiments, being aware of the high thermostability of the scaffold of the invention disclosed herein, it would be a trivial matter for one skilled in the art to generate a variety of N-terminal, C-terminal, or internally truncated or elongated versions of the scaffold of the invention by routine experimentation, by making use of structural and sequence data, with a reasonable expectation of success.

In another embodiment, circularly permutated versions of the scaffold of the invention may be formed by connecting the N-terminus and C-terminus of the scaffold molecule and introducing new termini at another position. Knowing that the N-terminus and C-terminus of the scaffold are proximal to each other, and being aware of the stability of the scaffold, it would be obvious and trivial for one who is skilled in the art to use the available structural data of the scaffold to identify suitable positions for engineering alternative termini to generate circularly permutated scaffolds of the invention. Such constructs could be easily engineered and tested for stability without undue effort using no more than routine experimentation.

In another embodiment, circularized molecules of the scaffold of the invention without termini could also be constructed using, for example, intein mediated trans splicing circularization, disulphide bond formation, isopeptide bond formation, or a variety of chemical or molecular biological techniques known to one skilled in the art. Circularized proteins are well known to have generally enhanced conformational stability and resistance to exopeptidases and heat degradation.

In another embodiment, scaffolds of the invention with enhanced stability may be generated by a variety of means, such as, for example, introducing intramolecular disulphide bonds, intramolecular chemical crosslinking, isopeptide bond formation, and other well known means. In another embodiment, well known stability maturation techniques such as those involving generating libraries of mutated scaffold variants, and well known methods of selection by virtue of enhanced stability or production yield may be carried out. In another embodiment, rational design of enhanced stability variants may be carried out. In yet another embodiment, fusion of the scaffold of the invention with proteins known to have high solubility or stability may be used to improve the overall solubility or stability of molecules comprising the scaffold of the invention. In another embodiment, resistance to aggregation, or resistance to degradation by proteolytic enzymes, or resistance to chemical degradation may be improved by the above or by other well known stability enhancing and selecting techniques.

It is known that high structural conservation exists in $CheB_c$ domains from divergent species (Cho K., et al., 2011) even though the amino acid sequences of $CheB_c$ domains may be quite divergent. Thus it is trivial for one who is skilled in the art to develop randomized protein scaffolds from proteins comprising domains orthologous to the *Ther-*

*motoga maritima* CheB$_c$ domain, by making use of known structural conservation to identify, for example, the corresponding orthologous loop regions to those reported in the present invention.

In another embodiment, polypeptide or polynucleotide sequence homology searches may be used to identify proteins which may be exploited in a similar way to the present invention. For example, by a routine polypeptide homology search, it could be determined that several proteins, including that of a domain of the chemotaxis protein CheY of *Fervidobacterium pennivorans* (GenBank ID: ANE42371.1 amino acid residues 147-337) (SEQ ID NO: 48), exhibited homology to the CheB$_e$ domain (SEQ ID NO: 1) (FIG. 18). The *Fervidobacterium* sp. protein domain was thus selected as one candidate out of the many identified homologous candidates for test loop grafting. By making use of the loop graft positions disclosed in the present invention, the polypeptide sequence alignment could be easily used to direct the insertion points for candidate test loop grafts on the *Fervidobacterium* sp. protein domain (FIG. 18). In another embodiment, being aware of the above, one who is skilled in the art could further make use of structural information, for example, that obtainable from freely available predictive structural modelling software (such as, for example SWISS-MODEL, University of Basel), to readily predict the individual exposed loop residue positions in the *Fervidobacterium* sp. protein domain, to even more precisely direct the insertion points for candidate test loop grafts. By making further use of the details of the randomization strategy disclosed in the present invention, artificially long test loop regions could be readily grafted (FIGS. 19 and 20). In this example, the resultant artificially test loop grafted *Fervidobacterium* sp. protein (SEQ ID NO: 49), notwithstanding having three unnaturally long unstructured test loops, was easily produced and thermostable (FIG. 21), even though the sequence identity of the wildtype *Fervidobacterium* sp. protein (SEQ ID NO: 48) to the $CheB_c$ domain (SEQ ID NO: 1) was less than 80%. Furthermore, individual loop grafted variants of the *Fervidobacterium* sp. protein would be expected to exhibit even lower sequence homology to the scaffold of the invention. By making use of these findings, and being aware of the outcome of the library construction and screening described in the present invention, it would only require routine work using well known techniques for one skilled in the art to construct a randomized library of, for example, the above *Fervidobacterium* sp. protein domain, and obtain protein molecules with binding properties to a target of interest, with a reasonable expectation of success. Thus, being aware of the disclosures and teachings in the present invention, it would only require basic skills and routine experimentation for one skilled in the art to readily identify and make use of other homologous proteins with similarly exploitable properties to the scaffold of the invention.

Further embodiments of the invention are directed towards the means of screening a randomized library of the invention for specific binding to target molecules.

One embodiment of the invention comprises a method of obtaining a polypeptide scaffold that binds to a target, said method comprising (a) contacting a target ligand with the randomized library under conditions that allow a scaffold: target ligand complex to form and, (b) obtaining from the complex, the scaffold that binds the target ligand.

The underlying principle of all selection technologies is the physical association of the phenotype (i.e. the displayed protein) and the genotype (i.e. the nucleic acid encoding the displayed protein). Different selection technologies use different strategies to achieve this association, and are well known to one skilled in the art.

Thus, in some embodiments, examples of such technologies include, but are not limited to, virus display, bacterial display, yeast display, mammalian cell display, mRNA display, ribosome display, cDNA display, or phage display. For example, filamentous phage display has been observed to survive extreme selection conditions such as heat (Dudgeon K., et al., 2013) and in vivo selections in live animals (Du B., et al., 2010).

In a specific embodiment of the invention, phage display is chosen as the selection technology.

Although most phage display methods have used filamentous phage, lambdoid phage display systems, T4 phage display systems, and T7 phage display systems are also known.

In a specific embodiment of the invention, phage display is carried out with the scaffold of the invention fused to the full-length pIII protein of filamentous M13 phage. However, phage display of the scaffold of the invention is not limited to this example. It is well known to one who is skilled in the art that filamentous phage display can be carried out by fusing the protein of interest to the N-terminus of a full-length pIII minor coat protein, or to truncated derivatives thereof, or recombinant derivatives thereof, and these may be easily substituted by one skilled in the art.

It is well known to one skilled in the art that display of a protein of interest on the surface of phage is typically dependent on the translocation of the protein of interest to the bacterial periplasm. In some embodiments, a fusion protein comprising the protein of interest fused to a phage coat protein is translocated. In other embodiments, the protein of interest is allowed to form a disulfide bond with a phage coat protein after translocation to the periplasm. A wide variety of signal sequences suitable for translocation of various proteins of interest to the periplasm have been described and are well known to one skilled in the art. Additional signal sequences can be readily identified from proteins which are already known to be efficiently and abundantly exported to the periplasm (Schmidt A. et al., 2015), and these obvious choices of signal sequences can easily be fused to a protein of interest by means of established techniques known to one skilled in the art. Well known assays such as, for example ELISA may be easily employed to monitor the display of proteins of interest on phage particles when fused to a variety of signal sequences (Zhao N. et al., 2016). Thus, using routine methods and without undue experimentation, it would be a trivial matter for one who is skilled in the art to construct a variety of suitable phage display vectors exploiting a diversity of signal sequences for the purpose of phage display of the scaffold of the invention, with a reasonable expectation of success.

In a specific embodiment of the invention, a modified pADL-10b phagemid vector (Antibody Design Labs) comprising EcoRI and AscI restriction enzyme sites corresponding to the restriction sites of the library inserts is used for the construction of the library of the invention and the generation of fusions of the scaffold of the invention with the phage pIII protein for display on phage particles. The DNA fragments encoding the randomized scaffolds of the invention are cloned into the vector via the EcoRI and AscI sites to generate a multitude of different recombinant phagemids encoding different randomized scaffold library members. Numerous other suitable restriction enzymes or other suitable methods of generating recombinant DNA are well known to one who is skilled in the art and may be substituted.

In a specific embodiment, these recombinant phagemids are then transformed into the E. coli strain XL1-Blue to generate a multitude of clones which collectively encode a multitude of different randomized library members of the scaffold of the invention. Of course, many other suitable E. coli strains such as TG1 may be easily substituted and are well known to one skilled in the art. Typically, a library complexity of the order of $1 \times 10^{10}$ members can be obtained by this method.

In a specific embodiment of the invention, this library is subsequently superinfected in liquid culture according to known methods with an M13-helper phage, such as VCSM13. Other helper phage strains such as, for example, M13KO7 may be readily substituted, and are well known to one who is skilled in the art. These helper phage strains often contain a mutated DNA sequence that favors the packaging of the phagemid (containing the individual randomized library genes encoding the scaffolds of the invention) into the mature phage particles, thus generating a physical linkage between the individual phage displayed randomized library members of the scaffolds and the genes which encode them.

In a specific embodiment, after this infection the incubation temperature of the culture is reduced for production of the phage particles displaying the randomized library members of the scaffold of the invention. Specific incubation temperatures are those in which the fusion protein of the scaffold of the invention with the phage coat protein is known to be efficiently produced, for example, 26° C. In a specific embodiment of the present invention, expression of the gene for the pIII fusion protein with the scaffolds of the invention is induced in the bacterial cells from the phagemid lac promoter by the addition of IPTG to 0.5 mM. The induction conditions are chosen such that a substantial fraction of the phage produced presents at least one randomized scaffold of the invention. Of course, one skilled in the art may readily select other suitable experimental conditions, including use of other phagemid promoters, induction conditions, and so on by no more than trivial experimentation.

In another specific embodiment, the resultant mixture of recombinant phage are isolated after a culture incubation phase of, for example, 16 hours. Various methods are known for isolation of the phage mixture from the culture, such as for example precipitation with a concentrated solution of polyethylene glycol and NaCl from the bacterial culture supernatant. The isolated phage mixture displaying the multitude of randomized library members of the scaffold of the invention is then resuspended in a suitable buffer such as PBS with 20% (v/v) glycerol and aliquoted for storage at −80° C. Other suitable storage buffers and storage conditions are well known to one skilled in the art and may be substituted. Typically the phage titer obtained by this method is of the order of $10^{13}$ phage particles per milliliter.

In another embodiment, these phage library stocks containing a multitude of individual randomized scaffolds of the invention displayed on their respective phage particles are used as a source of obtaining high affinity binders to a desired target by selection methods that are well known to one skilled in the art. There are many possible variations to this method of selecting binders to a target, for example, using cells which overexpress the desired target molecule on their surface (to obtain binders against protein complexes), or selection against bacteria or virus particles (to obtain therapeutic candidates against infectious agents), or in vivo selections in living animals (to obtain tumor or tissue specific binders), or selections against components obtained from the above. In some embodiments, these methods involve enablement of immobilizing the target molecule to a solid support, incubating for a predetermined time interval with the phage library, washing away unbound phage library members, and using an elution buffer (such as, for example, an acidic buffer such as a buffer containing 100 mM glycine pH 2.2) to elute the phage library members which bind to the desired target molecule. There are a multitude of other elution methods well known to one skilled in the art, such as using buffers with basic pH, using proteases such as trypsin, high salt buffers, competition with unlabeled target to release binders, competition with other molecules known to bind the target, using conditions which alter the structure of the target, and other techniques which may be readily employed.

In one embodiment, the eluted phage library members are then used to infect a suitable strain of E. coli and generate multiple copies of the enriched phage library members, which are then used for subsequent selection cycles to obtain further enrichment of binding clones.

In another embodiment of the invention, the diversity of the selection outputs obtained at various stages of the enrichment process may be further increased by recombining the selection outputs with collections of variant loop regions to generate populations of variants of the enriched library members. In other embodiments, such variants may be introduced by, for example substituting loop regions with randomized variants, randomizing additional loop regions, or generating variants of the scaffold framework. In one embodiment, PCR may be used to recombine DNA obtained from selection outputs with DNA fragments encoding variant loop regions, and these may also be used to generate phage displaying variants of the enriched library members. Further cycles of selection using some or all of these types of enriched library member variants may be used to obtain more diverse target binding clones with desirable properties such as, for example, increased affinity. Thus, in one embodiment, library members comprising mixtures of loop variants generated using trinucleotide coupling or degenerate codons may be obtained, as well as comprising variations introduced by a multitude of other well known methods.

In a specific embodiment of the invention, a target is labelled with biotin, followed by subsequent capture of the biotinylated target to a surface coated with streptavidin, neutravidin, or a similar biotin binding molecule known to one skilled in the art. In some embodiments paramagnetic beads coated with a biotin binding surface may be employed. In this method the concentration of target molecules may be accurately controlled (for example, between 500 nM to 50 pM or lower) which facilitates selection of high affinity binding library members. Of course, there are numerous variations in target presentation and selection conditions which are well known and may be employed by one skilled in the art.

In another embodiment, after a number of selection cycles, a population of phage library clones which have been enriched for binding to the desired target are obtained. The individual phagemid clones encoding proteins of the scaffold of the invention which have binding activity are contained in this population. The genes encoding these binders may be obtained by DNA purification of phagemids, or PCR amplification, or a variety of other methods known to one with skill in the art, and the polypeptide sequences may be deduced from their DNA sequences which can be easily obtained by DNA sequencing techniques well known to one skilled in the art. In another embodiment, after subcloning into appropriate expression vectors, individual scaffolds of the invention of interest may be purified using a variety of purification procedures from a variety of host cells or in vitro translation systems well known to one skilled in the art. Techniques such as ELISA and surface plasmon resonance, or a variety of other techniques which are well known to one skilled in the art may be used to characterize binding affinity and specificity of individual binders.

Further embodiments of the invention relate to a polynucleotide coding for a binding protein or fusion protein of the scaffold of the invention, a vector comprising said polynucleotide, and a host cell comprising said polynucleotide and/or said vector. Polynucleotides can be DNA, RNA, or any other analogues thereof. There are many vectors and host cells known to one who is skilled in the art that may be utilized to suit multiple purposes. Such purposes may include (but are not limited to) for example, protein production, or gene therapy, or production of virus particles displaying or encoding for the protein of interest. One who is skilled in the art will be able to select the polynucleotides, vectors and host cells from a multitude of well known options and confirm their suitability by routine methods.

In another embodiment of the invention, a polynucleotide comprising a coding region for a polypeptide comprising a scaffold of the invention may be used for the in vivo production of said polypeptide by administration of said polynucleotide for the purpose of, for example, treatment of disease. In one embodiment, a nucleoside-modified RNA encoding said polypeptide may be administered intravenously in polymer-based or lipid-based formulations to enable translation of the nucleic acid and production of the polypeptide inside the body of the patient.

In other embodiments, the invention relates to the expression and purification of scaffolds of the invention and fusion proteins derived thereof.

In one embodiment, this comprises (a) isolating a nucleic acid molecule encoding the scaffold that binds the target ligand, (b) operably linking the nucleic acid to an expression vector and, (c) expressing the nucleic acid which has been operably linked to the expression vector in a cell.

It is well known to one skilled in the art that a multitude of host organisms, such as E. coli and other bacterial strains, yeasts and other eukaryotic cells including mammalian and insect cells, and multicellular organisms, as well as cell free expression systems can be employed for recombinant protein production. In addition, a choice between numerous expression vectors and expression methodologies is possible. Scaffolds of the invention can be produced and purified by a multitude of established methods, well known to one skilled in the art. The suitability of the method depends on the host organism used, the expression vectors and expression strategy employed, and other factors which are known to one skilled in the art. Thus, in some embodiments these well known methods of recombinant protein production may be readily employed by one skilled in the art.

In a specific embodiment, the purification of a scaffold of the invention can be simplified by the fusion of affinity tag peptide sequences, which have a known affinity to certain materials. For example, certain tags such as a polyhistidine tag, FLAG tag, Strep tag, glutathionine S-transferase, and a multitude of other tags are well known to one skilled in the art, and may be used in a multitude of affinity purification schemes. For example, these tags may be conveniently fused to the recombinant protein of interest, and employed to selectively capture the recombinant protein from complex mixtures by means of their respective affinity partners immobilized on resins or in columns or the like. In another embodiment, the binding target (or a variant of the binding target) of the scaffold of the invention itself could be used in an affinity purification scheme by one skilled in the art. In a further specific embodiment of the invention, such affinity tags may be removed from the recombinant binding protein of the scaffold of the invention by the engineering of protease cleavage sites between the affinity tags and the scaffold. A multitude of protease sites such as those of tobacco etch virus (TEV) protease, thrombin, Factor Xa, and numerous other protease sites are well known to one skilled in the art and may be selected freely.

In another embodiment, the scaffolds of the invention obtained may be used in an unmodified state, or may be further modified by the construction of a variety of fusion proteins such as bispecific or multispecific binding molecules, or fusions to a variety of other components. Said fusions, and those described in the following embodiments, may be formed by, for example but not limited to a dimerization domain, a covalent isopeptide bond, a chemical crosslink, a disulfide bond, an amino acid linker, or another means well known to one skilled in the art. In one specific embodiment, said amino acid linker would comprise a soluble and flexible polypeptide linker including small and/or hydrophilic amino acids such as glycine, serine, alanine and threonine residues, although one skilled in the art could employ a number of other amino acid combinations to generate a linker with desirable properties.

Thus, in another embodiment the invention relates to a fusion protein comprising at least two scaffolds of the invention to generate a bispecific or bivalent fusion molecule. In another embodiment, scaffolds of the invention could also be fused to generate multispecific and/or multivalent fusion molecules.

In another embodiment, the invention also relates to a fusion protein comprising one or more scaffolds of the invention fused to additional binding domains such as, for example, scFv or other domains having binding activity, to generate multispecific and/or multivalent target binding proteins.

In an additional embodiment, the invention relates to fusions of scaffolds of the invention to a protein or proteins which associate covalently or non-covalently to form multiprotein complexes, thus generating protein complexes possessing multivalent and/or multispecific binding activity. Said fusions may be formed by, for example but not limited to a dimerization domain, a chemical crosslink, a disulfide bond, an isopeptide bond, an amino acid linker, or another means well known to one skilled in the art.

In an additional embodiment, the invention relates to a fusion protein comprising one or more scaffolds of the invention fused to a functional Fc domain, in some specific embodiments a human Fc domain. This may comprise N-terminal or C-terminal Fc-fusions, or fusion to internal regions of the Fc domain, or to combinations of these. Furthermore, the resultant fusion proteins may comprise different binding scaffolds of the invention possessing specificities for different ligand targets, thus generating bispecific or multispecific ligand binding fusion proteins. In another embodiment, one or more scaffolds of the invention may also be fused to existing antibodies to generate enhanced functionality such as, for example, multispecific binding. In yet another embodiment, the Fc domain may be used to target or redirect the immune response of the organism to a specific binding site of the binding protein of the invention.

In a further embodiment, monovalent, bispecific or multispecific constructs employing one or more scaffolds of the invention may be used in immunotherapeutic applications such as developing CAR-T cell-like therapies. Other examples include (but are not limited to) recruiting T-cells or inhibiting immune checkpoints, either locally around cancer cells or systemically. One who is skilled in the art is aware of a multitude of biological targets and immune system mechanisms which may be effectively exploited to achieve this aim.

In another embodiment, the invention relates to a fusion protein comprising one or more scaffolds of the invention fused to a pharmaceutically and/or a diagnostically active component. A fusion protein of scaffolds of the invention may comprise non-polypeptide components such as non-peptidic linkers, non-peptidic ligands, or therapeutically or diagnostically relevant radionuclides. In specific embodiments, such pharmaceutically and/or diagnostically active components may be selected from a group comprising such molecules as cytokines, toxic compounds, chemokines, ligands, receptors, fluorescent dyes, photosensitizers, procoagulant factors, anti-coagulant factors, enzymes for prodrug activation, and radionuclides. There are a multitude of other pharmaceutically and/or diagnostically active components that are known to one skilled in the art, and the present invention is not limited to the representative examples listed here.

In another embodiment the invention relates to a fusion protein comprising one or more scaffolds of the invention fused to a component modulating serum half-life, for example, but not limited to polyethylene glycol (PEG), immunoglobulin, and albumin binding peptides. One who is skilled in the art may select additional large molecules or binding domains suitable as fusion partners which are also suitable for the purpose of extending serum half-life.

In a specific embodiment of the invention, the recombinant proteins comprising the scaffolds of the invention essentially do not elicit an immunogenic reaction in mammals, such as, for example, mouse, rat, monkey or human. Thus an embodiment of the invention relates to the generation of derivatives of the scaffold of the invention having reduced immunogenicity. Of course, the immunogenicity of derivatives of the scaffold of the invention will not only depend on the scaffold derived portions, but also the randomized regions and other portions of the fusion protein. A variety of software and databases are available for in silico prediction of peptide binding to MHC molecules, and one who is skilled in the art could use such software or databases as an aid to generate derivatives of recombinant scaffolds of the invention, and also fusion constructs comprising recombinant scaffolds of the invention with reduced immunogenicity risk. In one specific embodiment, by searching a freely available database of peptides predicted to bind to MHC class II molecules, it was found that the protein comprising the wildtype *Thermotoga maritima* CheB$_c$ domain (SEQ ID NO: 80) contains a number of potential T-cell epitopes. By repeated interrogation of the database with CheB$_c$ domain sequence variants, it was found that modifying SEQ ID NO: 80 by incorporating the amino acid residue substitutions Met53Gln and Ser125Glu would enable the predicted immunogenicity of the scaffold of the invention to be reduced. It would be trivial for one skilled in the art to generate a variety of other amino acid sequence variants to reduce the immunogenicity of the scaffold or of individual binding molecules. In other embodiments, standard techniques such as administering a recombinant protein of interest to a mammal and appropriately analyzing the immune response may be used to evaluate the immunogenicity risk of individual variants, and are well known to one skilled in the art.

In some embodiments, the scaffold of the invention comprises polypeptide sequence variants with improved developability. Such variants may include, for example, variants lacking cysteine residues, variants lacking predicted N-glycosylation sites, and variants with reduced predicted degradation risk, such as predicted deamidation, isomerization, oxidation, fragmentation, and aggregation. In one specific embodiment, modifying SEQ ID NO: 80 by incorporating the amino acid residue substitution Cys161Ser would enable the generation of a cysteine free scaffold. It would be trivial for one who is skilled in the art to generate additional scaffold sequence variants with improved qualities by using well known techniques. In other embodiments, it is expected that the library of the invention will generate highly stable and soluble target binding candidates, with high specificity and affinity, making them particularly well suited for therapeutic and/or diagnostic applications. Thus, a highly relevant embodiment of the invention relates to the use of a scaffold of the invention, or a fusion derivative thereof, for preparing a medicament or diagnostic tool.

In a specific embodiment, one or more scaffolds of the invention, or a fusion derivative thereof, is used for preparing a medicament or diagnostic means for the treatment or diagnosis of disease, in another specific embodiment, for the diagnosis or treatment of cancer, cardiovascular, infectious, or inflammatory disease.

In one specific embodiment, one or more scaffolds of the invention, or a fusion derivative thereof, is used for preparing a diagnostic means comprising a device utilizing surface plasmon resonance for detection of binding complexes, for the diagnosis of cancer, or cardiovascular, infectious, or inflammatory disease.

Another embodiment of the invention relates to a pharmaceutical or diagnostic composition comprising one or more scaffolds of the invention, or a fusion derivative thereof, and where suitable, a pharmaceutically acceptable excipient and/or carrier. A person skilled in the art will be able to select for suitable excipients and carriers from an abundant prior art and be able to determine their suitability using routine methods.

In another embodiment, in order to treat or to diagnose disease in a subject suspected of suffering from a disease, one or more scaffolds of the invention, or a fusion derivative thereof can be administered in a variety of forms or modes which makes the compound available in effective amounts. Numerous routes of administration are well known to one skilled in the art and include (but are not limited to) oral, subcutaneous, intramuscular, intravenous, intraperitoneal, intradermal, spinal, topical, intranasal, intraocular, and the like, and the most suitable can be easily selected based on such things as, for example pharmacokinetic data obtained from in vivo experiments, common medical practice, and other sources of knowledge extensively available to one skilled in the art. In some embodiments, NMR, PET, CT, fluorescent imaging, and a variety of other well known in vivo imaging techniques may be used for the diagnosis of disease using one or more scaffolds of the invention or derivatives thereof.

Another embodiment of the invention relates to co-administration or treatment with additional therapeutic agents, for example, a cytokine, steroid, chemotherapeutic agent, antibiotic, radiation or other therapeutic agents and treatments well known in the art. This is a well known means of enhancing the therapeutic effect of a drug. The appropriate dosage, combination, and timing of the additional therapies may be selected based on a variety of relevant factors known to one skilled in the art.

The invention also provides methods of detecting a compound by utilizing the scaffold of the invention. Based on the binding specificities of the scaffolds obtained by library screening, it is possible to use such scaffolds in assays to detect a specific target in a sample, such as for diagnostic methods. In one embodiment, the method of detecting a compound comprises contacting said compound in a sample with a scaffold of the invention, under conditions that allow a compound:scaffold complex to form and detecting said scaffold, thereby detecting said compound in a sample. In further embodiments, the scaffold is labeled (for example, radiolabel, fluorescent, enzyme-linked or colorimetric label) to facilitate the detection of said compound. In further embodiments, the use of in vivo implanted devices utilizing the scaffold of the invention or a derivative thereof may be used for detection of a compound of interest.

The invention also provides methods of capturing a compound utilizing the scaffold of the invention. Based on the binding specificities of the scaffolds obtained by library screening, it is possible to use such scaffolds in assays to capture the specific target in a sample, such as for purification methods. In one embodiment, the method of capturing a compound in a sample comprises contacting said compound in a sample with a scaffold of the invention under conditions that allow the formation of a compound:scaffold complex and removing said complex from the sample, thereby capturing said compound in said sample. In further embodiments, the scaffold is immobilized to facilitate the removing of the compound:scaffold complex.

Those skilled in the art will recognize, or be able to ascertain using no more than routine experimentation, many equivalents to the specific embodiments of the invention described herein. Such equivalents are intended to be encompassed by the invention described herein.

Exemplary Embodiments

1. A recombinant polypeptide scaffold comprising, a recombinant $CheB_c$ domain comprising:
  (i) fourteen loop regions corresponding to the cognate loop regions of SEQ ID NO: 1, the cognate loop regions of SEQ ID NO: 1 consisting of residues:
    (a) from 16 to 18 inclusive;
    (b) from 29 to 37 inclusive;
    (c) from 43 to 47 inclusive;
    (d) from 60 to 61 inclusive;
    (e) from 66 to 75 inclusive;
    (f) from 80 to 84 inclusive;
    (g) from 92 to 93 inclusive;
    (h) from 103 to 107 inclusive;
    (i) from 124 to 125 inclusive;
    (j) from 135 to 137 inclusive;
    (k) from 149 to 150 inclusive;
    (l) from 160 to 162 inclusive;
    (m) from 173 to 176 inclusive;
    (n) from 180 to 181 inclusive,
  (ii) linked to secondary structural elements corresponding to the non-loop regions of SEQ ID NO: 1 and;
  wherein at least one of said loop regions is a non-naturally occurring variant of the cognate loop region of SEQ ID NO: 1, and;
  having at least 50%, at least 60%, at least 70%, at least 75%, at least 80%, at least 90%, at least 95%, or at least 99% amino acid sequence identity outside the non-naturally occurring variant loop regions to SEQ ID NO: 1.

2. The scaffold of embodiment 1, comprising, a linear sequence of four framework regions FR1 (SEQ ID NO: 40), FR2 (SEQ ID NO: 41), FR3 (SEQ ID NO: 42), and FR4 (SEQ ID NO: 43), wherein the framework regions have at least 50%, at least 60%, at least 70%, at least 75%, at least 80%, at least 90%, at least 95%, or at least 99% amino acid sequence identity to the cognate regions of SEQ ID NO: 1; connected by loop regions, wherein at least one loop regions is a non-naturally occurring variant of the cognate loop region of SEQ ID NO: 1.

3. The scaffold of embodiment 2, comprising, four framework regions FR1 (SEQ ID NO: 40), FR2 (SEQ ID NO: 41), FR3 (SEQ ID NO: 42), and FR4 (SEQ ID NO: 43), wherein the framework regions have at least 50%, at least 60%, at least 70%, at least 75%, at least 80%, at least 90%, at least 95%, or at least 99% amino acid sequence identity to the cognate regions of SEQ ID NO: 1; and three loop regions L1 (SEQ ID NO: 44), L2 (SEQ ID NO: 44), and L3 (SEQ ID NO: 47) wherein Xaa represents any amino acid; and wherein L1 is linked between FR1 and FR2, L2 is linked between FR2 and FR3, and L3 is linked between FR3 and FR4 to form a contiguous polypeptide comprising the arrangement FR1–L1–FR2–L2–FR3–L3–FR4.

4. The scaffold of embodiment 2, comprising, four framework regions FR1 (SEQ ID NO: 40), FR2 (SEQ ID NO: 41), FR3 (SEQ ID NO: 42), and FR4 (SEQ ID NO: 43), wherein the framework regions have at least 50%, at least 60%, at least 70%, at least 75%, at least 80%, at least 90%, at least 95%, or at least 99% amino acid sequence identity to the cognate regions of SEQ ID NO: 1; and three loop regions L1 (SEQ ID NO: 45), L2 (SEQ ID NO: 46), and L3 (SEQ ID NO: 47) wherein Xaa represents any amino acid, and wherein L1 is linked between FR1 and FR2, L2 is linked between FR2 and FR3, and L3 is linked between FR3 and FR4 to form a contiguous polypeptide comprising the arrangement FR1–L1–FR2–L2–FR3–L3–FR4.

5. The scaffold of embodiment 3, wherein for the L1, L2 and L3 loop regions Xaa represents serine, aspartic acid, arginine, alanine, leucine, threonine, asparagine, tryptophan, glycine, glutamic acid, valine and tyrosine.

6. The scaffold of embodiment 4, wherein for the L1 and L2 loop regions Xaa represents any amino acid, and; wherein for the L3 loop region Xaa represents serine, aspartic acid, arginine, alanine, leucine, threonine, asparagine, tryptophan, glycine, glutamic acid, valine and tyrosine.

7. A polynucleotide encoding the scaffold of embodiment 1.

8. A cell that has been genetically engineered to express the polynucleotide of embodiment 7.

9. The scaffold of embodiment 1, further comprising a fluorophore, a radioisotope, a drug conjugate, an enzyme, a serum half-life extending polypeptide, or a target-binding polypeptide.

10. The scaffold of embodiment 9, further comprising a linker having one or more glycine residues that connects the scaffold to the fluorophore, the radioisotope, the drug conjugate, the enzyme, the serum half-life extending polypeptide, or the target-binding polypeptide.

11. The scaffold of embodiment 1, wherein the scaffold is capable of binding to a target other than that bound by an additional target-binding polypeptide.

12. The scaffold of embodiment 11, wherein the target-binding polypeptide is a polyhistidine tag.

13. The scaffold of embodiment 11, wherein the target-binding polypeptide is a FLAG tag.

14. A target detection device comprising the scaffold of embodiment 1.

15. A composition comprising the scaffold of embodiment 1 and a pharmaceutically acceptable carrier.

16. A scaffold of any of embodiments 1-6 which has been determined to bind a target.

17. A scaffold of any of embodiments 1-6 wherein said scaffold has been determined to bind a target with an affinity ($K_D$) of at least 100 μM.

18. The scaffold of embodiment 17, wherein said target is a cell-surface antigen, a soluble antigen, an immobilized antigen, an immunosilent antigen, an intracellular antigen, an intranuclear antigen, a self antigen, a non-self antigen, a cancer antigen, a bacterial antigen, or a viral antigen.

19. The scaffold of embodiment 17, wherein said scaffold exhibits a thermal melting temperature (Tm) of at least 40° C.

20. The scaffold of embodiment 17, wherein said scaffold is conjugated to a heterologous agent, wherein said agent is selected from the group consisting of polyethylene glycol (PEG), human serum albumin (HSA), an Fc region of an antibody, an IgG molecule, cytotoxic drug, imaging agent, toxin, biotin, nucleic acid, or a cytokine.

21. A multidomain construct comprising the scaffold of embodiment 17, wherein said multidomain construct further comprises an epitope binding domain, wherein said epitope binding domain is selected from the group consisting of an additional scaffold of embodiment 17, a scaffold unrelated to embodiment 17, an antibody, an antibody fragment, a diabody, an scFv, a Fab, an Fv, or a binding peptide.

22. The multidomain construct of embodiment 21, wherein said multidomain construct recognizes one epitope.

23. The multidomain construct of embodiment 21, wherein said multidomain construct recognizes two epitopes.

24. The multidomain construct of embodiment 21, wherein said multidomain construct recognizes three or more epitopes.

25. The multidomain construct of any of embodiments 21-24, wherein said scaffold is linked to said epitope binding domain by an IgG molecule or fragment thereof, an Fc region, a dimerization domain, a disulfide bond, or an amino acid linker.

26. The multidomain construct of any of embodiments 21-24, wherein said scaffold is covalently joined to said epitope binding domain by enzymatic or chemical reaction.

27. The multidomain construct of any of embodiment 25-26, further comprising a fluorophore, a radio isotope, a drug conjugate, an enzyme, or a serum half-life extending polypeptide.

28. An isolated nucleic acid molecule encoding the multidomain construct of any of embodiments 21-25.

29. The nucleic acid of embodiment 28 operably linked to an expression vector.

30. A host cell comprising the construct of embodiment 29.

31. A polypeptide display library comprising a plurality of variant scaffolds of any of embodiment 1-6.

32. A collection of isolated nucleic acid molecules encoding the library of embodiment 31.

33. The nucleic acid molecules of embodiment 32 operably linked to an expression vector.

34. A method of obtaining a polypeptide scaffold that binds to a target, said method comprising (a) contact to a target ligand with the library of any of the embodiments of 1-6 under conditions that allow a scaffold:target ligand complex to form, and (b) obtaining from the complex, the scaffold that binds to the target ligand.

35. The method of embodiment 34, further comprising randomizing at least one loop region of said scaffold of step (b) to generate a further randomized scaffold and repeating steps (a) and (b) using said further randomized scaffold.

36. The method of embodiment 34, further comprising randomizing at least one non-loop region of said scaffold of step (b) to generate a further randomized scaffold and repeating steps (a) and (b) using said further randomized scaffold.

37. A method of detecting a compound in a sample, said method comprising contacting said sample with a scaffold of any of embodiments 16-20 under conditions that allow the formation of a compound:scaffold complex and detecting said complex, thereby detecting said compound in said sample.

38. A method of capturing a compound in a sample, said method comprising contacting said sample with an immobilized scaffold of any of embodiments 16-20 under conditions that allow the formation of a compound:scaffold complex and removing said immobilized scaffold, thereby capturing said compound in said sample.

39. A method of detecting a compound in a sample, said method comprising contacting said sample with a multidomain construct of any of embodiments 21-27 under conditions that allow the formation of a compound: multidomain construct complex and detecting said complex, thereby detecting said compound in said sample.

40. A method of capturing a compound in a sample, said method comprising contacting said sample with an immobilized multidomain construct of any of embodiments 21-27 under conditions that allow the formation of a compound: multidomain construct complex and removing said immobilized multidomain construct, thereby capturing said compound in said sample.

41. A sterile, pyrogen-free composition comprising the scaffold of any embodiments 16-20 or the multidomain construct of any embodiments 21-27.

42. A pharmaceutical composition comprising embodiment 41.

43. A method of preventing, treating, managing or ameliorating a disease in a patient with the composition of embodiment 41 or 42.

44. A method of diagnosing or imaging a disease in a patient with the composition of embodiment 41 or 42.

45. The method of embodiment 43, wherein said method further comprises an additional therapy, wherein said therapy is immunotherapy, biological therapy, chemotherapy, radiation therapy, or small molecule drug therapy.

46. The method of any of embodiments 43-45 wherein said disease is an autoimmune disease, inflammatory disease, proliferative disease, infectious disease, respiratory disease, cardiovascular disease, degenerative disease, or metabolic disease.

47. A recombinant, non-naturally occurring polypeptide scaffold comprising, a recombinant $CheB_c$ domain, having at least 50%, at least 60%, at least 70%, at least 75%, at least 80%, at least 90%, at least 95%, or at least 99% amino acid sequence identity outside the loop regions to SEQ ID NO: 1; and wherein at least one of said loop regions vary by deletion, substitution or addition by at least one amino acid from the corresponding loop regions of SEQ ID NO: 1.

48. The scaffold of embodiment 47, wherein said scaffold comprises two loop region sequences that vary by deletion, substitution or addition by at least one amino acid from the corresponding loop regions of SEQ ID NO: 1.

49. The scaffold of embodiment 47, wherein said scaffold comprises three loop region sequences that vary by deletion, substitution or addition by at least one amino acid from the corresponding loop regions of SEQ ID NO: 1.

50. The scaffold of embodiment 47, wherein said scaffold comprises four loop region sequences that vary by deletion, substitution or addition by at least one amino acid from the corresponding loop regions of SEQ ID NO: 1.

51. The scaffold of embodiment 47, wherein said scaffold comprises five loop region sequences that vary by deletion, substitution or addition by at least one amino acid from the corresponding loop regions of SEQ ID NO: 1.

52. The scaffold of embodiment 47, wherein said scaffold comprises six loop region sequences that vary by deletion, substitution or addition by at least one amino acid from the corresponding loop regions of SEQ ID NO: 1.

53. The scaffold of embodiment 47, wherein said scaffold comprises seven loop region sequences that vary by deletion, substitution or addition by at least one amino acid from the corresponding loop regions of SEQ ID NO: 1.

54. The scaffold of embodiment 47, wherein said scaffold comprises eight or more loop region sequences that vary by deletion, substitution or addition by at least one amino acid from the corresponding loop regions of SEQ ID NO: 1.

55. A polypeptide display library comprising a plurality of variant scaffolds of any of embodiment 47-54.

56. A collection of isolated nucleic acid molecules encoding the library of embodiment 55.

57. The nucleic acid molecules of embodiment 56 operably linked to an expression vector.

58. A scaffold of any of embodiments 47-54 which has been determined to bind a target.

59. A scaffold of any of embodiments 47-54 which has been determined to bind a target with an affinity ($K_D$) of at least 100 µM.

60. The scaffold of embodiment 59, wherein said target is a cell-surface antigen, a soluble antigen, an immobilized antigen, an immunosilent antigen, an intracellular antigen, an intranuclear antigen, a self antigen, a non-self antigen, a cancer antigen, a bacterial antigen, or a viral antigen.

61. The scaffold of embodiment 59, wherein said scaffold exhibits a thermal melting temperature (Tm) of at least 40° C.

62. The scaffold of embodiment 59, wherein said scaffold is conjugated to a heterologous agent, wherein said agent is selected from the group consisting of polyethylene glycol (PEG), human serum albumin (HSA), an Fc region of an antibody, an IgG molecule, cytotoxic drug, imaging agent, toxin, biotin, nucleic acid, or a cytokine.

63. A multidomain construct comprising the scaffold of embodiment 59, wherein said multidomain construct further comprises an epitope binding domain, wherein said epitope binding domain is selected from the group consisting of an additional scaffold of embodiment 59, a scaffold unrelated to embodiment 59, an antibody, an antibody fragment, a diabody, an scFv, a Fab, an Fv, or a binding peptide.

64. The multidomain construct of embodiment 63, wherein said multidomain construct recognizes one epitope.

65. The multidomain construct of embodiment 63, wherein said multidomain construct recognizes two epitopes.

66. The multidomain construct of embodiment 63, wherein said multidomain construct recognizes three or more epitopes.

67. The multidomain construct of any of embodiments 63-66, wherein said scaffold is linked to said epitope binding domain by an IgG molecule or fragment thereof, an Fc region, a dimerization domain, a disulfide bond, or an amino acid linker.

68. The multidomain construct of any of embodiments 60-63, wherein said scaffold is covalently joined to said epitope binding domain by enzymatic or chemical reaction.

69. The multidomain construct of any of embodiment 67-68, further comprising a fluorophore, a radioisotope, a drug conjugate, an enzyme, or a serum half-life extending polypeptide.

70. An isolated nucleic acid molecule encoding the multidomain construct of any of embodiments 63-67.

71. The nucleic acid of embodiment 70 operably linked to an expression vector.

72. A host cell comprising the construct of embodiment 71.

73. A method of detecting a compound in a sample, said method comprising contacting said sample with a scaffold of any of embodiments 58-62 under conditions that allow the formation of a compound:scaffold complex and detecting said complex, thereby detecting said compound in said sample.

74. A method of capturing a compound in a sample, said method comprising contacting said sample with an immobilized scaffold of any of embodiments 58-62 under conditions that allow the formation of a compound:scaffold complex and removing said immobilized scaffold, thereby capturing said compound in said sample.

75. A method of detecting a compound in a sample, said method comprising contacting said sample with a multidomain construct of any of embodiments 63-69 under conditions that allow the formation of a compound: multidomain construct complex and detecting said complex, thereby detecting said compound in said sample.

76. A method of capturing a compound in a sample, said method comprising contacting said sample with an immobilized multidomain construct of any of embodiments 63-69 under conditions that allow the formation of a compound: multidomain construct complex and removing said immobilized multidomain construct, thereby capturing said compound in said sample.

77. A sterile, pyrogen-free composition comprising the scaffold of any embodiments 58-62 or the multidomain construct of any of embodiments 63-69

78. A pharmaceutical composition comprising embodiment 77.

79. A method of preventing, treating, managing or ameliorating a disease in a patient with the composition of embodiment 77 or 78.

80. A method of diagnosing or imaging a disease in a patient with the composition of embodiment 77 or 78.

81. The method of embodiment 79, wherein said method further comprises an additional therapy, wherein said therapy is immunotherapy, biological therapy, chemotherapy, radiation therapy, or small molecule drug therapy.

82. The method of any of embodiments 79-81 wherein said disease is an autoimmune disease, inflammatory disease, proliferative disease, infectious disease, respiratory disease, cardiovascular disease, degenerative disease, or metabolic disease.

The invention is further illustrated by the following examples and attached drawings and sequence information.

EXAMPLES

The invention is now described with reference to the following examples. These examples are provided for the purpose of illustration only and the invention should in no way be construed as being limited to these examples but rather should be construed to encompass any and all variations which become as a result of the teachings provided herein.

Example 1

Randomization Design of the Scaffold of the Invention

Optimization of the Polypeptide Sequence of the Scaffold of the Invention

It is desirable that the scaffold of the invention essentially does not elicit an immunogenic reaction in mammals, including for example in humans. The polypeptide sequence of a protein structure comprising the wildtype CheB$_c$ domain of *Thermotoga maritima* (PDB ID: 3SFT) (SEQ ID NO: 80) was screened against a database of peptides predicted to bind to MHC-II molecules DRB1_0101, DRB1_0301, DRB1_0401, DRB1_0701, DRB1_0802, DRB1_1101, DRB1_1302, and DRB1_1501 (Jensen K. et. al, 2018). After identification of peptides within the top 5% rank threshold for binding, repeated interrogation of the database with CheB$_c$ domain sequence variants was performed to identify variants with reduced predicted immunogenic potential. It was found that performing the amino acid residue substitutions Met53Gln and Ser125Glu on SEQ ID NO: 80 would enable the predicted binding of the scaffold of the invention to MHC-II molecules to be reduced. An additional Cys161Ser substitution was performed on the above sequence to enable the generation of a cysteine free scaffold. The result of these three amino acid residue substitutions were incorporated into the polypeptide SEQ ID NO: 1.

Generation of recombinant test loop graft constructs of the scaffold of the invention Analysis of published structural data of a protein comprising the wildtype CheB$_c$ domain of *Thermotoga maritima* (PDB ID: 3SFT) (SEQ ID NO: 80) (FIG. 1) enabled the identification of a variety of loop regions. Three of these loop regions were selected for test loop grafting, to evaluate the tolerance of the CheB$_c$ domain to randomization. The positions selected for test loop grafting on SEQ ID NO: 1 are shown in FIG. 5.

A polynucleotide comprising the coding region of SEQ ID NO: 1 was designed with flanking EcoRI and AscI restriction enzyme sites to generate a synthetic DNA (SEQ ID NO: 7), encoding the corresponding polypeptide SEQ ID NO: 4. This synthetic DNA (SEQ ID NO: 7) was obtained from FASMAC (Japan) and used as a PCR template.

Figure 10:
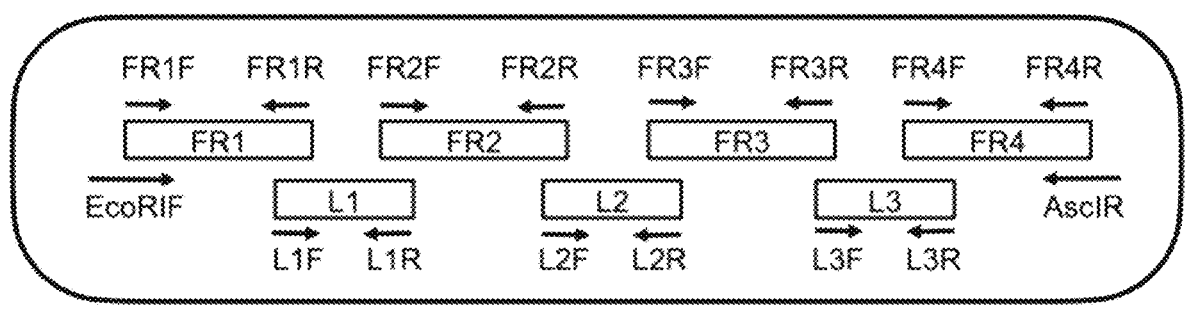
FIG. 10. A diagrammatic representation of the primers and DNA fragments used to generate the assembled DNA fragments comprising the coding region of the randomized library of the scaffold of the invention. The arrows in the figure represent the annealing positions and orientation of the PCR primers listed in Table 1 used for amplifying and assembling the individual DNA fragments. The rectangles in the figure represent the DNA fragments, the labels inside the rectangles represent the identities of the framework and loop comprising polypeptide regions encoded by the respective DNA fragments. The overlapping regions of the rectangles represent the overlapping complimentary nucleotide sequences which enable joining of the DNA fragments by PCR. The external primers EcoRIF and AscIR contain restriction enzyme sites for EcoRI and AscI respectively.
Figure 11:
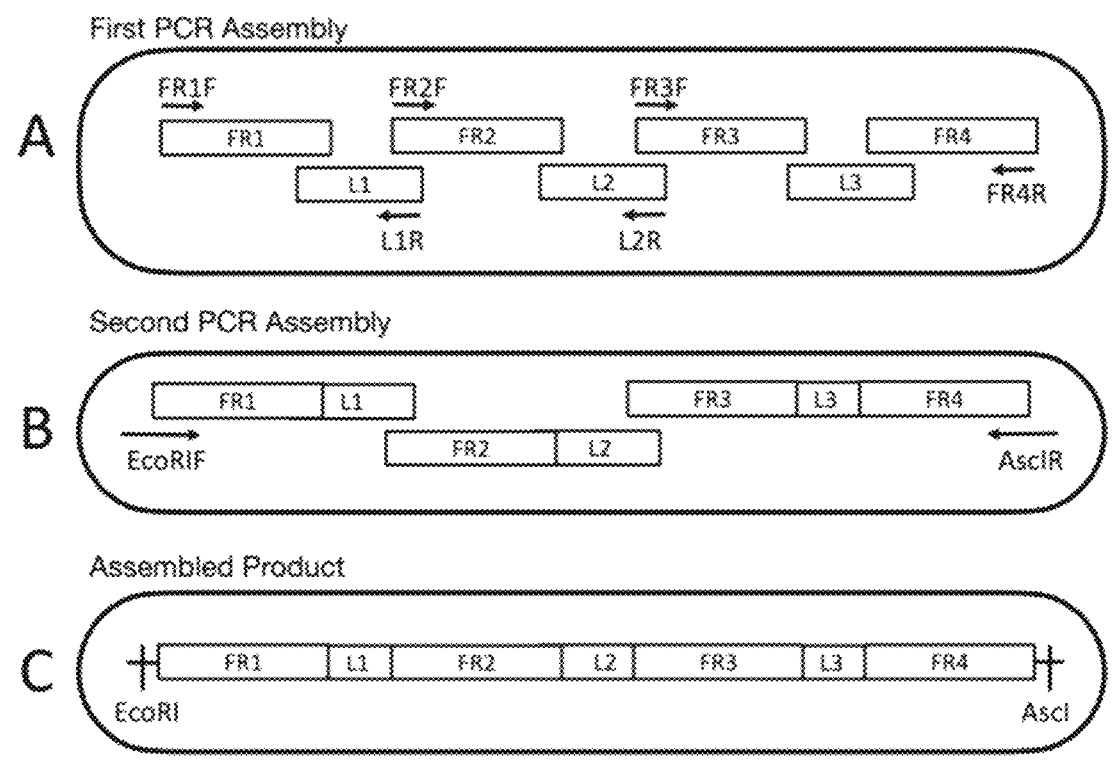
FIG. 11. A diagrammatic representation of the overlapping extension PCR assembly of the DNA fragments comprising the sequences encoding the frameworks and loop regions of the randomized library of the scaffold of the invention. The arrows in the figure represent the annealing positions and orientation of the PCR primers listed in Table 1 used for amplifying and assembling the individual DNA fragments. The rectangles in the figure represent the DNA fragments, the labels inside the rectangles represent the identities of the framework and loop comprising polypeptide regions encoded by the respective DNA fragments. The overlapping regions of the rectangles represent the overlapping complimentary nucleotide sequences which enable joining of the DNA fragments by PCR. The external primers EcoRIF and AscIR contain restriction enzyme sites for EcoRI and AscI respectively. (A) A representation of the First PCR assembly of the DNA fragments comprising the coding regions for FR1+L1, FR2+L2, and FR3+L3+FR4. (B) A representation of the Second PCR Assembly showing the subsequent assembly of the DNA fragments comprising the coding regions for FR1–L1+FR2–L2+FR3–L3–FR4. (C) A representation of the Assembled Product showing the resultant DNA fragments comprising the coding region of the randomized scaffold library.

The DNA fragments encoding the framework regions of the scaffold of the invention FR1 (SEQ ID NO: 81), FR2 (SEQ ID NO: 82), FR3 (SEQ ID NO: 83), and FR4 (SEQ ID NO: 84), were amplified from DNA SEQ ID NO: 7 by PCR using the appropriate flanking primers shown on the scheme of FIG. 10, and listed in Table 1. For each framework fragment encoding DNA to be amplified, PCR amplifications were carried out using 100 fmol of DNA template per 50 µl reaction. PCR reactions were carried out using Pfu Ultra II Fusion HS DNA polymerase (Agilent) according to the manufacturer's instructions at 55° C. annealing temperature for 20 cycles.

Synthetic oligonucleotides comprising the coding regions for test loop graft 1 (SEQ ID NO: 37), test loop graft 2 (SEQ ID NO: 38), and test loop graft 3 (SEQ ID NO: 39) were obtained from FASMAC (Japan). These were assembled with the gel purified DNA fragments encoding the framework regions, to generate DNA fragments encoding the test loop graft constructs of the scaffold of the invention, with test loop grafts in positions 2 and 3 (SEQ ID NO: 12), test loop grafts in positions 1 and 2 (SEQ ID NO: 13), test loop grafts in positions 1 and 3 (SEQ ID NO: 14), and test loop grafts in positions 1 and 2 and 3 (SEQ ID NO: 15) (the respective polypeptide sequences alignment is represented in FIG. 6). Assembly of neighbouring DNA fragments by sequential rounds of overlap extension PCR reactions was carried out, using 100 fmol of each DNA species per 50 µl reaction. PCR products were gel purified between each amplification step and used as templates for the next overlap extension PCR assembly round until full length products were obtained. The final step of overlap extension PCR used primers EcoRIF and AscIR (Table 1) to append EcoRI and AscI restriction sites to the assembled products. PCR products were gel purified, and digested with a 20 fold excess of EcoRI-HF and AscI (New England Biolabs) for 3 hours at 370C before column purifying the digested DNA with a Wizard SV gel and PCR Clean-Up System (Promega). The resultant DNA inserts were cloned into a modified pQE-80L vector (QIAGEN) comprising corresponding EcoRI and AscI cloning sites, and transformed into *E. coli* XL1-Blue (Agilent). Isolated plasmid clones were sequenced and clones encoding polypeptides comprising the recombinant test loop graft constructs of the scaffold of the invention with test loop grafts in positions 2 and 3 (SEQ ID NO: 8), test loop grafts in positions 1 and 2 (SEQ ID NO: 9), test loop grafts in positions 1 and 3 (SEQ ID NO: 10), and test loop grafts in positions 1 and 2 and 3 (SEQ ID NO: 11) were identified.

Expression and Purification of Recombinant Test Loop Graft Constructs of the Scaffold of the Invention Glycerol stocks of sequence verified clones were used to inoculate 50 mL cultures of 2×YT medium containing 50 µg/mL kanamycin and 0.1% glucose and grown at 37° C. with vigorous shaking until $OD_{600}$ reached 0.5. Then cultures were chilled on ice and IPTG added to 0.5 mM and cultures allowed to grow overnight at 27° C. with vigorous shaking. Cultures were centrifuged at 3000×g for 10 minutes at 4° C. and the cell pellets were resuspended in 27 mL of ice cold PBS (pH 7.4) containing 300 mM NaCl. Then 3 mL of 10×bugbuster reagent (EMD Millipore) was added and the cells allowed to lyse on ice for 30 minutes. The cell lysates were then centrifuged at 12,000×g for 30 minutes at 4° C. and the supernatants containing the cell lysates were recovered. These were then allowed to bind to a 1 mL bed volume of pre-equilibrated Talon Cell-thru resin (Clontech) and the purification was continued according to the manufacturer's instructions and eluted in a 5 mL volume. Purified proteins were visualized by running 10 µl aliquots on NuPAGE 4-12% SDS-PAGE gels (Invitrogen) and staining with Coomassie blue stain (FIG. 7). The eluted proteins were buffer exchanged for PBS (pH 7.4) by repeated centrifugation through Amicon Ultra-4 10,000 MWCO columns (Millipore) according to the manufacturer's instructions, and proteins were recovered in an approximately 1 mL volume. Protein concentrations were calculated based on measured absorbance at 280 nm compared to extinction coefficients predicted from amino acid sequences deduced from DNA sequence data. Post purification yields for the test proteins are reported in Table 2.

Thermostability of Recombinant Test Loop Graft Constructs of the Scaffold of the Invention Thermostability of the purified proteins comprising the recombinant test loop graft constructs of the scaffold of the invention was determined by DSF (differential scanning fluorimetry) measurements with SYPRO orange dye (Merck) with proteins at 500 µg/mL in PBS buffer (pH 7.4) at a scanning rate of 0.5° C./min (FIG. 9). The melting temperature of the proteins were determined from the temperatures at the maxima of the first derivative curves of fluorescence intensity. The melting temperature of the proteins are reported in Table 2. For all of the recombinant test loop graft constructs of the scaffold of the invention evaluated, a melting temperature of around 90° C. was observed, and only a few degrees difference in thermostability was observed between the different test constructs (Tm range 89.4-92.0° C.). This suggests the scaffold of the invention may be capable of supporting a variety of more extensive modifications than the test loop graft combinations evaluated here, and that one skilled in the art and being aware of these findings could, by means of routine experimentation, have a reasonable expectation of success in generating and utilizing such variants.

Determination of Monomeric Fraction

The monomeric fraction of the purified protein comprising the test loop graft construct of the scaffold of the invention with test loop grafts in positions 1 and 2 and 3 (SEQ. ID NO. 11) was determined by size exclusion chromatography after storage at 1 mg/mL in PBS buffer (pH 7.4) at 4° C. for 2 weeks, followed by room temperature storage for 2 weeks. SEC was carried out on a Superdex 75 10/300 column (GE Lifesciences) with 500 µg of protein in PBS buffer (pH 7.4) (FIG. 8). The purified protein was found to be 96.4% monomeric. The experimentally determined monomeric mass was 22.6 kDa which is in close agreement with the predicted molecular weight of approximately 24 kDa.

Example 2

Construction of a Randomized Library of Scaffolds of the Invention

The DNA fragments SEQ ID NO: 81, SEQ ID NO: 82, SEQ ID NO: 83, and SEQ ID NO: 84, encoding the framework regions FR1 (SEQ ID NO: 40), FR2 (SEQ ID NO: 41), FR3 (SEQ ID NO: 42), and FR4 (SEQ ID NO: 43) respectively, were amplified from DNA SEQ ID NO: 7 by PCR using the appropriate flanking primers shown on the scheme of FIG. 10, and listed in Table 1. For each framework region encoding DNA to be amplified, 8 individual PCR amplifications were carried out using 100 fmol of DNA template per 50 µl reaction. PCR reactions were carried out using Phusion Hot Start Flex DNA polymerase (New England Biolabs) according to the manufacturer's instructions at 72° C. annealing temperature for 20 cycles. PCR products were gel purified using the Wizard SV Gel and PCR Clean-Up System (Promega).

Trinucleotide coupled oligonucleotides SEQ ID NO: 16, SEQ ID NO: 17, and SEQ ID NO: 18, comprising DNA sequences encoding the trinucleotide randomized loop regions L1 (SEQ ID NO: 44), L2 (SEQ ID NO: 44) and L3 (SEQ ID NO: 47), respectively, (FIG. 10) were obtained from ELLA Biotech GmbH (Germany). These were dissolved in TE buffer (10 mM Tris, 5 mM EDTA pH 8.0) to 50 µM.

The first stage of assembly of randomized loop region encoding DNA fragments to framework DNA encoding fragments (First PCR Assembly) was carried out by overlap extension PCR, using the appropriate primers listed in Table 1. Three separate PCR assembly schemes were carried out to assemble DNA fragments, comprising the coding regions of FR1+L1 (using primers FR1F and L1R) to generate the FR1-L1 encoding fragments, comprising the coding regions of FR2+L2 (using primers FR2F and L2R) to generate the FR2-L2 encoding fragments, and comprising the coding regions of FR3+L3+FR4 (using primers FR3F and FR4R) to generate the FR3-L3-FR4 encoding fragments, as diagrammatically represented in FIG. 11. In total, 5 replicate 100 µl PCR reactions were carried out for each scheme, each containing 500 fmoles of randomized loop fragment DNA templates. PCR was carried out using Phusion Hot Start Flex DNA polymerase (New England Biolabs) for 18 cycles at 72° C. annealing temperature. The individual fragment assemblies were gel purified as above.

The final assembly of the above fragments into the full length randomized library encoding DNA fragments comprising the coding region of FR1-L1-FR2-L2-FR3-L3-FR4, containing three trinucleotide coupled randomized loop regions (Second PCR Assembly) was carried out by overlap extension PCR with 125 fmoles of each fragment assemblies above per 50 µl PCR reaction tube, using external primers EcoRIF and AscIR (Table 1). In total, 176 PCR reaction tubes were used to amplify the full length fragment assembly for 20 cycles at 72° C. annealing temperature.

Generation of full length randomized library encoding DNA fragments comprising NNK randomized encoded loop regions was carried out as follows. Oligonucleotides SEQ ID NO: 19 and SEQ ID NO: 20, comprising DNA sequences encoding the NNK randomized loop regions L1 (SEQ ID NO: 45) and L2 (SEQ ID NO: 46), respectively, were obtained from FASMAC (Japan). The trinucleotide coupled oligonucleotide SEQ ID NO: 18, comprising DNA sequences encoding the trinucleotide randomized loop region L3 (SEQ ID NO: 47) was obtained from ELLA Biotech GmbH (Germany).

Assembly of randomized loop region encoding DNA fragments to framework DNA encoding fragments was carried out as above, except the final assembly of the fragments into the full length randomized library encoding DNA fragment (Second PCR Assembly) was carried out by overlap extension PCR with 125 fmoles of each assembled fragment per 50 µl PCR reaction tube, using external primers EcoRIF and AscIR (Table 1). In total, 112 PCR reaction tubes were used to amplify the full length fragment assembly for 20 cycles at 72° C. annealing temperature.

The PCR products corresponding to the full length randomized library encoding DNA fragments containing three trinucleotide coupled randomized loop regions, and the full length randomized library encoding DNA fragments containing NNK randomized loop regions were individually gel purified as above. These two libraries were subsequently cloned and displayed on phage separately.

In total, 72 µg of gel purified full length randomized library encoding DNA fragments containing three trinucleotide coupled randomized loop encoding regions were digested with 1400 U each of EcoRI-HF and AscI (New England Biolabs) in a 2.4 mL volume for 7 hours at 37° C. to generate library inserts for ligation. Also, 48 µg of gel purified full length randomized library encoding DNA fragments containing NNK randomized loop encoding regions were digested with 960 U each of EcoRI-HF and AscI (New England Biolabs) in a 1.6 mL volume for 7 hours at 37° C. to generate library inserts for ligation. The resultant digested insert DNAs were then separately column purified using the Wizard SV gel and PCR Clean-Up System (Promega).

A modified pADL-10b phagemid vector (Antibody Design Labs) comprising EcoRI and AscI restriction enzyme sites was used for the construction of the library and the generation of fusions of the scaffold of the invention with the phage pIII protein for display on phage particles. A one mg aliquot of this vector was digested in a 4 mL volume with 3000 U each of EcoRI-HF and AscI (New England Biolabs) at 37° C. for 3 hours to generate digested vector DNA for ligation. The DNA fragment corresponding to digested vector DNA was gel purified as described above.

Individual ligations were set up with 15.5 µg of digested vector and 5 µg digested insert described above (a roughly 2:1 molar ratio of insert:vector) in a 2.5 mL volume with 10,000 U of T4 DNA ligase (New England Biolabs) at 16° C. overnight. Ligations were heated at 65° C. for 15 minutes and the ligation buffer was exchanged for milliQ ultrapure water by repetitive spinning and water replacement using an Amicon Ultra 30K MWCO column (Millipore).

ElectrocompetentE. coli strain XL1-Blue (Agilent) was prepared from 1 liter cultures vigorously grown in TB medium until $OD_{600}$ reached 0.8. The culture was rapidly chilled on ice and centrifuged at 3000×g at 4° C. and the cell pellet was collected. The cell pellet was washed 3 times by repeatedly resuspending in ice cold milliQ ultrapure water and collection by centrifugation as above, and finally resuspended in a final volume of 9 mL of ice cold 10% glycerol. This was aliquoted into 1.5 mL volumes on ice and used for electroporation of the ligated DNA described above, using a total of 6 flatpack chamber 1.5 mL capacity electroporation cuvettes (Harvard Apparatus) shocked by a 1960 volt exponentially decaying pulse. The resultant transformed E. coli were grown for 1 hour in 250 mL of SOC medium at 37° C. and the harvested cell pellet was spread on a total of eight 500 cm² selective media plates containing TB agar, 2% glucose, and 100 µg/mL carbenicillin, and incubated at 37° C. for 16 hours. The resultant clones were harvested by scraping them from the plates with 2×YT medium containing 2% glucose, 100 µg/mL carbenicillin, and glycerol was added to a final volume of 15%. The resuspended cells were divided into 1 mL aliquots and stored at −80° C. as library E. coli glycerol stocks until further use. This process of ligation and transformation was repeated 13 times to generate a library of approximately $1.5 \times 10^{10}$ complexity for the DNA fragments encoding three trinucleotide coupled randomized loop regions, and $2.5 \times 10^9$ complexity for the DNA fragments encoding NNK randomized loop regions respectively, estimated from colony counts arising from diluted E. coli post electroporation culture aliquots.

Example 3

Phage Display of the Randomized Library of Scaffolds of the Invention

Aliquots of the E. coli glycerol stocks of the randomized library of scaffolds of the invention described above were thawed and diluted in a total of 5 liters of 2×YT medium (for the library containing three trinucleotide coupled randomized loop regions) and 1 liter of 2×YT medium (for the library containing NNK randomized loop regions) to give an $OD_{600}$ of 0.2. Carbenicillin and glucose were added to a final concentration of 100 g/mL carbenicillin and 0.1% (w/v) glucose. The cultures were then grown with vigorous shaking at 37° C. until the $OD_{600}$ reached 0.6 before infecting the E. coli by adding $2 \times 10^{12}$ VCSM13 helper phage (Agilent) per liter of culture. The infection was allowed to proceed for 1 hour at 37° C. before chilling the cultures on ice and adding kanamycin to 30 µg/mL. IPTG was also added to 0.5 mM to induce the expression of the scaffold-pIII fusion genes. The cultures were then grown overnight at 26° C.

The cultures were centrifuged at 8000×g at 4° C. for 20 minutes and the supernatants containing the phage particles was carefully recovered. These was chilled on ice and a 0.25× volume of 20% (w/v) PEG, 2.5 M NaCl was added and left on ice for 1 hour to precipitate the phage. The precipitate was centrifuged at 8000×g for 30 minutes at 4° C. and the phage pellets were washed by resuspending in PBS. These were then precipitated with 20% (w/v) PEG, 2.5 M NaCl as before and the phage pellets was washed again by resuspending in PBS. These was again precipitated and resuspended in PBS, and glycerol added to a final volume of 20%. Phage were then aliquoted into 0.6 mL volumes (for the library containing three trinucleotide coupled randomized loop regions) and 0.09 mL volumes (for the library containing NNK randomized loop regions) and stored at −80° C. as phage library stocks.

Example 4

Selection of Binders from the Scaffold Phage Display Library

First Round Phage Display Selection of the Library of the Scaffold of the Invention Against Targets PD-L1 and HER2

Biotinylated human PD-L1 antigen comprising a human IgG1 Fc domain, and biotinylated human HER2 antigen comprising a portion of the HER2 extracellular domain (Acro Biosystems) were individually used as panning targets as follows.

For each target, an aliquot of each of the two phage library stocks (containing three trinucleotide coupled randomized loop regions, and containing NNK randomized loop regions) were thawed and combined. Blocking reagents were added (BSA added to 3% (w/v) and Tween-20 added to 0.05% (v/v) in PBS) to give a final volume of 1 mL. For the PD-L1 target selection, non-biotinylated human IgG1 Fc protein (Acro Biosystems) was also added as a blocking reagent to 1000 µM final concentration. Then 200 µl aliquots of Dynal M-280 dynabeads suspension (Invitrogen) were washed twice in PBS containing 3% BSA, 0.05% Tween-20 and the blocked phage was added to the washed dynabeads and rotated at 4° C. for 1 hour to remove phage binding to the beads. The beads were then collected by magnet and the phage supernatant was transferred to a new tube. Biotinylated antigen was then added to the phage supernatant to a final concentration of 50 nM and the phage were allowed to bind to the antigen by rotating the mixture overnight at 4° C. Following this, 100 µl of dynabeads suspension was washed twice in PBS, 3% BSA, 0.05% Tween-20, and the supernatant discarded. The phage and antigen mixture was then added to the tube containing the washed dynabeads and the biotinylated antigen was captured on the dynabeads by rotating the mixture at 4° C. for 30 minutes. Following this, the dynabeads were collected by magnet to pull down the phage binding to the biotinylated antigen captured on the surface of the dynabeads, and the beads were washed 3 times with a 1 mL solution of PBS, 3% BSA, 0.05% Tween-20. The beads were then washed 3 times as above with PBS, 0.05% Tween-20, followed by 3 washes with PBS. The beads were then collected by magnet and the supernatant discarded, and bound phage were eluted by incubating the beads with 300 µl of 100 mM glycine, 500 mM NaCl, pH 2.2 for 10 minutes. The beads were then captured by magnet again and the supernatant containing the eluted phage was added to a 15 mL volume of $OD_{600}$=0.7 E. coli XL1-Blue in 2×YT medium. This was incubated at 37° C. for 45 minutes to allow the phage to infect the E. coli, and then the culture was centrifuged at 3000×g for 10 minutes at 4° C. The cell pellet was then resuspended in 2×YT medium and spread on a large 500 cm² selective media plate containing TB agar, 2% glucose, and 100 µg/mL ampicillin at 37° C. for 16 hours. Diluted aliquots of the infection output were also plated out as above to obtain colony counts which were used to estimate the number of clones obtained from the selection.

Approximately 4.8×10⁵ clones and 3.1×10⁵ clones were obtained from the PD-L1 and HER2 first round panning outputs respectively. The next day the colonies from each of the plates were harvested by scraping the plates with LB medium containing 1% glucose, 100 µg/mL ampicillin and 15% glycerol, and the resuspended cells were divided into 0.5 mL aliquots, and stored at −80° C. as first round panning selection output E. coli glycerol stocks until further use.

Randomization of the L1 and L3 Loops of the First Round Library Selection Outputs Randomization of the L1 loops and L3 loops for each selection output was carried out as follows. A pool of recombinant phagemid DNA was isolated from an aliquot of the first round panning selection output E. coli glycerol stocks described above by using a FastGene Plasmid Mini Kit (NIPPON Genetics, Japan). For the L1 loop randomization, primers FR2F and AscIR (Table 1), were used to amplify pools of first round selection output library DNA fragments without the L1 loop encoding region. For each pool of DNA fragments to be amplified, PCR amplifications were carried out using 8 fmol of DNA template in each of two 50 µl reactions. PCR amplifications were carried out using Phusion Hot Start Flex DNA polymerase (New England Biolabs) according to the manufacturer's instructions at 72° C. annealing temperature for 18 cycles. PCR products were gel purified using the Wizard SV Gel and PCR Clean-Up System (Promega). These fragments were joined by PCR to DNA fragments encoding FR1-L1 (FIG. 11) which were previously generated during library construction (Example 2), and contain the randomized loop 1 encoding region generated by trinucleotide coupling. Primers EcoRIF and AscIR (Table 1) were used to join the fragments in seven 50 µl PCR reactions for each target, each containing 125 fmol of each template, at 72° C. annealing temperature for 12 cycles. PCR products were gel purified as above. For the L3 loop randomization, primers EcoRIF and L2R (Table 1), were used to PCR amplify first round selection output library scaffold DNA without the L3 loop encoding region. For each pool of DNA fragments to be amplified, two individual PCR amplifications were carried out using 8 fmol of DNA template in in each of two 50 µl reactions. PCR amplifications were carried out using Phusion Hot Start Flex DNA polymerase (New England Biolabs) according to the manufacturer's instructions at 72° C. annealing temperature for 18 cycles. PCR products were gel purified using the Wizard SV Gel and PCR Clean-Up System (Promega).

These fragments were joined by PCR to DNA fragments encoding FR3-L3-FR4 (FIG. 11) which were previously generated during library construction (Example 2), and contain the randomized loop 3 encoding region generated by trinucleotide coupling. Primers EcoRIF and AscIR (Table 1) were used to join the fragments in seven 50 µl PCR reactions for each target, each containing 125 fmol of each template at 72° C. annealing temperature for 12 cycles. PCR products were gel purified as above. The PCR products comprising the resultant loop 1 and loop 3 randomized first round panning selection output encoding DNA pools were combined and 5 µg of this DNA was digested for 4 hours at 37° C. with 100 U each of EcoRI-HF and AscI (New England Biolabs). The digested DNA was then column purified using the Wizard SV gel and PCR Clean-Up System (Promega) to generate loop 1 and loop 3 randomized first round panning selection output insert DNA. Ligations were performed with 7.75 µg of the digested phagemid vector (used in library construction in Example 2) and 2.5 µg of loop 1 and loop 3 randomized first round panning selection output insert DNA described above (a roughly 2:1 molar ratio of insert:vector) in a 1.25 mL volume with 5,000 U of T4 DNA ligase (New England Biolabs) at 16° C. overnight. Ligations were heated at 65° C. for 10 minutes and the ligation buffer was exchanged for milliQ ultrapure water by repetitive spinning and water replacement using an Amicon Ultra 30K MWCO column (Millipore). These ligations were then each transformed into electrocompetent E. coli strain XL1-Blue (Agilent) and each transformation culture harvested and plated out on a large 500 cm² selective media plate containing TB agar, 2% glucose, and 100 µg/mL ampicillin at 37° C. for 16 hours using the procedure described for the library construction protocol (Example 2). A library of approximately 4×10⁸ complexity for the PD-L1 selection derived loop 1 and loop 3 randomized first round panning selection output encoding DNA, and 9×10⁷ complexity for the HER2 derived loop 1 and loop 3 randomized first round panning selection output encoding DNA were obtained, estimated from colony counts of diluted E. coli culture aliquots obtained after electroporation. The resultant clones were harvested by scraping them from the plates with 2×YT medium containing 2% glucose, 100 µg/mL carbenicillin, and glycerol was added to a final volume of 15%. The resuspended cells were divided into 1 mL aliquots and stored at −80° C. as randomized first round panning selection output E. coli glycerol stocks until further use.

Second and third rounds of phage display selection against targets PD-L1 and HER2 Aliquots of each of the E. coli glycerol stocks of the randomized first round panning selection outputs were thawed and diluted in 500 mL of 2×YT medium to give an $OD_{600}$ of 0.2. Also, aliquots of the first round panning selection output E. coli glycerol stocks were thawed and diluted in 100 mL of 2×YT medium to give an $OD_{600}$ of 0.2. To each culture, carbenicillin and glucose were added to a final concentration of 100 µg/mL carbenicillin, 0.1% glucose. The cultures were then grown with vigorous shaking at 37° C. until the $OD_{600}$ reached 0.6 before infecting the E. coli by adding 2×10¹¹ VCSM13 helper phage (Agilent) per 100 mL of culture. The infection was allowed to proceed for 1 hour at 37° C. before chilling the cultures on ice and adding kanamycin to 30 µg/mL. IPTG was also added to 0.5 mM to induce the expression of the scaffold-pIII fusion genes. The cultures were then grown overnight at 26° C.

A 50 mL aliquot of each of the overnight cultures was centrifuged at 8000×g at 4° C. for 20 minutes and the supernatants containing the phage particles were carefully recovered and filtered through 0.45 m filters (Sartorius). These filtrates were chilled on ice and a 0.25× volume of 20% (w/v) PEG, 2.5 M NaCl was added and left on ice for 1 hour to precipitate the phage. The precipitate was centrifuged at 8000×g for 30 minutes at 4° C. and the phage pellets were individually resuspended in 500 µl of PBS. For each target, 62 µl of phage derived from the randomized first round panning selection output, and 438 µl of phage derived from the first round panning selection output were combined to give 500 µl volume mixtures of combined phage.

Each of these combined phage mixtures was then used to conduct a second round of selection on their respective biotinylated antigens as described above, but with the biotinylated antigens added to the phage supernatant to a final concentration of 10 nM. Approximately $3.6 \times 10^5$ clones and $1.1 \times 10^5$ clones were obtained from the PD-L1 and HER2 second round panning outputs respectively. The next day the colonies from each of the plates were harvested by scraping the plates with LB medium containing 1% glucose, 100 µg/mL ampicillin and 15% glycerol, and the resuspended cells were divided into 0.5 mL aliquots, and stored at −80° C. as second round panning selection output $E.$ $coli$ glycerol stocks until further use.

Aliquots of the second round panning selection output $E.$ $coli$ glycerol stocks above were thawed and diluted in 100 mL of 2×YT medium to give an $OD_{600}$ of 0.2. To each culture, carbenicillin and glucose were added to a final concentration of 100 g/mL carbenicillin, 0.1% glucose. The cultures were then grown with vigorous shaking at 37° C. until the $OD_{600}$ reached 0.6 before infecting the $E.$ $coli$ by adding $2 \times 10^{11}$ VCSM13 helper phage (Agilent) per 100 mL culture. The infection was allowed to proceed for 1 hour at 37° C. before chilling the cultures on ice and adding kanamycin to 30 µg/mL. IPTG was also added to 0.5 mM to induce the expression of the scaffold-pIII fusion genes. The cultures were then grown overnight at 26° C. A 50 mL aliquot of each of the overnight cultures was centrifuged at 8000×g at 4° C. for 20 minutes and the supernatants containing the phage particles were carefully recovered and filtered through 0.45 m filters (Sartorius). These filtrates were chilled on ice and a 0.25× volume of 20% (w/v) PEG, 2.5 M NaCl was added and left on ice for 1 hour to precipitate the phage. The precipitates were centrifuged at 8000×g for 30 minutes at 4° C. and the phage pellets obtained from each panning output were individually resuspended in 1 mL of PBS. Each of these phage preparations were divided into two separate tubes (containing 500 µl of phage per tube), and used to carry out a third round of panning with their respective biotinylated antigens at 5 nM and 500 µM final concentrations. Panning was carried out for each sample as described above. For the PD-L1 third round selection, approximately $3.3 \times 10^6$ clones and $8.2 \times 10^5$ clones were obtained from the 5 nM and 500 µM panning outputs respectively. For the HER2 third round selection, approximately $1.5 \times 10^6$ clones and $3.2 \times 10^5$ clones were obtained from the 5 nM and 500 µM panning outputs respectively. The colonies from each of the plates were harvested by scraping the plates with LB medium containing 1% glucose, 100 µg/mL ampicillin and 10% glycerol, and the resuspended cells were divided into 0.5 mL aliquots, and stored at −80° C. as third round panning selection output $E.$ $coli$ glycerol stocks until further use.

Example 5

Figure 12A:
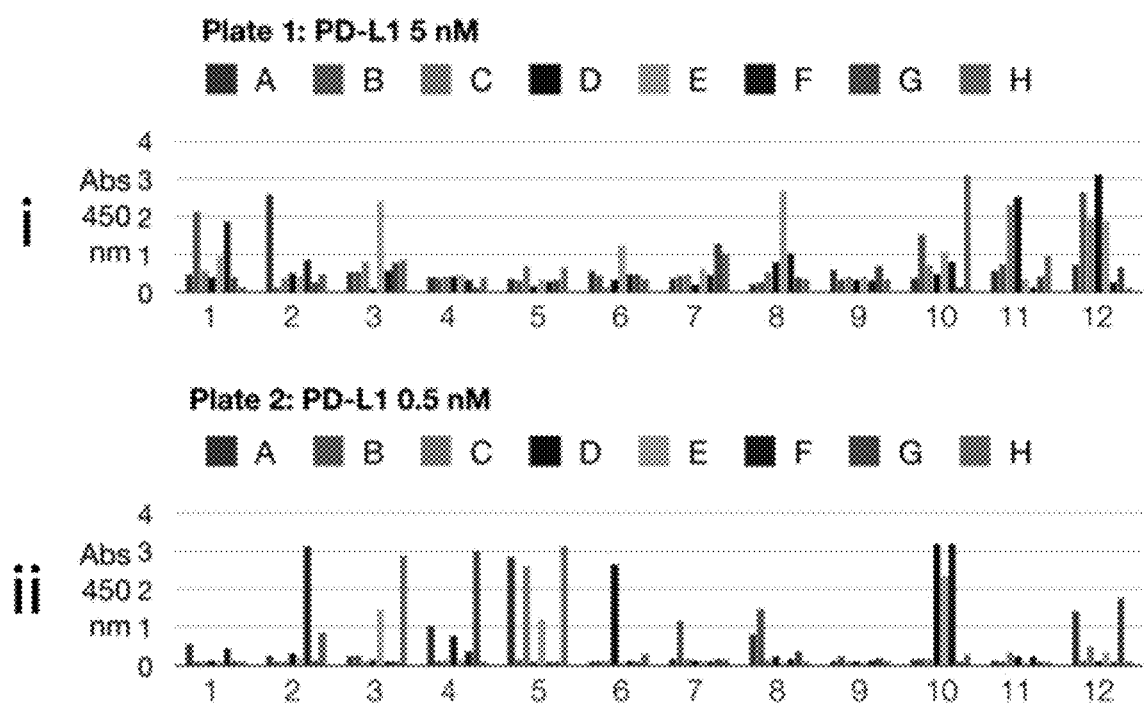
FIG. 12A. ELISA screening of individual clones from selection outputs against target PD-L1. The bar graphs show the ELISA signals obtained from clones obtained from the outputs of the third round of phage display selections carried out with the PD-L1 target at (i) a concentration of 5 nM and (ii) a concentration of 0.5 nM (Plate 1 and Plate 2, respectively).

Identification of Target Binding Clones of the Scaffold of the Invention by ELISA A pool of recombinant phagemid DNA was isolated from aliquots of each of the glycerol stocks from the 3rd round selection outputs described above using a FastGene Plasmid Mini Kit (NIPPON Genetics, Japan). Phagemid DNA (5 g) was digested with 50 units each of EcoRI-HF and AscI (New England Biolabs) for 2 hours at 37° C. and the insert DNA was gel purified as previously described. A 100 ng aliquot of the resultant DNA inserts were ligated with 100 ng of a modified pQE-80L (QIAGEN) vector comprising corresponding EcoRI and AscI cloning sites in a 20 µl volume with 400 U of T4 DNA ligase (New England Biolabs) for 2 hours at 16° C. The ligation mixtures were then heated at 65° C. for 10 minutes and used to transform chemically competent $E.$ $coli$ XL1-Blue (Agilent) according to the manufacturer's instructions and plated out on 2×YT agar plates containing 2% glucose and 50 µg/mL kanamycin at 37° C. overnight. The next day 95 individual colonies were picked from each transformation output and grown in 96 well plates ("expression plates") containing 110 µl per well of 2×YT medium containing 0.1% glucose and 50 µg/mL kanamycin at 37° C. for 4 hours with gentle shaking (plate well 12H of each "expression plate" was not inoculated with bacteria). Following this, 10 µl from each well was transferred to a replicate 96 well plates ("storage plates") containing 100 µl per well of TB medium containing 1% glucose and 50 µg/mL kanamycin. Storage plates were grown overnight at room temperature with shaking. Meanwhile IPTG was added to each well of the expression plates to a final concentration of 0.5 mM IPTG to induce expression of individual clones, and expression was allowed to proceed overnight at room temperature with gentle shaking. The next day, 100 µl aliquots of of TB medium containing 1% glucose, 50 µg/mL kanamycin and 30% glycerol were added to each well of the storage plates. The storage plates were then sealed with adhesive aluminum foil sheets and frozen at −80° C. to serve as a glycerol stock of individual clones. Following this, 40 µl of lysis buffer (24.7 g/l boric acid, 18.7 g/l NaCl, 1.49 g/l EDTA, pH8.0) containing 2.5 mg/mL human lysozyme (Merck), and 20 U/mL benzonase (Merck) were added to each well of the expression plates, and shaken at room temperature for 1 hour. Then 40 µl of 12.5% (w/v) skim milk powder in PBS was added to each well of the expression plates (final concentration 2.5% (w/v) skim milk) and plates were shaken for 30 minutes at room temperature. This resultant blocked cell lysate containing scaffolds of the invention from individually expressed clones was screened for binding to target antigens by ELISA as follows. Antigens were dissolved in PBS to 1 µg/mL and 100 µl coated onto the surface of each well of a 96 well MaxiSorp Plate (Nunc) at 4° C. overnight. The next day, the wells of the MaxiSorp plate were washed with PBST buffer (PBS containing 0.05% Tween-20) and the wells blocked with 400 µl per well of 5% (w/v) skim milk powder in PBST for 2 hours. This blocking buffer was then discarded and the wells of the plate washed with PBST. The blocked cell lysates were then transferred to the MaxiSorp plate and allowed to bind to the immobilized blocked antigens for 2 hours at room temperature with gentle shaking. Following this, the lysate was discarded and the wells of the MaxiSorp plate were washed 4 times with PBST. Then, 100 µl of a 1/4000 diluted solution of anti-FLAG M2 HRP conjugated antibody (Sigma) in PBST containing 2.5% (w/v) skim milk was added to each well and allowed to bind for 1 hour. This was then discarded and the plate washed 4 times with PBST. Then 100 µl of ELISA POD Substrate TMB Kit (HYPER) detection reagent (Nacalai Tesque, Japan) was added per well and the color development reaction stopped by addition of 100 µl of 1M phosphoric acid. Absorbance of each well was read at 450 nm wavelength (FIGS. 12A and 12B). Clones which generated positive binding signals were identified and grown from inoculates taken from individual wells of the glycerol stock storage plates described above. Cultures were grown in 2 mL of TB medium containing 1% glucose and 50 µg/mL kanamycin at 37° C. overnight with shaking. Plasmids were isolated from these cultures using a FastGene Plasmid Mini Kit (NIPPON Genetics, Japan) and sequencing of the DNA region encoding the scaffolds of the invention were performed by Eurofins Genomics (Japan).

Example 6

Figure 13:
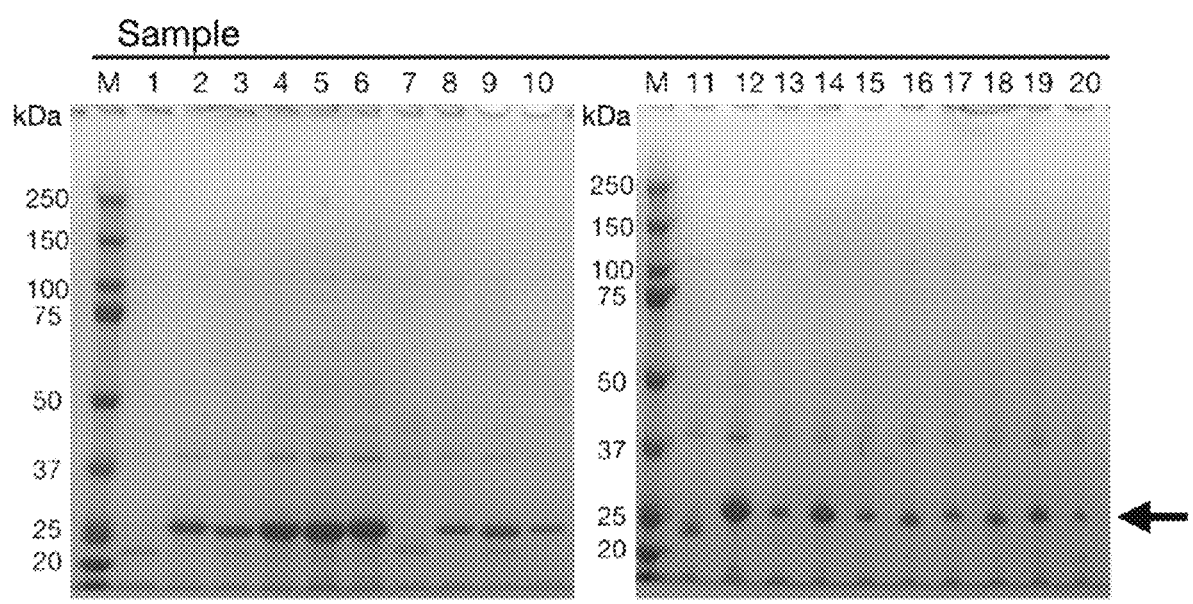
FIG. 13. Denaturing SDS-PAGE (4-12%) analysis of selected purified ELISA positive target binding proteins of the scaffold of the invention. Proteins were purified on cobalt agarose beads from the soluble fractions of lysates of induced expression construct containing E. coli XL1-Blue cells under native conditions. The amount of purified protein loaded in each gel lane is equivalent to that derived from 100 µl of overnight 2×YT broth shake flask culture. Proteins were visualized with coomassie blue stain. The arrow indicates the approximate expected migration position of the scaffold proteins, based on molecular weight calculations. The sample lanes are labeled at the top of the figure. Lane M: Precision Plus Protein Standard (Bio-Rad); Lane 1: 1-12D (SEQ ID NO: 52); Lane 2: 1-12B (SEQ ID NO: 53); Lane 3: 2-8B (SEQ ID NO: 54); Lane 4: 1-2A (SEQ ID NO: 55); Lane 5: 1-3E (SEQ ID NO: 56); Lane 6: 1-12C (SEQ ID NO: 57); Lane 7: 1-10B (SEQ ID NO: 58); Lane 8: 1-1E (SEQ ID NO: 59); Lane 9: 2-3H (SEQ ID NO: 60); Lane 10: 2-6D (SEQ ID NO: 61); Lane 11: 3-1D (SEQ ID NO: 62); Lane 12: 3-3A (SEQ ID NO: 63); Lane 13: 3-5A (SEQ ID NO: 64); Lane 14: 3-7E (SEQ ID NO: 65); Lane 15: 3-8A (SEQ ID NO: 66); Lane 16: 3-10H (SEQ ID NO: 67); Lane 17: 4-3E (SEQ ID NO: 68); Lane 18: 4-7D (SEQ ID NO: 69); Lane 19: 4-9B (SEQ ID NO: 70); Lane 20: 4-12B (SEQ ID NO: 71).
Figure 14:
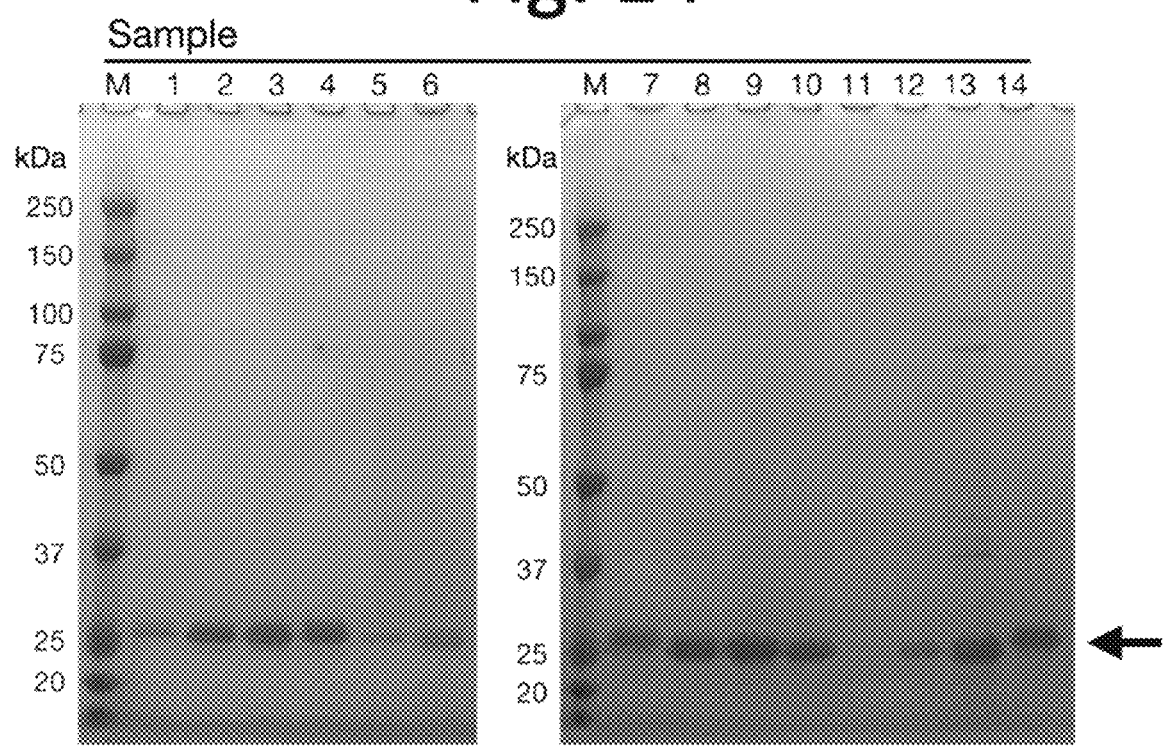
FIG. 14. Denaturing SDS-PAGE (4-12%) analysis of selected purified ELISA positive target binding proteins of the scaffold of the invention. Proteins were purified on cobalt agarose beads from the soluble fractions of lysates of induced expression construct containing E. coli XL1-Blue cells under native conditions. The amount of purified protein loaded in each gel lane is equivalent to that derived from 100 µl of overnight 2×YT broth shake flask culture. Proteins were visualized with coomassie blue stain. The arrow indicates the approximate expected migration position of the scaffold proteins, based on molecular weight calculations. The sample lanes are labeled at the top of the figure. Lane M: Precision Plus Protein Standard (Bio-Rad); Lane 1: 1-12B (SEQ ID NO: 53); Lane 2: 1-2A (SEQ ID NO: 55); Lane 3: 1-3E (SEQ ID NO: 56); Lane 4: 1-12C (SEQ ID NO: 57); Lane 5: 1-1E (SEQ ID NO: 59); Lane 6: 2-3H (SEQ ID NO: 60); Lane 7: 1-8E (SEQ ID NO: 72); Lane 8: 1-11C (SEQ ID NO: 73); Lane 9: 1-1B (SEQ ID NO: 74); Lane 10: 1-12E (SEQ ID NO: 75); Lane 11: 1-1F (SEQ ID NO: 76); Lane 12: 2-5H (SEQ ID NO: 77); Lane 13: 2-5C (SEQ ID NO: 78); Lane 14: 2-7B (SEQ ID NO: 79).
Figure 15:
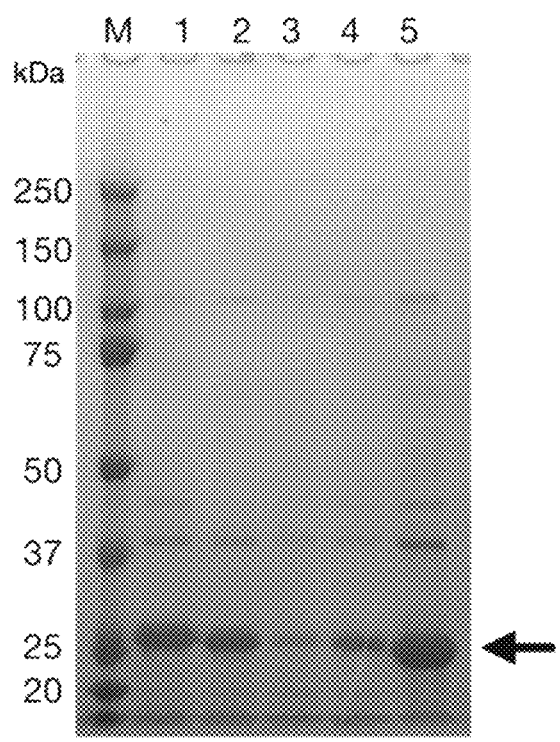
FIG. 15. Denaturing SDS-PAGE (4-12%) analysis of selected purified ELISA positive target binding proteins of the scaffold of the invention, and the purified protein of the test loop graft construct (SEQ ID NO: 49) derived from Chemotaxis protein CheY of *Fervidobacterium pennivorans*. Proteins were purified on cobalt agarose beads from the soluble fractions of lysates of induced expression construct containing E. coli XL1-Blue cells under native conditions. The amount of purified protein loaded in each gel lane is equivalent to that derived from 100 µl of overnight 2×YT broth shake flask culture. Proteins were visualized with coomassie blue stain. The arrow indicates the approximate expected migration position of the scaffold proteins, based on molecular weight calculations. The lanes are labeled at the top of the figure. Lane M: Precision Plus Protein Standard (Bio-Rad); Lane 1: 3-3A (SEQ ID NO: 63); Lane 2: 3-7E (SEQ ID NO: 65); Lane 3: 3-8A (SEQ ID NO: 66); Lane 4: 4-7D (SEQ ID NO: 69); Lane 5: the test loop graft construct (SEQ ID NO: 49) derived from Chemotaxis protein CheY of *Fervidobacterium pennivorans*.
Figure 16A:
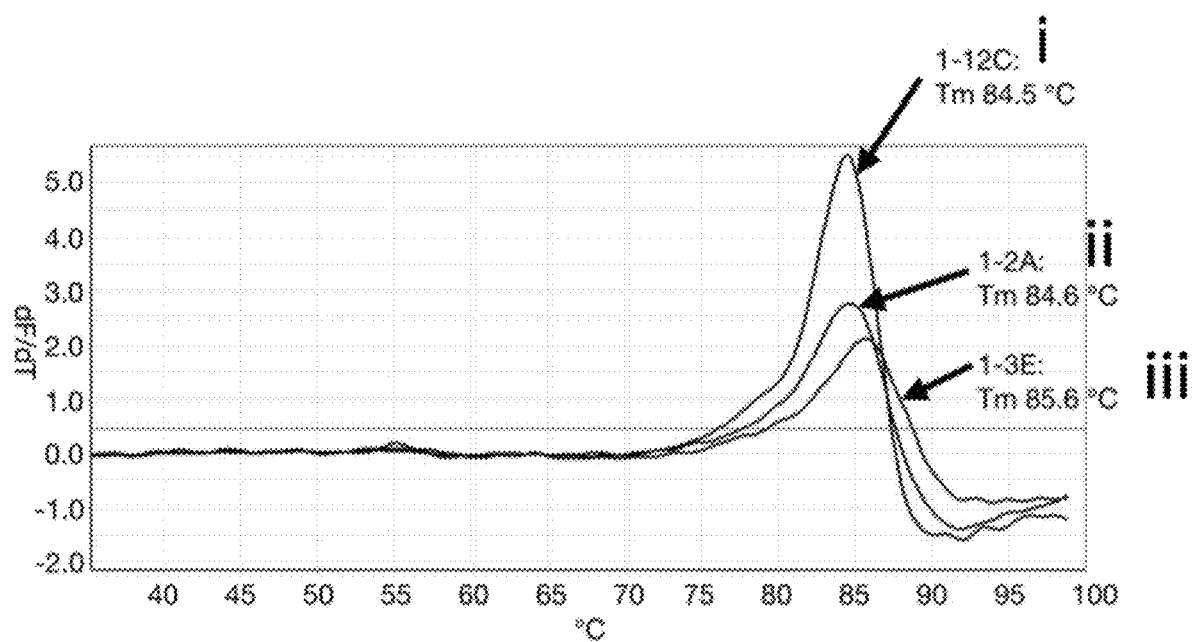
FIG. 16A. First derivative curves of fluorescence intensity obtained by differential scanning fluorimetry (DSF) of selected purified ELISA positive target binding proteins of the scaffold of the invention. The melting temperatures of each protein are indicated on the figure as (i) 1-12C: 84.5° C.; (ii) 1-2A: 84.6° C.; (iii) 1-3E: 85.6° C. The sequence identities of the proteins are SEQ ID NO: 57, SEQ ID NO: 55 and SEQ ID NO: 56, respectively.
Figure 16B:
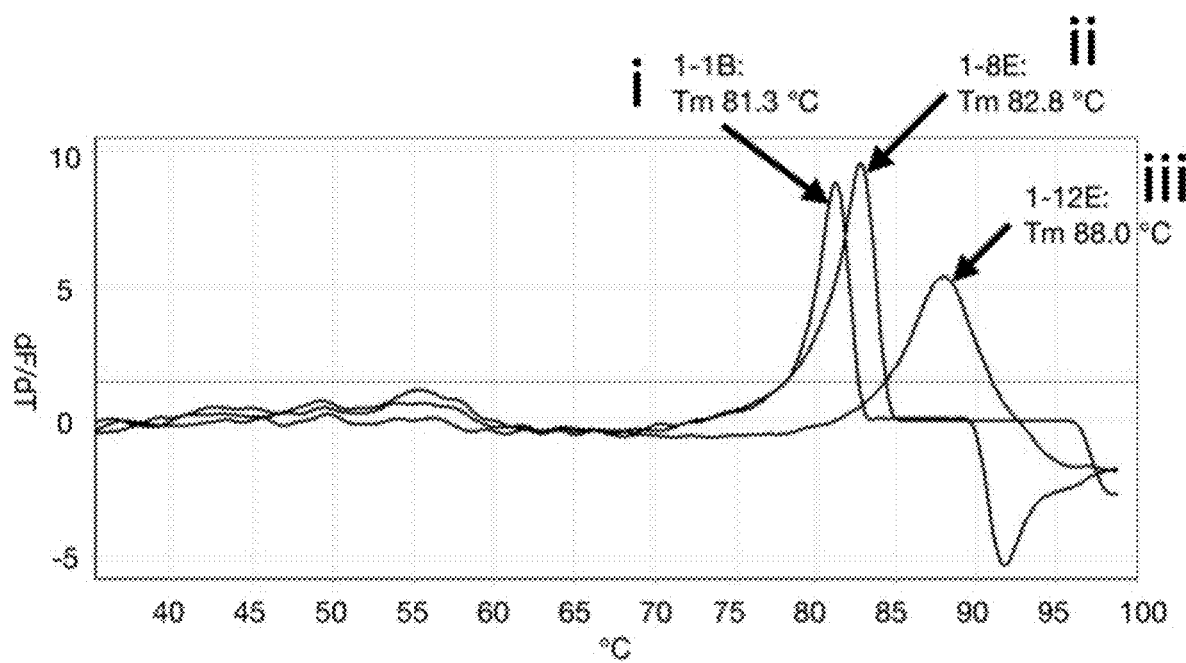
FIG. 16B. First derivative curves of fluorescence intensity obtained by differential scanning fluorimetry (DSF) of selected purified ELISA positive target binding proteins of the scaffold of the invention. The melting temperatures of each protein are indicated on the figure as (i) 1-1B: 81.3° C.; (ii) 1-8E: 82.8° C.; (iii) 1-12E: 88.0° C. The sequence identities of the proteins are SEQ ID NO: 74, SEQ ID NO: 72 and SEQ ID NO: 75, respectively.
Figure 16C:
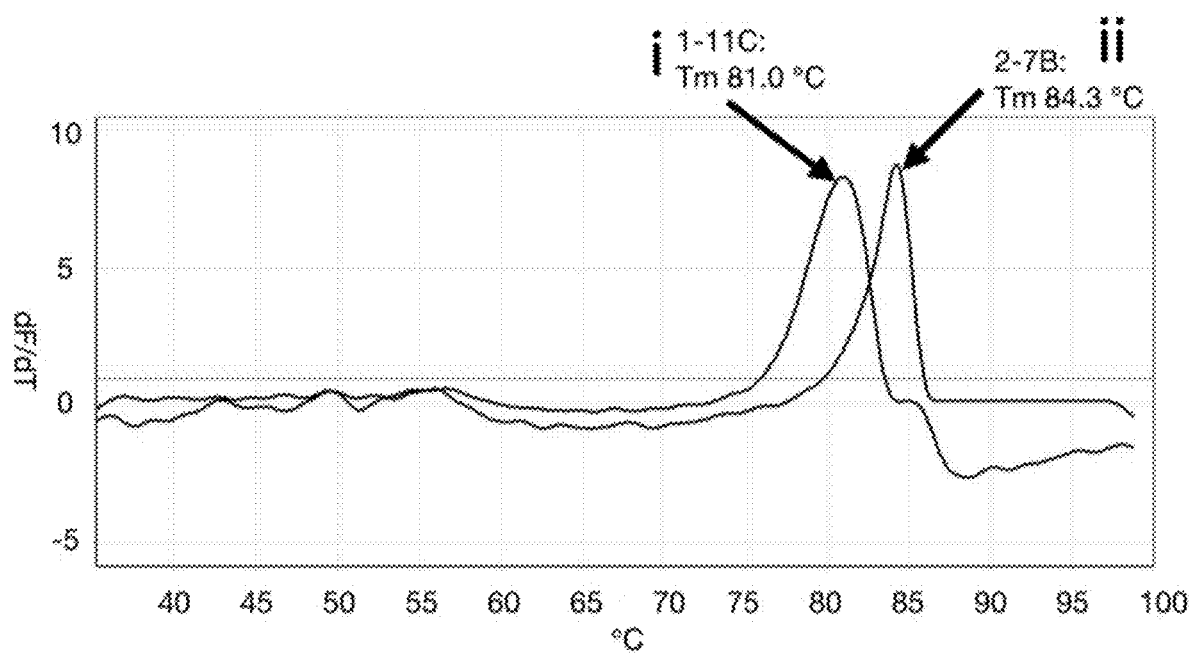
FIG. 16C. First derivative curves of fluorescence intensity obtained by differential scanning fluorimetry (DSF) of selected purified ELISA positive target binding proteins of the scaffold of the invention. The melting temperatures of each protein are indicated on the figure as (i) 1-11C: 81.0° C.; (ii) 2-7B: 84.3° C. The sequence identities of the proteins are SEQ ID NO: 73 and SEQ ID NO: 79, respectively.
Figure 16D:
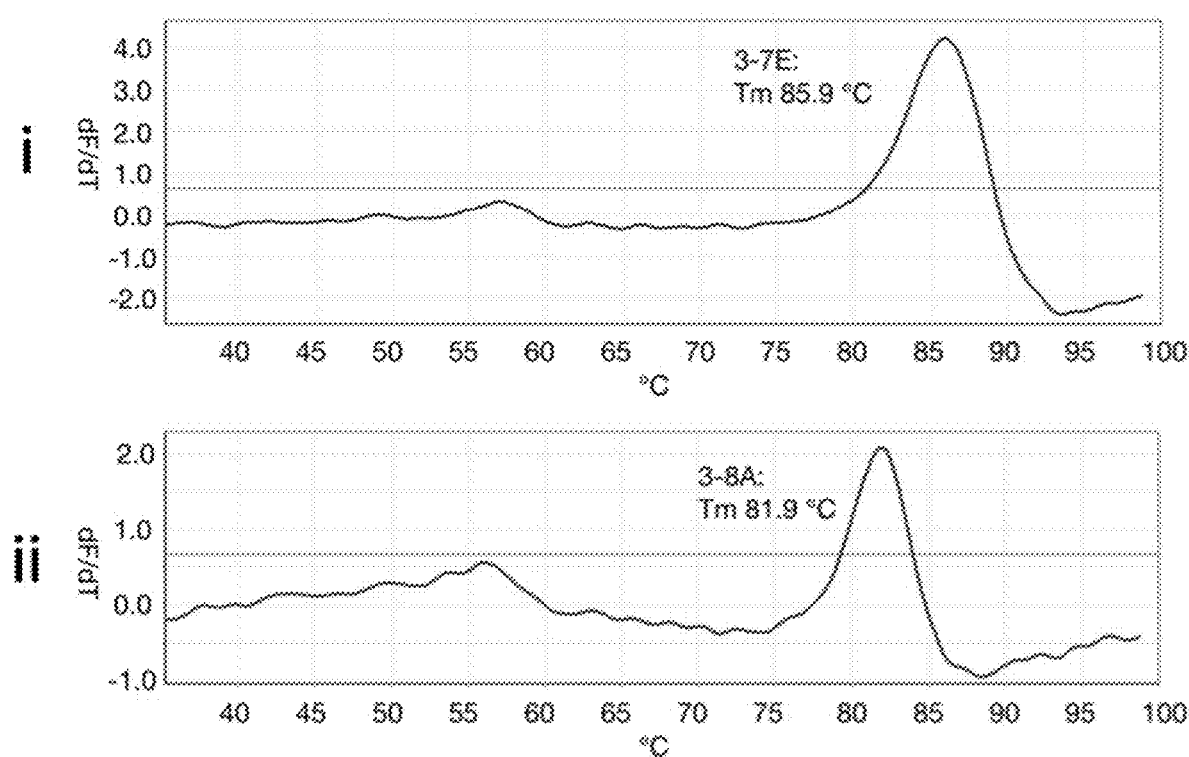
FIG. 16D. First derivative curves of fluorescence intensity obtained by differential scanning fluorimetry (DSF) of selected purified ELISA positive target binding proteins of the scaffold of the invention. The melting temperatures of each protein are indicated on the figure as (i) 3-7E: 85.9° C.; (ii) 3-8A: 81.9° C. The sequence identities of the proteins are SEQ ID NO: 65 and SEQ ID NO: 66, respectively.
Figure 16E:
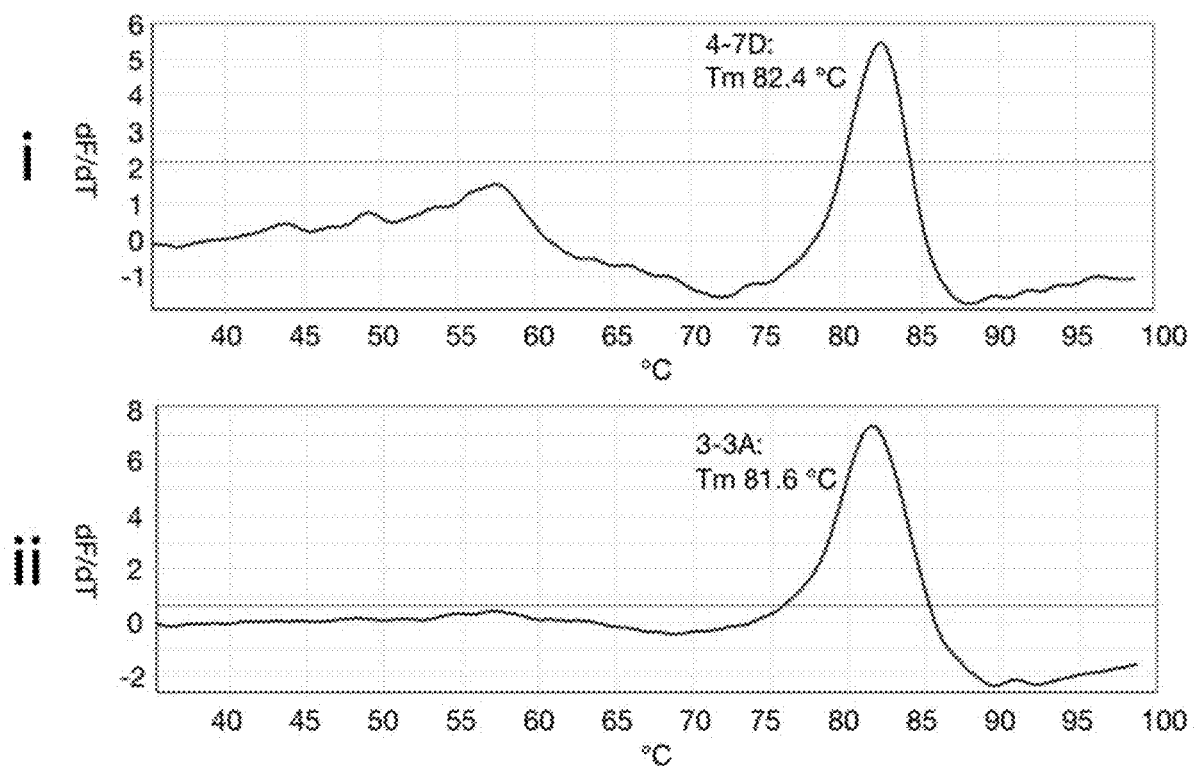
FIG. 16E. First derivative curves of fluorescence intensity obtained by differential scanning fluorimetry (DSF) of selected purified ELISA positive target binding proteins of the scaffold of the invention. The melting temperatures of each protein are indicated on the figure as (i) 4-7D: 82.4° C.; (ii) 3-3A: 81.6° C. The sequence identities of the proteins are SEQ ID NO: 69 and SEQ ID NO: 63, respectively.

Small Scale Protein Purification and Characterization of Target Binding Scaffolds E. coli glycerol stocks of sequence verified target binding clones from the storage plate (described in Example 5) were used to inoculate 50 mL cultures of 2×YT medium containing 50 µg/mL kanamycin and 0.1% glucose at 37° C. with vigorous shaking until $OD_{600}$ reached 0.5. Then cultures were chilled on ice and IPTG added to 0.5 mM and cultures allowed to grow overnight at 27° C. with vigorous shaking. Cultures were centrifuged at 3000×g for 10 minutes at 4° C. and the cell pellets were resuspended in 27 mL of ice cold PBS (pH 7.4) containing 300 mM NaCl. Then 3 mL of 10× bugbuster reagent (EMD Millipore) was added and the cells allowed to lyse on ice for 30 minutes. The cell lysates were then centrifuged at 12,000×g for 30 minutes at 4° C. and the supernatants containing the cell lysates were recovered. These were then allowed to bind to a 1 mL bed volume of pre-equilibrated Talon Cell-thru resin (Clontech) and the purification was continued according to the manufacturer's instructions and eluted in a 5 mL volume. Purified proteins were visualized by running 10 µl aliquots on NuPAGE 4-12% SDS-PAGE gels (Invitrogen) and staining with Coomassie blue stain (FIGS. 13-15). The eluted proteins were buffer exchanged for PBS (pH 7.4) by repeated centrifugation through Amicon Ultra-4 10,000 MWCO columns (Millipore) according to the manufacturer's instructions, and proteins were recovered in an approximately 1 mL volume. Protein concentrations were calculated based on measured absorbance at 280 nm compared to extinction coefficients predicted from amino acid sequences deduced from DNA sequence data.

Thermostability of the proteins of the scaffold of the invention was determined by DSF measurements with SYPRO orange dye (Merck) with proteins at 500 µg/mL in PBS buffer (pH 7.4) at a scanning rate of 0.5° C./min (FIGS. 16A-16E). The melting temperature of the proteins were determined from the temperatures at the maxima of the first derivative curves of fluorescence intensity.

Affinity of binding of individual scaffolds of the invention was estimated by ELISA. Antigens were dissolved in PBS to 1 µg/mL and 100 µl coated onto the surface of each well of a 96 well MaxiSorp Plate (Nunc) at 4° C. overnight. The next day, the wells of the MaxiSorp plate were washed with PBST buffer (PBS containing 0.05% Tween-20) and the wells blocked with 400 µl per well of 5% (w/v) skim milk powder in PBST for 2 hours. This blocking buffer was then discarded and the wells of the plate washed with PBST. Purified proteins of target binding scaffolds of the invention were diluted in a 96 well plate using a threefold series dilution at various concentrations ranging from 10.8 µM to 20 µM in PBS containing 2.5% (w/v) skim milk. The diluted target binding scaffold proteins were then transferred to the antigen coated MaxiSorp plate and allowed to bind to the immobilized blocked antigens for 2 hours at room temperature with gentle shaking. Following this, the diluted target binding scaffold protein solution was discarded and the wells of the MaxiSorp plate were washed 4 times with PBST. Then, 100 µl of a ¼₀₀₀ diluted solution of anti-FLAG M2 HRP conjugated antibody (Sigma) in PBST containing 2.5% (w/v) skim milk was added to each well and allowed to bind for 1 hour. This was then discarded and the plate washed 4 times with PBST. Then 100 µl of ELISA POD Substrate TMB Kit (HYPER) detection reagent (Nacalai Tesque, Japan) was added per well and the color development reaction stopped by addition of 100 µl of 1M phosphoric acid. Absorbance of each well was read at 450 nm wavelength. The $EC_{50}$ of binding was calculated from four parameter logistic plots of the measured absorbance values (FIGS. 17A-17B).

Example 7

Evaluation of Randomization Potential of Proteins with Sequence Homology to the Scaffold of the Invention In order to determine if the randomization scheme of the present invention is broadly applicable to proteins with sequence homology to the scaffold of the invention, a polypeptide sequence homology search was made to identify homologous candidates. The polypeptide sequence of the $CheB_c$ domain (SEQ ID NO: 1) was used to search the NCBI (National Center for Biotechnology Information) protein sequence database for homologous polypeptides using the blastp algorithm. Several proteins were thus identified which exhibited homology to the $CheB_c$ domain. One of them, a domain of the chemotaxis protein CheY of *Fervidobacterium pennivorans* (GenBank ID: ANE42371.1 amino acid residues 147-337) (SEQ ID NO: 48), exhibited 78% homology to the $CheB_c$ domain (SEQ ID NO: 1) (FIG. 18), and it was expected that individual loop grafted variants of the *Fervidobacterium* sp. domain protein would exhibit even lower sequence homology to SEQ ID NO: 1. The *Fervidobacterium* sp. protein domain was thus chosen as a candidate for test loop grafting.

Using information gained from the sequence alignment, test loop grafts similar to those used to test the randomization design of the scaffold of the invention were designed and incorporated into the *Fervidobacterium* sp. protein, together with a Cys159Ser substitution in SEQ ID NO: 48 for the purpose of generating a cysteine free test loop graft construct (SEQ ID NO: 49), (FIGS. 19 and 20). The polypeptide sequence of the test loop grafted *Fervidobacterium* sp. protein construct flanked with EcoRI and AscI sites (SEQ ID NO: 50) was encoded by synthetic DNA (SEQ ID NO: 51) obtained from Eurofins Genomics (Japan) and cloned into a modified pQE-80L vector (QIAGEN) comprising corresponding EcoRI and AscI cloning sites, and transformed into *E. coli* XL1-Blue (Agilent). A glycerol stock of a sequence verified clone was used to inoculate a 50 mL culture of 2×YT medium containing 50 μg/mL kanamycin and 0.1% glucose and grown at 37° C. with vigorous shaking until $OD_{600}$ reached 0.5. The cultures was chilled on ice and IPTG added to 0.5 mM and the culture allowed to grow overnight at 27° C. with vigorous shaking. The culture was centrifuged at 3000×g for 10 minutes at 4° C. and the cell pellet was resuspended in 27 mL of ice cold PBS (pH 7.4) containing 300 mM NaCl. Then 3 mL of 10× bugbuster reagent (EMD Millipore) was added and the cells allowed to lyse on ice for 30 minutes. The cell lysate was then centrifuged at 12,000×g for 30 minutes at 4° C. and the supernatant containing the cell lysate was recovered. This was then allowed to bind to a 1 mL bed volume of pre-equilibrated Talon Cell-thru resin (Clontech) and the purification was continued according to the manufacturer's instructions and eluted in a 5 mL volume. The purified protein was visualized by running a 10 µl aliquot on a NuPAGE 4-12% SDS-PAGE gel (Invitrogen) and staining with Coomassie blue stain (FIG. 15). The eluted protein was buffer exchanged for PBS (pH 7.4) by repeated centrifugation through an Amicon Ultra-4 10,000 MWCO column (Millipore) according to the manufacturer's instructions, and the protein was recovered in an approximately 1 mL volume. The protein concentration was calculated based on measured absorbance at 280 nm compared to the extinction coefficient predicted from the amino acid sequence deduced from DNA sequence data. Thermostability of the test loop grafted *Fervidobacterium* sp. protein was determined by DSF measurement with SYPRO orange dye (Merck) with the protein at 500 µg/mL in PBS buffer (pH 7.4) at a scanning rate of 0.5° C./min (FIG. 21). The melting temperature of the protein (78° C.) was determined from the temperature at the maximum of the first derivative curve of fluorescence intensity.

While the foregoing invention has been described in some detail for purposes of clarity and understanding, it will be clear to one skilled in the art from a reading of this disclosure that various changes in form and detail can be made without departing from the true scope of the invention.

REFERENCES CITED

Binz H., Stumpp M., Forrer P., Amstutz P., Pluckthun A. (2003). Designing repeat proteins: Well-expressed, soluble and stable proteins from combinatorial libraries of consensus ankyrin repeat proteins. Journal of Molecular Biology 332, 489-503.

Cho K., Crane B., Park S. (2011). An insight into the interaction mode between CheB and chemoreceptor from two crystal structures of CheB methylesterase catalytic domain. Biochemical and Biophysical Research Communications 411, 69-75.

Du B., Han H., Wang Z., Kuang L., Wang L., Yu L., Wu M., Zhou Z., Qian M. (2010). Targeted drug delivery to hepatocarcinoma in vivo by phage-displayed specific binding peptide. Molecular Cancer Research 8, 135-144.

Dudgeon K., Rouet R., Christ D. (2013). Rapid prediction of expression and refolding yields using phage display. Protein Engineering, Design and Selection 26, 671-674.

Gilbreth R., Koide S. (2012). Structural insights for engineering binding proteins based on non-antibody scaffolds. Current Opinion in Structural Biology 22, 413-420.

Honegger A., Malebranche A., Rothlisberger D., Pluckthun A. (2009). The influence of the framework core residues on the biophysical properties of immunoglobulin heavy chain variable domains. Protein Engineering, Design & Selection 22, 121-134.

Jensen K., Andreatta M., Marcatili P., Buus S., Greenbaum J., Yan Z., Sette A., Peters B., Nielsen M. (2018). Improved methods for predicting peptide binding affinity to MHC class II molecules. Immunology 154, 394-406.

Miller B., Demarest S., Lugovskoy A., Huang F., Wu X., Snyder W., Croner L., Wang N., Amatucci A., Michaelson J., Glaser S. (2010). Stability engineering of scFvs for the development of bispecific and multivalent antibodies. Protein Engineering Design and Selection 23, 549-557.

Nagi A., Regan L. (1997). An inverse correlation between loop length and stability in a four-helix bundle protein. Folding and Design 2: 67-75

Regan L. (1999). Protein redesign. Current Opinion in Structural Biology 9:494-499.

Schilling J., Schoppe J., Pluckthun A. (2014). From DARPins to LoopDARPins: novel LoopDARPin design allows the selection of low picomolar binders in a single round of ribosome display. Journal of Molecular Biology 426, 691-721.

Schmidt A., Kochanowski K., Vedelaar S., Ahrne E., Volkmer B., Callipo L., Knoops K., Bauer M., Aebersold R., Heinemann M. (2015). The quantitative and condition-dependent *Escherichia coli* proteome. Nature Biotechnology 34, 104-110.

Vogt M., Skerra A. (2004). Construction of an artificial receptor protein ("anticalin") based on the human apolipoprotein D. Chembiochem 5:191-199.

Willuda J., Honegger A., Waibel R., Schubiger A., Stahel R., Uwe Z., Pluckthun A. (1999). High thermal stability is essential for tumor targeting of antibody fragments: Engineering of a humanized anti-epithelial glycoprotein-2 (epithelial cell adhesion molecule) single-chain Fv fragment. Cancer Research 59, 5758-5767.

Xu L., Kohli, N., Rennard R., Yang J., Razlog M., Zhang K., Baum J., Johnson B., Tang J., Schoeberl B., Fitzgerald J., Nielsen U., Lugovskoy A. (2013). Rapid optimization and prototyping for therapeutic antibody-like molecules. mAbs 5, 237-254.

Zhao N., Schmitt M., Fisk J. (2016). Phage display selection of tight specific binding variants from a hyperthermostable Sso7d scaffold protein library. The FEBS Journal 283, 1351-1367.

What is claimed:

1. A polypeptide display library comprising a recombinant polypeptide scaffold comprising a recombinant $CheB_c$ domain comprising: (i) four framework regions designated FR1, FR2, FR3, and FR4, having at least 80% identity to the amino acid sequence of SEQ ID NO: 40 for FR1, SEQ ID NO: 41 for FR2, SEQ ID NO: 42 for FR3 and, SEQ ID NO: 43 for FR4; (ii) the four framework regions connected by three loop regions, wherein said scaffold has three loop regions designated L1, L2 and L3; wherein between one to three of said loop regions are randomized, wherein randomized L1 has an amino acid sequence of SEQ ID NO: 44 or SEQ ID NO: 45, randomized L2 has an amino acid sequence of SEQ ID NO: 44 or SEQ ID NO: 46, and randomized L3 has an amino acid sequence of SEQ ID NO: 47; wherein for the randomized L1, L2, and L3 loop regions each Xaa independently represents any amino acid; and wherein L1 is linked between FR1 and FR2, L2 is linked between FR2 and FR3, and L3 is linked between FR3 and FR4 to form a contiguous polypeptide comprising the arrangement FR1—L1—FR2—L2—FR3—L3—FR4.

2. The library of claim 1, wherein L1 is represented by SEQ ID NO: 44, L2 is represented by SEQ ID NO: 44, and L3 is represented by SEQ ID NO:47;
and wherein for the L1, L2 and L3 loop regions each Xaa independently represents serine, aspartic acid, arginine, alanine, leucine, threonine, asparagine, tryptophan, glycine, glutamic acid, valine or tyrosine.

3. The library of claim 1, wherein L1 is represented by SEQ ID NO: 45, L2 is represented by SEQ ID NO: 46, and L3 is represented by SEQ ID NO:47;
wherein for the L1 and L2 loop regions each Xaa independently represents any amino acid;
and wherein for the L3 loop region each Xaa independently represents serine, aspartic acid, arginine, alanine, leucine, threonine, asparagine, tryptophan, glycine, glutamic acid, valine or tyrosine.

4. The polypeptide display library of claim 3, wherein said scaffold is displayed on the surface of a ribosome, bacteriophage, virus, bacteria, yeast, or mammalian cell.

5. The library of claim 1, wherein said library has a sequence diversity of at least $10^6$.

6. A method of obtaining a polypeptide scaffold that binds to a target, said method comprising (a) contacting a target ligand with the library of claim 1 under conditions that allow a scaffold:target ligand complex to form and, (b) obtaining from the complex, the scaffold that binds the target ligand.

7. The method of claim 6, further comprising (a) isolating a nucleic acid molecule encoding the scaffold that binds the target ligand, (b) operably linking the nucleic acid to an expression vector and, (c) expressing the nucleic acid which has been operably linked to the expression vector in a cell.

* * * * *

SEQUENCE LISTING

```
<160> NUMBER OF SEQ ID NOS: 87

<210> SEQ ID NO 1
<211> LENGTH: 193
<212> TYPE: PRT
<213> ORGANISM: Artificial Sequence
<220> FEATURE:
<223> OTHER INFORMATION: Synthetic Construct

<400> SEQUENCE: 1

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
```

```
                    20                  25                  30

Phe Pro Ala Pro Ile Val Val Gln His Met Pro Pro Gly Phe Thr
                35                  40                  45

Lys Ser Leu Ala Gln Arg Leu Asp Ser Thr Ser Glu Leu Thr Val Lys
 50                  55                  60

Glu Ala Glu Asp Gly Glu Val Lys Pro Gly Phe Val Tyr Ile Ala
 65                  70                  75                  80

Pro Gly Asp Phe His Leu Gly Leu Lys Ala Gln Asn Gly Lys Val Phe
                85                  90                  95

Phe Phe Leu Asp Lys Ser Asp Lys Ile Asn Asn Val Arg Pro Ala Val
                100                 105                 110

Asp Phe Thr Leu Asp Lys Ala Ala Glu Ile Tyr Lys Glu Lys Thr Ile
                115                 120                 125

Ala Val Ile Leu Thr Gly Met Gly Lys Asp Gly Thr Lys Gly Ala Phe
                130                 135                 140

Lys Val Lys Phe Tyr Gly Gly Thr Val Ile Ala Glu Asp Lys Glu Thr
145                 150                 155                 160

Ser Val Val Phe Gly Met Pro Lys Ser Val Ile Glu Glu Gly Tyr Ala
                165                 170                 175

Asp Tyr Val Leu Pro Ala Tyr Lys Ile Pro Glu Lys Leu Ile Glu Leu
                180                 185                 190

Val

<210> SEQ ID NO 2
<211> LENGTH: 212
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (44)..(47)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (49)..(52)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (110)..(113)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (115)..(118)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (148)..(150)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (152)..(154)
<223> OTHER INFORMATION: An amino acid selected from the group: Ser,
      Asp, Arg, Ala, Leu, Thr, Asn, Trp, Gly, Glu, Val and Tyr

<400> SEQUENCE: 2

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
                20                  25                  30
```

```
Phe Pro Ala Pro Ile Val Val Gln His Gly Xaa Xaa Xaa Gly
        35                  40                  45

Xaa Xaa Xaa Xaa Gly Thr Lys Ser Leu Ala Gln Arg Leu Asp Ser Thr
 50                  55                  60

Ser Glu Leu Thr Val Lys Glu Ala Glu Asp Gly Glu Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Phe Leu Asp Lys Ser Gly Xaa Xaa Xaa
                100                 105                 110

Xaa Gly Xaa Xaa Xaa Gly Val Arg Pro Ala Val Asp Phe Thr Leu
        115                 120                 125

Asp Lys Ala Ala Glu Ile Tyr Lys Glu Lys Thr Ile Ala Val Ile Leu
130                 135                 140

Thr Gly Gly Xaa Xaa Xaa Gly Xaa Xaa Xaa Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
                180                 185                 190

Gly Tyr Ala Asp Tyr Val Leu Pro Ala Tyr Lys Ile Pro Glu Lys Leu
                195                 200                 205

Ile Glu Leu Val
        210

<210> SEQ ID NO 3
<211> LENGTH: 214
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (45)..(47)
<223> OTHER INFORMATION: Variable amino acid
<220> FEATURE:
<221> NAME/KEY: MOD_RES
<222> LOCATION: (49)..(52)
<223> OTHER INFORMATION: Variable amino acid
<220> FEATURE:
<221> NAME/KEY: MOD_RES
<222> LOCATION: (112)..(115)
<223> OTHER INFORMATION: Variable amino acid
<220> FEATURE:
<221> NAME/KEY: MOD_RES
<222> LOCATION: (117)..(119)
<223> OTHER INFORMATION: Variable amino acid
<220> FEATURE:
<221> NAME/KEY: MOD_RES
<222> LOCATION: (150)..(152)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (154)..(156)
<223> OTHER INFORMATION: An amino acid selected from the group: Ser,
      Asp, Arg, Ala, Leu, Thr, Asn, Trp, Gly, Glu, Val and Tyr

<400> SEQUENCE: 3

Gly Ser His Met Val Ser Gly Lys Ile Val Val Ile Gly Ser Ser Thr
1               5                  10                  15

Gly Gly Pro Arg Ser Leu Asp Met Ile Ile Pro Asn Leu Pro Lys Asn
                20                  25                  30
```

```
Phe Pro Ala Pro Ile Val Val Gln His Gly Gly Xaa Xaa Xaa Gly
            35                  40                  45

Xaa Xaa Xaa Xaa Gly Gly Thr Lys Ser Leu Ala Gln Arg Leu Asp Ser
 50                  55                  60

Thr Ser Glu Leu Thr Val Lys Glu Ala Glu Asp Gly Glu Val Lys
 65                  70                  75                  80

Pro Gly Phe Val Tyr Ile Ala Pro Gly Asp Phe His Leu Gly Leu Lys
                     85                  90                  95

Ala Gln Asn Gly Lys Val Phe Phe Leu Asp Lys Ser Gly Gly Xaa
            100                 105                 110

Xaa Xaa Xaa Gly Xaa Xaa Xaa Gly Gly Val Arg Pro Ala Val Asp Phe
115                 120                 125

Thr Leu Asp Lys Ala Ala Glu Ile Tyr Lys Glu Lys Thr Ile Ala Val
130                 135                 140

Ile Leu Thr Gly Gly Xaa Xaa Xaa Gly Xaa Xaa Xaa Gly Gly Asp Gly
145                 150                 155                 160

Thr Lys Gly Ala Phe Lys Val Lys Phe Tyr Gly Gly Thr Val Ile Ala
                    165                 170                 175

Glu Asp Lys Glu Thr Ser Val Val Phe Gly Met Pro Lys Ser Val Ile
            180                 185                 190

Glu Glu Gly Tyr Ala Asp Tyr Val Leu Pro Ala Tyr Lys Ile Pro Glu
            195                 200                 205

Lys Leu Ile Glu Leu Val
            210

<210> SEQ ID NO 4
<211> LENGTH: 199
<212> TYPE: PRT
<213> ORGANISM: Artificial Sequence
<220> FEATURE:
<223> OTHER INFORMATION: Synthetic Construct

<400> SEQUENCE: 4

Gly Asn Ser Gly Ser His Met Val Ser Gly Lys Ile Val Val Ile Gly
 1               5                  10                  15

Ser Ser Thr Gly Gly Pro Arg Ser Leu Asp Met Ile Ile Pro Asn Leu
            20                  25                  30

Pro Lys Asn Phe Pro Ala Pro Ile Val Val Gln His Met Pro Pro
            35                  40                  45

Gly Phe Thr Lys Ser Leu Ala Gln Arg Leu Asp Ser Thr Ser Glu Leu
 50                  55                  60

Thr Val Lys Glu Ala Glu Asp Gly Glu Val Lys Pro Gly Phe Val
 65                  70                  75                  80

Tyr Ile Ala Pro Gly Asp Phe His Leu Gly Leu Lys Ala Gln Asn Gly
                     85                  90                  95

Lys Val Phe Phe Leu Asp Lys Ser Asp Lys Ile Asn Asn Val Arg
            100                 105                 110

Pro Ala Val Asp Phe Thr Leu Asp Lys Ala Ala Glu Ile Tyr Lys Glu
            115                 120                 125

Lys Thr Ile Ala Val Ile Leu Thr Gly Met Gly Lys Asp Gly Thr Lys
130                 135                 140

Gly Ala Phe Lys Val Lys Phe Tyr Gly Gly Thr Val Ile Ala Glu Asp
145                 150                 155                 160

Lys Glu Thr Ser Val Val Phe Gly Met Pro Lys Ser Val Ile Glu Glu
            165                 170                 175
```

Gly Tyr Ala Asp Tyr Val Leu Pro Ala Tyr Lys Ile Pro Glu Lys Leu
            180                 185                 190

Ile Glu Leu Val Gly Ala Pro
        195

<210> SEQ ID NO 5
<211> LENGTH: 636
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (130)..(132)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (133)..(135)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (136)..(138)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (139)..(141)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (145)..(147)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (148)..(150)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (151)..(153)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (154)..(156)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (328)..(330)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (331)..(333)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (334)..(336)
<223> OTHER INFORMATION: represents a codon encoding an amino acid
      residue selected from the group: Ser, Asp, Arg, Ala, Leu, Thr,
      Asn, Trp, Gly, Glu, Val and Tyr

```
<220> FEATURE:
<221> NAME/KEY: modified_base
<222> LOCATION: (337)..(339)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (343)..(345)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (346)..(348)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (349)..(351)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (352)..(354)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (442)..(444)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (445)..(447)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (448)..(450)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (454)..(456)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (457)..(459)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (460)..(462)
<223> OTHER INFORMATION: represents a codon encoding an amino acid
      residue selected from the group: Ser, Asp, Arg, Ala, Leu, Thr,
      Asn, Trp, Gly, Glu, Val and Tyr

<400> SEQUENCE: 5
ggttctcaca tggtttctgg taaaatcgtt gttatcggtt cttctaccgg tggtccgcgt      60
tctctggaca tgatcatccc gaacctgccg aaaaacttcc cggctccgat cgttgttgtt     120
cagcacggan nnnnnnnnn nggtnnnnnn nnnnnnggga ccaaatctct ggctcagcgt     180
ctggactcta cctctgaact gaccgttaaa gaagctgaag acggtgaaga agttaaaccg     240
ggtttcgttt acatcgctcc gggtgacttc cacctgggtc tgaaagctca gaacggtaaa     300
```

```
gttttcttct tcctggacaa atctggtnnn nnnnnnnng gtnnnnnnnn nnnnggggtt    360
cgtccggctg ttgacttcac cctggacaaa gctgctgaaa tctacaaaga aaaaaccatc   420
gctgttatcc tgaccggtgg annnnnnnnn ggtnnnnnnn nnggtggtga cggtactaag   480
ggcgcgttca aagttaaatt ttacggtggt actgttatcg ctgaagacaa agaaacctct   540
gttgttttcg gtatgccgaa atctgttatc gaagaaggtt acgctgacta cgttctgccg   600
gcttacaaaa tcccggaaaa actgatcgaa ctggtt                             636
```

```
<210> SEQ ID NO 6
<211> LENGTH: 642
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (133)..(134)
<223> OTHER INFORMATION: a, c, g or t
<220> FEATURE:
<221> NAME/KEY: modified_base
<222> LOCATION: (136)..(137)
<223> OTHER INFORMATION: a, c, g or t
<220> FEATURE:
<221> NAME/KEY: modified_base
<222> LOCATION: (139)..(140)
<223> OTHER INFORMATION: a, c, g or t
<220> FEATURE:
<221> NAME/KEY: modified_base
<222> LOCATION: (145)..(146)
<223> OTHER INFORMATION: a, c, g or t
<220> FEATURE:
<221> NAME/KEY: modified_base
<222> LOCATION: (148)..(149)
<223> OTHER INFORMATION: a, c, g or t
<220> FEATURE:
<221> NAME/KEY: modified_base
<222> LOCATION: (151)..(152)
<223> OTHER INFORMATION: a, c, g or t
<220> FEATURE:
<221> NAME/KEY: modified_base
<222> LOCATION: (154)..(155)
<223> OTHER INFORMATION: a, c, g or t
<220> FEATURE:
<221> NAME/KEY: modified_base
<222> LOCATION: (334)..(335)
<223> OTHER INFORMATION: a, c, g or t
<220> FEATURE:
<221> NAME/KEY: modified_base
<222> LOCATION: (337)..(338)
<223> OTHER INFORMATION: a, c, g or t
<220> FEATURE:
<221> NAME/KEY: modified_base
<222> LOCATION: (340)..(341)
<223> OTHER INFORMATION: a, c, g or t
<220> FEATURE:
<221> NAME/KEY: modified_base
<222> LOCATION: (343)..(344)
<223> OTHER INFORMATION: a, c, g or t
<220> FEATURE:
<221> NAME/KEY: modified_base
<222> LOCATION: (349)..(350)
<223> OTHER INFORMATION: a, c, g or t
<220> FEATURE:
<221> NAME/KEY: modified_base
<222> LOCATION: (352)..(353)
<223> OTHER INFORMATION: a, c, g or t
<220> FEATURE:
<221> NAME/KEY: modified_base
<222> LOCATION: (355)..(356)
<223> OTHER INFORMATION: a, c, g or t
<220> FEATURE:
<221> NAME/KEY: modified_base
<222> LOCATION: (448)..(450)
<223> OTHER INFORMATION: represents a codon encoding an amino acid
``` residue selected from the group: Ser, Asp, Arg, Ala, Leu, Thr,
        Asn, Trp, Gly, Glu, Val and Tyr
<220> FEATURE:
<221> NAME/KEY: modified_base
<222> LOCATION: (451)..(453)
<223> OTHER INFORMATION: represents a codon encoding an amino acid
        residue selected from the group: Ser, Asp, Arg, Ala, Leu, Thr,
        Asn, Trp, Gly, Glu, Val and Tyr
<220> FEATURE:
<221> NAME/KEY: modified_base
<222> LOCATION: (454)..(456)
<223> OTHER INFORMATION: represents a codon encoding an amino acid
        residue selected from the group: Ser, Asp, Arg, Ala, Leu, Thr,
        Asn, Trp, Gly, Glu, Val and Tyr
<220> FEATURE:
<221> NAME/KEY: modified_base
<222> LOCATION: (460)..(462)
<223> OTHER INFORMATION: represents a codon encoding an amino acid
        residue selected from the group: Ser, Asp, Arg, Ala, Leu, Thr,
        Asn, Trp, Gly, Glu, Val and Tyr
<220> FEATURE:
<221> NAME/KEY: modified_base
<222> LOCATION: (463)..(465)
<223> OTHER INFORMATION: represents a codon encoding an amino acid
        residue selected from the group: Ser, Asp, Arg, Ala, Leu, Thr,
        Asn, Trp, Gly, Glu, Val and Tyr
<220> FEATURE:
<221> NAME/KEY: modified_base
<222> LOCATION: (466)..(468)
<223> OTHER INFORMATION: represents a codon encoding an amino acid
        residue selected from the group: Ser, Asp, Arg, Ala, Leu, Thr,
        Asn, Trp, Gly, Glu, Val and Tyr

<400> SEQUENCE: 6
ggttctcaca tggtttctgg taaaatcgtt gttatcggtt cttctaccgg tggtccgcgt     60
tctctggaca tgatcatccc gaacctgccg aaaaacttcc cggctccgat cgttgttgtt   120
cagcacggag gannknnknn kggtnnknnk nnknnkggcg ggaccaaatc tctggctcag   180
cgtctggact ctacctctga actgaccgtt aaagaagctg aagacggtga agaagttaaa   240
ccgggtttcg tttacatcgc tccgggtgac ttccacctgg gtctgaaagc tcagaacggt   300
aaagttttct tcttcctgga caaatctggt ggtnnknnkn nknnkggtnn knnknnkgga   360
ggggttcgtc cggctgttga cttcacccct gacaaagctg ctgaaatcta caagaaaaaa   420
accatcgctg ttatcctgac cggtggannn nnnnnggtn nnnnnnnngg tggtgacggt   480
actaagggcg cgttcaaagt taaattttac ggtggtactg ttatcgctga agacaaagaa   540
acctctgttt ttttcggtat gccgaaatct gttatcgaag aaggttacgc tgactacgtt   600
ctgccggctt acaaaatccc ggaaaaactg atcgaactgg tt                       642

<210> SEQ ID NO 7
<211> LENGTH: 597
<212> TYPE: DNA
<213> ORGANISM: Artificial Sequence
<220> FEATURE:
<223> OTHER INFORMATION: Synthetic Construct

<400> SEQUENCE: 7
gggaattctg gttctcacat ggtttctggt aaaatcgttg ttatcggttc ttctaccggt     60
ggtccgcgtt ctctggacat gatcatcccg aacctgccga aaaacttccc ggctccgatc   120
gttgttgttc agcacatgcc gccgggtttc accaaatctc tggctcagcg tctggactct   180
acctctgaac tgaccgttaa agaagctgaa gacggtgaag aagttaaacc gggtttcgtt   240
tacatcgctc cgggtgactt ccacctgggt ctgaaagctc agaacggtaa agttttcttc   300
ttcctggaca aatctgacaa atcaacaac gttcgtccgg ctgttgactt caccctggac   360

-continued

```
aaagctgctg aaatctacaa agaaaaaacc atcgctgtta tcctgaccgg tatgggtaaa      420
gacggtacta agggcgcgtt caaagttaaa ttttacggtg gtactgttat cgctgaagac      480
aaagaaacct ctgttgtttt cggtatgccg aaatctgtta tcgaagaagg ttacgctgac      540
tacgttctgc cggcttacaa aatcccggaa aaactgatcg aactggttgg cgcgcca        597
```

<210> SEQ ID NO 8
<211> LENGTH: 206
<212> TYPE: PRT
<213> ORGANISM: Artificial Sequence
<220> FEATURE:
<223> OTHER INFORMATION: Synthetic Construct

<400> SEQUENCE: 8

```
Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Met Pro Pro Gly Phe Thr
        35                  40                  45

Lys Ser Leu Ala Gln Arg Leu Asp Ser Thr Ser Glu Leu Thr Val Lys
    50                  55                  60

Glu Ala Glu Asp Gly Glu Val Lys Pro Gly Phe Val Tyr Ile Ala
65                  70                  75                  80

Pro Gly Asp Phe His Leu Gly Leu Lys Ala Gln Asn Gly Lys Val Phe
                85                  90                  95

Phe Phe Leu Asp Lys Ser Gly Gly Asp Arg Asn Gly Tyr Ser Ala Gly
            100                 105                 110

Gly Val Arg Pro Ala Val Asp Phe Thr Leu Asp Lys Ala Ala Glu Ile
        115                 120                 125

Tyr Lys Glu Lys Thr Ile Ala Val Ile Leu Thr Gly Gly Leu Val Asp
    130                 135                 140

Gly Arg Glu Ala Gly Gly Asp Thr Lys Gly Ala Phe Lys Val Lys
145                 150                 155                 160

Phe Tyr Gly Gly Thr Val Ile Ala Glu Asp Lys Glu Thr Ser Val Val
                165                 170                 175

Phe Gly Met Pro Lys Ser Val Ile Glu Glu Gly Tyr Ala Asp Tyr Val
            180                 185                 190

Leu Pro Ala Tyr Lys Ile Pro Glu Lys Leu Ile Glu Leu Val
        195                 200                 205
```

<210> SEQ ID NO 9
<211> LENGTH: 205
<212> TYPE: PRT
<213> ORGANISM: Artificial Sequence
<220> FEATURE:
<223> OTHER INFORMATION: Synthetic Construct

<400> SEQUENCE: 9

```
Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Gly Leu Asp Asn Gly
        35                  40                  45

Ser Tyr Thr Gly Gly Thr Lys Ser Leu Ala Gln Arg Leu Asp Ser Thr
    50                  55                  60
```

```
Ser Glu Leu Thr Val Lys Glu Ala Glu Asp Gly Glu Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Gly Asp Arg
            100                 105                 110

Asn Gly Tyr Ser Ala Gly Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Met Gly Lys Asp Gly Thr Lys Gly Ala Phe Lys Val Lys Phe
145                 150                 155                 160

Tyr Gly Gly Thr Val Ile Ala Glu Asp Lys Glu Thr Ser Val Val Phe
                165                 170                 175

Gly Met Pro Lys Ser Val Ile Glu Glu Gly Tyr Ala Asp Tyr Val Leu
            180                 185                 190

Pro Ala Tyr Lys Ile Pro Glu Lys Leu Ile Glu Leu Val
        195                 200                 205

<210> SEQ ID NO 10
<211> LENGTH: 206
<212> TYPE: PRT
<213> ORGANISM: Artificial Sequence
<220> FEATURE:
<223> OTHER INFORMATION: Synthetic Construct

<400> SEQUENCE: 10

Gly Ser His Met Val Ser Gly Lys Ile Val Val Ile Gly Ser Ser Thr
  1               5                  10                  15

Gly Gly Pro Arg Ser Leu Asp Met Ile Ile Pro Asn Leu Pro Lys Asn
             20                  25                  30

Phe Pro Ala Pro Ile Val Val Gln His Gly Gly Leu Asp Asn Gly
         35                  40                  45

Ser Tyr Thr Gly Gly Thr Lys Ser Leu Ala Gln Arg Leu Asp Ser Thr
     50                  55                  60

Ser Glu Leu Thr Val Lys Glu Ala Glu Asp Gly Glu Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Asp Lys Ile Asn
            100                 105                 110

Asn Val Arg Pro Ala Val Asp Phe Thr Leu Asp Lys Ala Ala Glu Ile
        115                 120                 125

Tyr Lys Glu Lys Thr Ile Ala Val Ile Leu Thr Gly Gly Leu Val Asp
    130                 135                 140

Gly Arg Glu Ala Gly Gly Asp Gly Thr Lys Gly Ala Phe Lys Val Lys
145                 150                 155                 160

Phe Tyr Gly Gly Thr Val Ile Ala Glu Asp Lys Glu Thr Ser Val Val
                165                 170                 175

Phe Gly Met Pro Lys Ser Val Ile Glu Glu Gly Tyr Ala Asp Tyr Val
            180                 185                 190

Leu Pro Ala Tyr Lys Ile Pro Glu Lys Leu Ile Glu Leu Val
        195                 200                 205

<210> SEQ ID NO 11
<211> LENGTH: 212
```

<210> TYPE: PRT
<213> ORGANISM: Artificial Sequence
<220> FEATURE:
<223> OTHER INFORMATION: Synthetic Construct

<400> SEQUENCE: 11

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Gly Leu Asp Asn Gly
        35                  40                  45

Ser Tyr Thr Gly Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Gly Asp Arg
            100                 105                 110

Asn Gly Tyr Ser Ala Gly Gly Val Arg Pro Ala Val Asp Phe Thr Leu
        115                 120                 125

Asp Lys Ala Ala Glu Ile Tyr Lys Glu Lys Thr Ile Ala Val Ile Leu
130                 135                 140

Thr Gly Gly Leu Val Asp Gly Arg Glu Ala Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 12
<211> LENGTH: 618
<212> TYPE: DNA
<213> ORGANISM: Artificial Sequence
<220> FEATURE:
<223> OTHER INFORMATION: Synthetic Construct

<400> SEQUENCE: 12
ggttctcaca tggtttctgg taaaatcgtt gttatcggtt cttctaccgg tggtccgcgt      60
tctctggaca tgatcatccc gaacctgccg aaaaacttcc cggctccgat cgttgttgtt     120
cagcacatgc cgccgggttt caccaaatct ctggctcagc gtctggactc tacctctgaa     180
ctgaccgtta agaagctgaa gacggtgaa gaagttaaac cgggtttcgt ttacatcgct     240
ccgggtgact ccacctgggg tctgaaagct cagaacggta agttttctt cttcctggac     300
aaatctggtg gcgaccgtaa cggttactct gctggagggg ttcgtccggc tgttgacttc     360
accctgaca aagctgctga atctacaaa gaaaaacca tcgctgttat cctgaccggt     420
ggactggttg acggtcgtga agctggtggt gacggtacta agggcgcgtt caaagttaaa     480
ttttacggtg gtactgttat cgctgaagac aaagaaaccct ctgttgtttt cggtatgccg     540
aaatctgtta tcgaagaagg ttacgctgac tacgttctgc cggcttacaa aatcccggaa     600
aaactgatcg aactggtt                                                    618

<210> SEQ ID NO 13
<211> LENGTH: 615
<212> TYPE: DNA
<213> ORGANISM: Artificial Sequence
<220> FEATURE:
<223> OTHER INFORMATION: Synthetic Construct

<400> SEQUENCE: 13
ggttctcaca tggtttctgg taaaatcgtt gttatcggtt cttctaccgg tggtccgcgt      60
tctctggaca tgatcatccc gaacctgccg aaaaacttcc cggctccgat cgttgttgtt     120
cagcacggag gtctggacaa cggttcttac accggcggga ccaaatctct ggctcagcgt     180
ctggactcta cctctgaact gaccgttaaa gaagctgaag acggtgaaga agttaaaccg     240
ggtttcgttt acatcgctcc gggtgacttc cacctgggtc tgaaagctca gaacggtaaa     300
gttttcttct cctggacaa atctggtggc gaccgtaacg ttactctgc tggaggggtt       360
cgtccggctg ttgacttcac cctggacaaa gctgctgaaa tctacaaaga aaaaaccatc     420
gctgttatcc tgaccggtat gggtaaagac ggtactaagg gcgcgttcaa gttaaattt     480
tacggtggta ctgttatcgc tgaagacaaa gaaacctctg ttgttttcgg tatgccgaaa    540
tctgttatcg aagaaggtta cgctgactac gttctgccgg cttacaaaat cccggaaaaa    600
ctgatcgaac tggtt                                                       615

<210> SEQ ID NO 14
<211> LENGTH: 618
<212> TYPE: DNA
<213> ORGANISM: Artificial Sequence
<220> FEATURE:
<223> OTHER INFORMATION: Synthetic Construct

<400> SEQUENCE: 14
ggttctcaca tggtttctgg taaaatcgtt gttatcggtt cttctaccgg tggtccgcgt      60
tctctggaca tgatcatccc gaacctgccg aaaaacttcc cggctccgat cgttgttgtt     120
cagcacggag gtctggacaa cggttcttac accggcggga ccaaatctct ggctcagcgt     180
ctggactcta cctctgaact gaccgttaaa gaagctgaag acggtgaaga agttaaaccg     240
ggtttcgttt acatcgctcc gggtgacttc cacctgggtc tgaaagctca gaacggtaaa     300
gttttcttct cctggacaa atctgacaaa atcaacaacg ttcgtccggc tgttgacttc      360
accctggaca aagctgctga aatctacaaa gaaaaaacca tcgctgttat cctgaccggt     420
ggactggttg acggtcgtga agctggtggt gacggtacta agggcgcgtt caaagttaaa    480
ttttacggtg gtactgttat cgctgaagac aaagaaacct ctgttgtttt cggtatgccg     540
aaatctgtta tcgaagaagg ttacgctgac tacgttctgc cggcttacaa atcccggaa     600
aaactgatcg aactggtt                                                   618

<210> SEQ ID NO 15
<211> LENGTH: 636
<212> TYPE: DNA
<213> ORGANISM: Artificial Sequence
<220> FEATURE:
<223> OTHER INFORMATION: Synthetic Construct

<400> SEQUENCE: 15
ggttctcaca tggtttctgg taaaatcgtt gttatcggtt cttctaccgg tggtccgcgt      60
tctctggaca tgatcatccc gaacctgccg aaaaacttcc cggctccgat cgttgttgtt     120

```
cagcacggag gtctggacaa cggttcttac accggcggga ccaaatctct ggctcagcgt    180
ctggactcta cctctgaact gaccgttaaa gaagctgaag acggtgaaga agttaaaccg    240
ggtttcgttt acatcgctcc gggtgacttc cacctgggtc tgaaagctca gaacggtaaa    300
gttttcttct cctggacaa atctggtggc gaccgtaacg gttactctgc tgggggggtt    360
cgtccggctg ttgacttcac cctggacaaa gctgctgaaa tctacaaaga aaaaccatc    420 gctgttatcc tgaccggtgg actggttgac ggtcgtgaag ctggtggtga cggtactaag    480
ggcgcgttca agttaaaatt ttacggtggt actgttatcg ctgaagacaa agaaacctct    540
gttgttttcg gtatgccgaa atctgttatc gaagaaggtt acgctgacta cgttctgccg    600
gcttacaaaa tcccggaaaa actgatcgaa ctggtt                              636
```

<210> SEQ ID NO 16
<211> LENGTH: 83
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (29)..(31)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (32)..(34)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (35)..(37)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (38)..(40)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (44)..(46)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (47)..(49)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (50)..(52)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (53)..(55)
<223> OTHER INFORMATION: represents a codon encoding an amino acid
      residue selected from the group: Ser, Asp, Arg, Ala, Leu, Thr,
      Asn, Trp, Gly, Glu, Val and Tyr

<400> SEQUENCE: 16

```
ggctccgatc gttgttgttc agcacggann nnnnnnnnn ggtnnnnnnn nnnnngggac    60
```
caaatctctg gctcagcgtc tgg 83

<210> SEQ ID NO 17
<211> LENGTH: 95
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (40)..(42)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (43)..(45)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (46)..(48)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (49)..(51)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (55)..(57)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (58)..(60)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (61)..(63)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (64)..(66)
<223> OTHER INFORMATION: represents a codon encoding an amino acid
      residue selected from the group: Ser, Asp, Arg, Ala, Leu, Thr,
      Asn, Trp, Gly, Glu, Val and Tyr

<400> SEQUENCE: 17
cagaacggta agttttctt cttcctggac aaatctggtn nnnnnnnnn nggtnnnnnn    60 nnnnnngggg ttcgtccggc tgttgacttc accct    95

<210> SEQ ID NO 18
<211> LENGTH: 79
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (29)..(31)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base

```
<222> LOCATION: (32)..(34)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (35)..(37)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (41)..(43)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (44)..(46)
<223> OTHER INFORMATION: represents a codon encoding an amino acid
      residue selected from the group: Ser, Asp, Arg, Ala, Leu, Thr,
      Asn, Trp, Gly, Glu, Val and Tyr
<220> FEATURE:
<221> NAME/KEY: modified_base
<222> LOCATION: (47)..(49)
<223> OTHER INFORMATION: represents a codon encoding an amino acid
      residue selected from the group: Ser, Asp, Arg, Ala, Leu, Thr,
      Asn, Trp, Gly, Glu, Val and Tyr

<400> SEQUENCE: 18
aaccatcgct gttatcctga ccggtggann nnnnnnnggt nnnnnnnnng gtggtgacgg      60
tactaagggc gcgttcaaa                                                  79

<210> SEQ ID NO 19
<211> LENGTH: 86
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (32)..(33)
<223> OTHER INFORMATION: a, c, g or t
<220> FEATURE:
<221> NAME/KEY: modified_base
<222> LOCATION: (35)..(36)
<223> OTHER INFORMATION: a, c, g or t
<220> FEATURE:
<221> NAME/KEY: modified_base
<222> LOCATION: (38)..(39)
<223> OTHER INFORMATION: a, c, g or t
<220> FEATURE:
<221> NAME/KEY: modified_base
<222> LOCATION: (44)..(45)
<223> OTHER INFORMATION: a, c, g or t
<220> FEATURE:
<221> NAME/KEY: modified_base
<222> LOCATION: (47)..(48)
<223> OTHER INFORMATION: a, c, g or t
<220> FEATURE:
<221> NAME/KEY: modified_base
<222> LOCATION: (50)..(51)
<223> OTHER INFORMATION: a, c, g or t
<220> FEATURE:
<221> NAME/KEY: modified_base
<222> LOCATION: (53)..(54)
<223> OTHER INFORMATION: a, c, g or t

<400> SEQUENCE: 19
ggctccgatc gttgttgttc agcacggagg annknnknnk ggtnnknnkn nknnkggcgg      60
gaccaaatct ctggctcagc gtctgg                                          86

<210> SEQ ID NO 20
```

```
<211> LENGTH: 98
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (43)..(44)
<223> OTHER INFORMATION: a, c, g or t
<220> FEATURE:
<221> NAME/KEY: modified_base
<222> LOCATION: (46)..(47)
<223> OTHER INFORMATION: a, c, g or t
<220> FEATURE:
<221> NAME/KEY: modified_base
<222> LOCATION: (49)..(50)
<223> OTHER INFORMATION: a, c, g or t
<220> FEATURE:
<221> NAME/KEY: modified_base
<222> LOCATION: (52)..(53)
<223> OTHER INFORMATION: a, c, g or t
<220> FEATURE:
<221> NAME/KEY: modified_base
<222> LOCATION: (58)..(59)
<223> OTHER INFORMATION: a, c, g or t
<220> FEATURE:
<221> NAME/KEY: modified_base
<222> LOCATION: (61)..(62)
<223> OTHER INFORMATION: a, c, g or t
<220> FEATURE:
<221> NAME/KEY: modified_base
<222> LOCATION: (64)..(65)
<223> OTHER INFORMATION: a, c, g or t

<400> SEQUENCE: 20
cagaacggta aagttttctt cttcctggac aaatctggtg gtnnknnknn knnkggtnnk      60
nnknnkggag gggttcgtcc ggctgttgac ttcaccct                             98

<210> SEQ ID NO 21
<211> LENGTH: 43
<212> TYPE: DNA
<213> ORGANISM: Artificial Sequence
<220> FEATURE:
<223> OTHER INFORMATION: Synthetic Construct

<400> SEQUENCE: 21
atagggaatt ctggttctca catggttttct ggtaaaatcg ttg                      43

<210> SEQ ID NO 22
<211> LENGTH: 31
<212> TYPE: DNA
<213> ORGANISM: Artificial Sequence
<220> FEATURE:
<223> OTHER INFORMATION: Synthetic Construct

<400> SEQUENCE: 22
ggttctcaca tggtttctgg taaaatcgtt g                                    31

<210> SEQ ID NO 23
<211> LENGTH: 28
<212> TYPE: DNA
<213> ORGANISM: Artificial Sequence
<220> FEATURE:
<223> OTHER INFORMATION: Synthetic Construct

<400> SEQUENCE: 23
tccgtgctga acaacaacga tcggagcc                                        28

<210> SEQ ID NO 24
<211> LENGTH: 28
```

<212> TYPE: DNA
<213> ORGANISM: Artificial Sequence
<220> FEATURE:
<223> OTHER INFORMATION: Synthetic Construct

<400> SEQUENCE: 24
gggaccaaat ctctggctca gcgtctgg                                28

<210> SEQ ID NO 25
<211> LENGTH: 39
<212> TYPE: DNA
<213> ORGANISM: Artificial Sequence
<220> FEATURE:
<223> OTHER INFORMATION: Synthetic Construct

<400> SEQUENCE: 25
accagatttg tccaggaaga agaaaacttt accgttctg                    39

<210> SEQ ID NO 26
<211> LENGTH: 29
<212> TYPE: DNA
<213> ORGANISM: Artificial Sequence
<220> FEATURE:
<223> OTHER INFORMATION: Synthetic Construct

<400> SEQUENCE: 26
ggggttcgtc cggctgttga cttcaccct                               29

<210> SEQ ID NO 27
<211> LENGTH: 28
<212> TYPE: DNA
<213> ORGANISM: Artificial Sequence
<220> FEATURE:
<223> OTHER INFORMATION: Synthetic Construct

<400> SEQUENCE: 27
tccaccggtc aggataacag cgatggtt                                28

<210> SEQ ID NO 28
<211> LENGTH: 30
<212> TYPE: DNA
<213> ORGANISM: Artificial Sequence
<220> FEATURE:
<223> OTHER INFORMATION: Synthetic Construct

<400> SEQUENCE: 28
ggtggtgacg gtactaaggg cgcgttcaaa                              30

<210> SEQ ID NO 29
<211> LENGTH: 24
<212> TYPE: DNA
<213> ORGANISM: Artificial Sequence
<220> FEATURE:
<223> OTHER INFORMATION: Synthetic Construct

<400> SEQUENCE: 29
aaccagttcg atcagttttt ccgg                                    24

<210> SEQ ID NO 30
<211> LENGTH: 37
<212> TYPE: DNA
<213> ORGANISM: Artificial Sequence
<220> FEATURE:
<223> OTHER INFORMATION: Synthetic Construct

<400> SEQUENCE: 30
atcatggcgc gccaaccagt tcgatcagtt tttccgg                                37

<210> SEQ ID NO 31
<211> LENGTH: 28
<212> TYPE: DNA
<213> ORGANISM: Artificial Sequence
<220> FEATURE:
<223> OTHER INFORMATION: Synthetic Construct

<400> SEQUENCE: 31
ggctccgatc gttgttgttc agcacgga                                          28

<210> SEQ ID NO 32
<211> LENGTH: 28
<212> TYPE: DNA
<213> ORGANISM: Artificial Sequence
<220> FEATURE:
<223> OTHER INFORMATION: Synthetic Construct

<400> SEQUENCE: 32
ccagacgctg agccagagat ttggtccc                                          28

<210> SEQ ID NO 33
<211> LENGTH: 39
<212> TYPE: DNA
<213> ORGANISM: Artificial Sequence
<220> FEATURE:
<223> OTHER INFORMATION: Synthetic Construct

<400> SEQUENCE: 33
cagaacggta agttttctt cttcctggac aaatctggt                               39

<210> SEQ ID NO 34
<211> LENGTH: 29
<212> TYPE: DNA
<213> ORGANISM: Artificial Sequence
<220> FEATURE:
<223> OTHER INFORMATION: Synthetic Construct

<400> SEQUENCE: 34
agggtgaagt caacagccgg acgaacccc                                         29

<210> SEQ ID NO 35
<211> LENGTH: 28
<212> TYPE: DNA
<213> ORGANISM: Artificial Sequence
<220> FEATURE:
<223> OTHER INFORMATION: Synthetic Construct

<400> SEQUENCE: 35
aaccatcgct gttatcctga ccggtgga                                          28

<210> SEQ ID NO 36
<211> LENGTH: 30
<212> TYPE: DNA
<213> ORGANISM: Artificial Sequence
<220> FEATURE:
<223> OTHER INFORMATION: Synthetic Construct

<400> SEQUENCE: 36
tttgaacgcg cccttagtac cgtcaccacc                                        30

<210> SEQ ID NO 37
<211> LENGTH: 83
<212> TYPE: DNA
<213> ORGANISM: Artificial Sequence

```
<220> FEATURE:
<223> OTHER INFORMATION: Synthetic Construct

<400> SEQUENCE: 37
ggctccgatc gttgttgttc agcacggagg tctggacaac ggttcttaca ccggcgggac    60
caaatctctg gctcagcgtc tgg                                            83

<210> SEQ ID NO 38
<211> LENGTH: 95
<212> TYPE: DNA
<213> ORGANISM: Artificial Sequence
<220> FEATURE:
<223> OTHER INFORMATION: Synthetic Construct

<400> SEQUENCE: 38
cagaacggta agttttctt cttcctggac aaatctggtg gcgaccgtaa cggttactct    60
gctggagggg ttcgtccggc tgttgacttc accct                               95

<210> SEQ ID NO 39
<211> LENGTH: 79
<212> TYPE: DNA
<213> ORGANISM: Artificial Sequence
<220> FEATURE:
<223> OTHER INFORMATION: Synthetic Construct

<400> SEQUENCE: 39
aaccatcgct gttatcctga ccggtggact ggttgacggt cgtgaagctg gtggtgacgg    60
tactaagggc gcgttcaaa                                                 79

<210> SEQ ID NO 40
<211> LENGTH: 42
<212> TYPE: PRT
<213> ORGANISM: Artificial Sequence
<220> FEATURE:
<223> OTHER INFORMATION: Synthetic Construct

<400> SEQUENCE: 40

Gly Ser His Met Val Ser Gly Lys Ile Val Val Ile Gly Ser Ser Thr
1               5                  10                  15

Gly Gly Pro Arg Ser Leu Asp Met Ile Ile Pro Asn Leu Pro Lys Asn
            20                  25                  30

Phe Pro Ala Pro Ile Val Val Val Gln His
        35                  40

<210> SEQ ID NO 41
<211> LENGTH: 55
<212> TYPE: PRT
<213> ORGANISM: Artificial Sequence
<220> FEATURE:
<223> OTHER INFORMATION: Synthetic Construct

<400> SEQUENCE: 41

Thr Lys Ser Leu Ala Gln Arg Leu Asp Ser Thr Ser Glu Leu Thr Val
1               5                  10                  15

Lys Glu Ala Glu Asp Gly Glu Glu Val Lys Pro Gly Phe Val Tyr Ile
            20                  25                  30

Ala Pro Gly Asp Phe His Leu Gly Leu Lys Ala Gln Asn Gly Lys Val
        35                  40                  45

Phe Phe Phe Leu Asp Lys Ser
    50                  55
```

```
<210> SEQ ID NO 42
<211> LENGTH: 27
<212> TYPE: PRT
<213> ORGANISM: Artificial Sequence
<220> FEATURE:
<223> OTHER INFORMATION: Synthetic Construct

<400> SEQUENCE: 42

Val Arg Pro Ala Val Asp Phe Thr Leu Asp Lys Ala Ala Glu Ile Tyr
1               5                   10                  15

Lys Glu Lys Thr Ile Ala Val Ile Leu Thr Gly
            20                  25

<210> SEQ ID NO 43
<211> LENGTH: 56
<212> TYPE: PRT
<213> ORGANISM: Artificial Sequence
<220> FEATURE:
<223> OTHER INFORMATION: Synthetic Construct

<400> SEQUENCE: 43

Asp Gly Thr Lys Gly Ala Phe Lys Val Lys Phe Tyr Gly Gly Thr Val
1               5                   10                  15

Ile Ala Glu Asp Lys Glu Thr Ser Val Val Phe Gly Met Pro Lys Ser
            20                  25                  30

Val Ile Glu Glu Gly Tyr Ala Asp Tyr Val Leu Pro Ala Tyr Lys Ile
        35                  40                  45

Pro Glu Lys Leu Ile Glu Leu Val
    50                  55

<210> SEQ ID NO 44
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(5)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (7)..(10)
<223> OTHER INFORMATION: An amino acid selected from the group: Ser,
      Asp, Arg, Ala, Leu, Thr, Asn, Trp, Gly, Glu, Val and Tyr

<400> SEQUENCE: 44

Gly Xaa Xaa Xaa Xaa Gly Xaa Xaa Xaa Xaa Gly
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (7)..(10)
<223> OTHER INFORMATION: Variable amino acid

<400> SEQUENCE: 45

Gly Gly Xaa Xaa Xaa Gly Xaa Xaa Xaa Xaa Gly Gly
```

```
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(6)
<223> OTHER INFORMATION: Variable amino acid
<220> FEATURE:
<221> NAME/KEY: MOD_RES
<222> LOCATION: (8)..(10)
<223> OTHER INFORMATION: Variable amino acid

<400> SEQUENCE: 46

Gly Gly Xaa Xaa Xaa Xaa Gly Xaa Xaa Xaa Gly Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(4)
<223> OTHER INFORMATION: An amino acid selected from the group: Ser,
      Asp, Arg, Ala, Leu, Thr, Asn, Trp, Gly, Glu, Val and Tyr
<220> FEATURE:
<221> NAME/KEY: MOD_RES
<222> LOCATION: (6)..(8)
<223> OTHER INFORMATION: An amino acid selected from the group: Ser,
      Asp, Arg, Ala, Leu, Thr, Asn, Trp, Gly, Glu, Val and Tyr

<400> SEQUENCE: 47

Gly Xaa Xaa Xaa Gly Xaa Xaa Xaa Gly Gly
1               5                   10

<210> SEQ ID NO 48
<211> LENGTH: 191
<212> TYPE: PRT
<213> ORGANISM: Fervidobacterium pennivorans

<400> SEQUENCE: 48

Ile Val Ser Gly Lys Val Val Ile Gly Ser Ser Thr Gly Gly Pro
1               5                   10                  15

Arg Ser Leu Asp Leu Val Ile Pro Pro Leu Pro Lys Asp Phe Pro Ala
                20                  25                  30

Pro Ile Leu Leu Val Gln His Met Pro Pro Gly Phe Thr Lys Ser Leu
            35                  40                  45

Ala Gln Arg Leu Asp Arg Ile Ser Asn Leu Ser Val Lys Glu Ala Glu
        50                  55                  60

Glu Gly Asp Val Leu Lys Pro Gly Trp Val Tyr Val Ala Pro Gly Asp
65                  70                  75                  80

Tyr His Met Gly Ile Lys Tyr Gln Asp Lys Lys Gly Ile Ile Tyr Leu
                85                  90                  95

Asp Lys Asn Thr Glu Lys Ile Asn Asn Val Arg Pro Ala Val Asp Tyr
            100                 105                 110

Thr Leu Asp Lys Val Ala Glu Ile Tyr Lys Glu Asn Thr Ile Ala Val
        115                 120                 125

Ile Leu Thr Gly Met Gly Lys Asp Gly Thr Lys Gly Ala Phe Lys Val
```

```
            130                 135                 140
Lys Phe Phe Lys Gly Val Val Ile Ala Glu Ser Gln Glu Thr Cys Val
145                 150                 155                 160

Val Phe Gly Met Pro Lys Ser Val Ile Glu Glu Gly Tyr Ala Asp Tyr
                165                 170                 175

Val Leu Pro Ala Asp Lys Ile Pro Glu Lys Leu Val Glu Leu Val
            180                 185                 190
```

<210> SEQ ID NO 49
<211> LENGTH: 209
<212> TYPE: PRT
<213> ORGANISM: Artificial Sequence
<220> FEATURE:
<223> OTHER INFORMATION: Synthetic Construct

<400> SEQUENCE: 49

```
Ile Val Ser Gly Lys Val Val Ile Gly Ser Ser Thr Gly Gly Pro
1               5                   10                  15

Arg Ser Leu Asp Leu Val Ile Pro Pro Leu Pro Lys Asp Phe Pro Ala
                20                  25                  30

Pro Ile Leu Leu Val Gln His Gly Gly Leu Asp Asn Gly Ser Tyr Thr
            35                  40                  45

Gly Gly Thr Lys Ser Leu Ala Gln Arg Leu Asp Arg Ile Ser Asn Leu
        50                  55                  60

Ser Val Lys Glu Ala Glu Gly Asp Val Leu Lys Pro Gly Trp Val
65                  70                  75                  80

Tyr Val Ala Pro Gly Asp Tyr His Met Gly Ile Lys Tyr Gln Asp Lys
                85                  90                  95

Lys Gly Ile Ile Tyr Leu Asp Lys Ser Gly Asp Arg Asn Gly Tyr
            100                 105                 110

Ser Ala Gly Gly Val Arg Pro Ala Val Asp Tyr Thr Leu Asp Lys Val
        115                 120                 125

Ala Glu Ile Tyr Lys Glu Asn Thr Ile Ala Val Ile Leu Thr Gly Gly
    130                 135                 140

Leu Val Asp Gly Arg Glu Ala Gly Gly Asp Gly Thr Lys Gly Ala Phe
145                 150                 155                 160

Lys Val Lys Phe Phe Lys Gly Val Val Ile Ala Glu Ser Gln Glu Thr
                165                 170                 175

Ser Val Val Phe Gly Met Pro Lys Ser Val Ile Glu Glu Gly Tyr Ala
            180                 185                 190

Asp Tyr Val Leu Pro Ala Asp Lys Ile Pro Glu Lys Leu Val Glu Leu
        195                 200                 205

Val
```

<210> SEQ ID NO 50
<211> LENGTH: 217
<212> TYPE: PRT
<213> ORGANISM: Artificial Sequence
<220> FEATURE:
<223> OTHER INFORMATION: Synthetic Construct

<400> SEQUENCE: 50

```
Gly Asn Ser Gly Ser Ile Val Ser Gly Lys Val Val Ile Gly Ser
1               5                   10                  15

Ser Thr Gly Gly Pro Arg Ser Leu Asp Leu Val Ile Pro Pro Leu Pro
                20                  25                  30

Lys Asp Phe Pro Ala Pro Ile Leu Leu Val Gln His Gly Gly Leu Asp
```

```
                    35                  40                  45
Asn Gly Ser Tyr Thr Gly Gly Thr Lys Ser Leu Ala Gln Arg Leu Asp
                50                  55                  60

Arg Ile Ser Asn Leu Ser Val Lys Glu Ala Glu Gly Asp Val Leu
65                  70                  75                  80

Lys Pro Gly Trp Val Tyr Val Ala Pro Gly Asp Tyr His Met Gly Ile
                85                  90                  95

Lys Tyr Gln Asp Lys Lys Gly Ile Ile Tyr Leu Asp Lys Ser Gly Gly
                100                 105                 110

Asp Arg Asn Gly Tyr Ser Ala Gly Gly Val Arg Pro Ala Val Asp Tyr
                115                 120                 125

Thr Leu Asp Lys Val Ala Glu Ile Tyr Lys Glu Asn Thr Ile Ala Val
                130                 135                 140

Ile Leu Thr Gly Gly Leu Val Asp Gly Arg Glu Ala Gly Gly Asp Gly
145                 150                 155                 160

Thr Lys Gly Ala Phe Lys Val Lys Phe Phe Lys Gly Val Val Ile Ala
                165                 170                 175

Glu Ser Gln Glu Thr Ser Val Val Phe Gly Met Pro Lys Ser Val Ile
                180                 185                 190

Glu Glu Gly Tyr Ala Asp Tyr Val Leu Pro Ala Asp Lys Ile Pro Glu
                195                 200                 205

Lys Leu Val Glu Leu Val Gly Ala Pro
                210                 215

<210> SEQ ID NO 51
<211> LENGTH: 651
<212> TYPE: DNA
<213> ORGANISM: Artificial Sequence
<220> FEATURE:
<223> OTHER INFORMATION: Synthetic Construct

<400> SEQUENCE: 51
gggaattctg gttctatcgt ttctggtaaa gttgttgtta tcggttcttc taccggtggt      60
ccgcgttctc tggacctggt tatcccgccg ctgccgaaag acttcccggc tccgatcctg     120
ctggttcagc acggtggtct ggacaacggt tcttacaccg gtaccaa atctctggct       180 cagcgtctgg accgtatctc taacctgtct gttaagaag ctgaagaagg tgacgttctg      240
aaaccgggtt gggtttacgt tgctccgggt gactaccaca tgggtatcaa ataccaggac     300
aaaaaaggta tcatctacct ggacaaatct ggtggtgacc gtaacggtta ctctgctggt     360
ggtgttcgtc cggctgttga ctacaccctg gacaaagttg ctgaaatcta caagaaaac     420 accatcgctg ttatcctgac cggtggtctg gttgacggtc gtgaagctgg tggtgacggt     480
accaagggcg cgttcaaagt taaattttc aaaggtgttg ttatcgctga atctcaggaa     540
acctctgttg ttttcggtat gccgaaatct gttatcgaag aaggttacgc tgactacgtt     600
ctgccggctg acaaaatccc ggaaaaactg gttgaactgg ttggcgcgcc a             651

<210> SEQ ID NO 52
<211> LENGTH: 212
<212> TYPE: PRT
<213> ORGANISM: Artificial Sequence
<220> FEATURE:
<223> OTHER INFORMATION: Synthetic Construct

<400> SEQUENCE: 52

Gly Ser His Met Val Ser Gly Lys Ile Val Val Ile Gly Ser Ser Thr
1               5                   10                  15
```

-continued

Gly Gly Pro Arg Ser Leu Asp Met Ile Ile Pro Asn Leu Pro Lys Asn
                20                  25                  30

Phe Pro Ala Pro Ile Val Val Gln His Gly Val Ser Trp Trp Gly
            35                  40                  45

Gly Gly Ser Trp Gly Thr Lys Ser Leu Ala Gln Arg Leu Asp Ser Thr
        50                  55                  60

Ser Glu Leu Thr Val Lys Glu Ala Glu Asp Gly Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Arg Thr Tyr
            100                 105                 110

Tyr Gly Leu Ala Ala Trp Gly Val Arg Pro Ala Val Asp Phe Thr Leu
            115                 120                 125

Asp Lys Ala Ala Glu Ile Tyr Lys Glu Lys Thr Ile Ala Val Ile Leu
130                 135                 140

Thr Gly Gly Asp Ala Glu Gly Trp Tyr Leu Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
            195                 200                 205

Ile Glu Leu Val
        210

<210> SEQ ID NO 53
<211> LENGTH: 212
<212> TYPE: PRT
<213> ORGANISM: Artificial Sequence
<220> FEATURE:
<223> OTHER INFORMATION: Synthetic Construct

<400> SEQUENCE: 53

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
                20                  25                  30

Phe Pro Ala Pro Ile Val Val Gln His Gly Trp Gly Glu Val Gly
            35                  40                  45

Glu Thr Glu Val Gly Thr Lys Ser Leu Ala Gln Arg Leu Asp Ser Thr
        50                  55                  60

Ser Glu Leu Thr Val Lys Glu Ala Glu Asp Gly Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Tyr Ser Tyr
            100                 105                 110

Ala Gly Glu Leu Trp Arg Gly Val Arg Pro Ala Val Asp Phe Thr Leu
            115                 120                 125

Asp Lys Ala Ala Glu Ile Tyr Lys Glu Lys Thr Ile Ala Val Ile Leu
130                 135                 140

Thr Gly Gly Ser Trp Trp Gly Asp Leu Trp Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 54
<211> LENGTH: 212
<212> TYPE: PRT
<213> ORGANISM: Artificial Sequence
<220> FEATURE:
<223> OTHER INFORMATION: Synthetic Construct

<400> SEQUENCE: 54

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Tyr Asp Thr Leu Gly
        35                  40                  45

Trp Trp Gly Asp Gly Thr Lys Ser Leu Ala Gln Arg Leu Asp Ser Thr
    50                  55                  60

Ser Glu Leu Thr Val Lys Glu Ala Glu Asp Gly Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Asp Asp Tyr
            100                 105                 110

Val Gly Tyr Gly Tyr Leu Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Gly Asp Trp Arg Gly Val Trp Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 55
<211> LENGTH: 212
<212> TYPE: PRT
<213> ORGANISM: Artificial Sequence
<220> FEATURE:
<223> OTHER INFORMATION: Synthetic Construct

<400> SEQUENCE: 55

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn

```
            20                  25                  30

Phe Pro Ala Pro Ile Val Val Gln His Gly Ala Gly Trp Trp Gly
        35                  40                  45

Gly Gly Ala Arg Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Arg Val Trp
            100                 105                 110

Ala Gly Ala Glu Ala Trp Gly Val Arg Pro Ala Val Asp Phe Thr Leu
            115                 120                 125

Asp Lys Ala Ala Glu Ile Tyr Lys Glu Lys Thr Ile Ala Val Ile Leu
            130                 135                 140

Thr Gly Gly Ser Glu Thr Gly Ser Trp Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
                180                 185                 190

Gly Tyr Ala Asp Tyr Val Leu Pro Ala Tyr Lys Ile Pro Glu Lys Leu
            195                 200                 205

Ile Glu Leu Val
        210

<210> SEQ ID NO 56
<211> LENGTH: 212
<212> TYPE: PRT
<213> ORGANISM: Artificial Sequence
<220> FEATURE:
<223> OTHER INFORMATION: Synthetic Construct

<400> SEQUENCE: 56

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Asp Ala Trp Trp Gly
        35                  40                  45

Gly Gly Trp Arg Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Asp Ser Tyr
            100                 105                 110

Thr Gly Asn Trp Ala Trp Gly Val Arg Pro Ala Val Asp Phe Thr Leu
            115                 120                 125

Asp Lys Ala Ala Glu Ile Tyr Lys Glu Lys Thr Ile Ala Val Ile Leu
            130                 135                 140

Thr Gly Gly Ala Ser Thr Gly Tyr Asn Gly Gly Asp Gly Thr Lys
145                 150                 155                 160

Gly Ala Phe Lys Val Lys Phe Tyr Gly Gly Thr Val Ile Ala Glu Asp
```

```
                165                 170                 175
Lys Glu Thr Ser Val Val Phe Gly Met Pro Lys Ser Val Ile Glu Glu
            180                 185                 190
Gly Tyr Ala Asp Tyr Val Leu Pro Ala Tyr Lys Ile Pro Glu Lys Leu
        195                 200                 205
Ile Glu Leu Val
    210

<210> SEQ ID NO 57
<211> LENGTH: 212
<212> TYPE: PRT
<213> ORGANISM: Artificial Sequence
<220> FEATURE:
<223> OTHER INFORMATION: Synthetic Construct

<400> SEQUENCE: 57

Gly Ser His Met Val Ser Gly Lys Ile Val Val Ile Gly Ser Ser Thr
1               5                   10                  15
Gly Gly Pro Arg Ser Leu Asp Met Ile Ile Pro Asn Leu Pro Lys Asn
            20                  25                  30
Phe Pro Ala Pro Ile Val Val Gln His Gly Trp Ala Leu Asn Gly
        35                  40                  45
Arg Tyr Thr Leu Gly Thr Lys Ser Leu Ala Gln Arg Leu Asp Ser Thr
    50                  55                  60
Ser Glu Leu Thr Val Lys Glu Ala Glu Asp Gly Glu Val Lys Pro
65                  70                  75                  80
Gly Phe Val Tyr Ile Ala Pro Gly Asp Phe His Leu Gly Leu Lys Ala
                85                  90                  95
Gln Asn Gly Lys Val Phe Phe Phe Leu Asp Lys Ser Gly Ala Arg Asp
            100                 105                 110
Arg Gly Arg Glu Trp Tyr Gly Val Arg Pro Ala Val Asp Phe Thr Leu
        115                 120                 125
Asp Lys Ala Ala Glu Ile Tyr Lys Glu Lys Thr Ile Ala Val Ile Leu
    130                 135                 140
Thr Gly Gly Tyr Trp Glu Gly Asp Tyr Ala Gly Gly Asp Gly Thr Lys
145                 150                 155                 160
Gly Ala Phe Lys Val Lys Phe Tyr Gly Thr Val Ile Ala Glu Asp
                165                 170                 175
Lys Glu Thr Ser Val Val Phe Gly Met Pro Lys Ser Val Ile Glu Glu
            180                 185                 190
Gly Tyr Ala Asp Tyr Val Leu Pro Ala Tyr Lys Ile Pro Glu Lys Leu
        195                 200                 205
Ile Glu Leu Val
    210

<210> SEQ ID NO 58
<211> LENGTH: 212
<212> TYPE: PRT
<213> ORGANISM: Artificial Sequence
<220> FEATURE:
<223> OTHER INFORMATION: Synthetic Construct

<400> SEQUENCE: 58

Gly Ser His Met Val Ser Gly Lys Ile Val Val Ile Gly Ser Ser Thr
1               5                   10                  15
Gly Gly Pro Arg Ser Leu Asp Met Ile Ile Pro Asn Leu Pro Lys Asn
            20                  25                  30
```

```
Phe Pro Ala Pro Ile Val Val Gln His Gly Tyr Ser Gly Thr Gly
            35                  40                  45

Trp Arg Thr Val Gly Thr Lys Ser Leu Ala Gln Arg Leu Asp Ser Thr
 50                  55                  60

Ser Glu Leu Thr Val Lys Glu Ala Glu Asp Gly Glu Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Val Ala Tyr
            100                 105                 110

Ser Gly Trp Tyr Val Tyr Gly Val Arg Pro Ala Val Asp Phe Thr Leu
            115                 120                 125

Asp Lys Ala Ala Glu Ile Tyr Lys Glu Lys Thr Ile Ala Val Ile Leu
130                 135                 140

Thr Gly Gly Trp Ser Leu Gly Val Tyr Leu Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
            195                 200                 205

Ile Glu Leu Val
            210

<210> SEQ ID NO 59
<211> LENGTH: 212
<212> TYPE: PRT
<213> ORGANISM: Artificial Sequence
<220> FEATURE:
<223> OTHER INFORMATION: Synthetic Construct

<400> SEQUENCE: 59

Gly Ser His Met Val Ser Gly Lys Ile Val Ile Gly Ser Ser Thr
 1               5                  10                  15

Gly Gly Pro Arg Ser Leu Asp Met Ile Ile Pro Asn Leu Pro Lys Asn
            20                  25                  30

Phe Pro Ala Pro Ile Val Val Gln His Gly Tyr Asp Tyr Trp Gly
            35                  40                  45

Glu Val Val Gly Thr Lys Ser Leu Ala Gln Arg Leu Asp Ser Thr
 50                  55                  60

Ser Glu Leu Thr Val Lys Glu Ala Glu Asp Gly Glu Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Ser Trp Val
            100                 105                 110

Arg Gly Ser Glu Ala Leu Gly Val Arg Pro Ala Val Asp Phe Thr Leu
            115                 120                 125

Asp Lys Ala Ala Glu Ile Tyr Lys Glu Lys Thr Ile Ala Val Ile Leu
130                 135                 140

Thr Gly Gly Tyr Trp Asp Gly Thr Trp Thr Gly Asp Gly Thr Lys
145                 150                 155                 160

Gly Ala Phe Lys Val Lys Phe Tyr Gly Gly Thr Val Ile Ala Glu Asp
                165                 170                 175
```

```
Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 60
<211> LENGTH: 212
<212> TYPE: PRT
<213> ORGANISM: Artificial Sequence
<220> FEATURE:
<223> OTHER INFORMATION: Synthetic Construct

<400> SEQUENCE: 60

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Trp Glu Glu Ser Gly
        35                  40                  45

Trp Leu Val Glu Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Leu Asn Tyr
            100                 105                 110

Trp Gly Val Trp Asn Trp Gly Val Arg Pro Ala Val Asp Phe Thr Leu
        115                 120                 125

Asp Lys Ala Ala Glu Ile Tyr Lys Glu Lys Thr Ile Ala Val Ile Leu
130                 135                 140

Thr Gly Gly Arg Glu Gly Gly Ala Thr Tyr Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 61
<211> LENGTH: 212
<212> TYPE: PRT
<213> ORGANISM: Artificial Sequence
<220> FEATURE:
<223> OTHER INFORMATION: Synthetic Construct

<400> SEQUENCE: 61

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Ala Ala Ala Trp Gly
        35                  40                  45
```

Asn Val Leu Val Gly Thr Lys Ser Leu Ala Gln Arg Leu Asp Ser Thr
 50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Thr Tyr Trp
                100                 105                 110

Asp Gly Tyr Gly Trp Tyr Gly Val Arg Pro Ala Val Asp Phe Thr Leu
                115                 120                 125

Asp Lys Ala Ala Glu Ile Tyr Lys Glu Lys Thr Ile Ala Val Ile Leu
            130                 135                 140

Thr Gly Gly Glu Trp Asp Gly Trp Gly Leu Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
                180                 185                 190

Gly Tyr Ala Asp Tyr Val Leu Pro Ala Tyr Lys Ile Pro Glu Lys Leu
                195                 200                 205

Ile Glu Leu Val
    210

<210> SEQ ID NO 62
<211> LENGTH: 212
<212> TYPE: PRT
<213> ORGANISM: Artificial Sequence
<220> FEATURE:
<223> OTHER INFORMATION: Synthetic Construct

<400> SEQUENCE: 62

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
                20                  25                  30

Phe Pro Ala Pro Ile Val Val Gln His Gly Tyr Tyr Trp Gly Gly
                35                  40                  45

Ala Val Tyr Val Gly Thr Lys Ser Leu Ala Gln Arg Leu Asp Ser Thr
 50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Arg Val Val
                100                 105                 110

Asp Gly Trp Asp Tyr Asp Gly Val Arg Pro Ala Val Asp Phe Thr Leu
                115                 120                 125

Asp Lys Ala Ala Glu Ile Tyr Lys Glu Lys Thr Ile Ala Val Ile Leu
            130                 135                 140

Thr Gly Gly Tyr Ala Ser Gly Tyr Gly Asp Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
                180                 185                 190

Gly Tyr Ala Asp Tyr Val Leu Pro Ala Tyr Lys Ile Pro Glu Lys Leu
            195                 200                 205

Ile Glu Leu Val
    210

<210> SEQ ID NO 63
<211> LENGTH: 212
<212> TYPE: PRT
<213> ORGANISM: Artificial Sequence
<220> FEATURE:
<223> OTHER INFORMATION: Synthetic Construct

<400> SEQUENCE: 63

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Tyr Leu Arg Leu Gly
            35                  40                  45

Glu Trp Arg Gly Gly Thr Lys Ser Leu Ala Gln Arg Leu Asp Ser Thr
50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Ser Ala Leu
            100                 105                 110

Val Gly Val Ser Ala Asp Gly Val Arg Pro Ala Val Asp Phe Thr Leu
            115                 120                 125

Asp Lys Ala Ala Glu Ile Tyr Lys Glu Lys Thr Ile Ala Val Ile Leu
            130                 135                 140

Thr Gly Gly Arg Trp Tyr Gly Asn Val Glu Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
            195                 200                 205

Ile Glu Leu Val
    210

<210> SEQ ID NO 64
<211> LENGTH: 212
<212> TYPE: PRT
<213> ORGANISM: Artificial Sequence
<220> FEATURE:
<223> OTHER INFORMATION: Synthetic Construct

<400> SEQUENCE: 64

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Trp Ser Trp Trp Gly
            35                  40                  45

Asp Trp Thr Ser Gly Thr Lys Ser Leu Ala Gln Arg Leu Asp Ser Thr

```
                50                  55                  60
Ser Glu Leu Thr Val Lys Glu Ala Asp Gly Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Ser Trp Gly
                100                 105                 110

Tyr Gly Asp Tyr Trp Ala Gly Val Arg Pro Ala Val Asp Phe Thr Leu
                115                 120                 125

Asp Lys Ala Ala Glu Ile Tyr Lys Glu Lys Thr Ile Ala Val Ile Leu
                130                 135                 140

Thr Gly Gly Thr Trp Asp Gly Trp Val Thr Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
                180                 185                 190

Gly Tyr Ala Asp Tyr Val Leu Pro Ala Tyr Lys Ile Pro Glu Lys Leu
                195                 200                 205

Ile Glu Leu Val
        210

<210> SEQ ID NO 65
<211> LENGTH: 212
<212> TYPE: PRT
<213> ORGANISM: Artificial Sequence
<220> FEATURE:
<223> OTHER INFORMATION: Synthetic Construct

<400> SEQUENCE: 65

Gly Ser His Met Val Ser Gly Lys Ile Val Val Ile Gly Ser Ser Thr
 1               5                  10                  15

Gly Gly Pro Arg Ser Leu Asp Met Ile Ile Pro Asn Leu Pro Lys Asn
                 20                  25                  30

Phe Pro Ala Pro Ile Val Val Val Gln His Gly Tyr Tyr Trp Gly Ser
                 35                  40                  45

Trp Gly Tyr Glu Gly Thr Lys Ser Leu Ala Gln Arg Leu Asp Ser Thr
 50                  55                  60

Ser Glu Leu Thr Val Lys Glu Ala Asp Gly Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Arg Val Val
                100                 105                 110

Asp Gly Trp Asp Tyr Asp Gly Val Arg Pro Ala Val Asp Phe Thr Leu
                115                 120                 125

Asp Lys Ala Ala Glu Ile Tyr Lys Glu Lys Thr Ile Ala Val Ile Leu
                130                 135                 140

Thr Gly Gly Trp Asp Thr Gly Ser Glu Leu Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
                180                 185                 190

Gly Tyr Ala Asp Tyr Val Leu Pro Ala Tyr Lys Ile Pro Glu Lys Leu
```

```
                195                 200                 205

Ile Glu Leu Val
    210

<210> SEQ ID NO 66
<211> LENGTH: 212
<212> TYPE: PRT
<213> ORGANISM: Artificial Sequence
<220> FEATURE:
<223> OTHER INFORMATION: Synthetic Construct

<400> SEQUENCE: 66

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Ser Trp Val Asp Gly
        35                  40                  45

Ser Trp Thr Trp Gly Thr Lys Ser Leu Ala Gln Arg Leu Asp Ser Thr
    50                  55                  60

Ser Glu Leu Thr Val Lys Glu Ala Asp Gly Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Trp Trp Asn
            100                 105                 110

Gly Gly Tyr Trp Val Thr Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Gly Val Asn Leu Gly Leu Tyr Asn Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 67
<211> LENGTH: 211
<212> TYPE: PRT
<213> ORGANISM: Artificial Sequence
<220> FEATURE:
<223> OTHER INFORMATION: Synthetic Construct

<400> SEQUENCE: 67

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Asn Tyr Ala Thr Gly
        35                  40                  45

Trp Thr Thr Ser Gly Thr Lys Ser Leu Ala Gln Arg Leu Asp Ser Thr
    50                  55                  60
```

```
Ser Glu Leu Thr Val Lys Glu Ala Glu Asp Gly Glu Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Leu Asp Trp
            100                 105                 110

Gly Trp Trp Ala Trp Gly Val Arg Pro Ala Val Asp Phe Thr Leu Asp
            115                 120                 125

Lys Ala Ala Glu Ile Tyr Lys Glu Lys Thr Ile Ala Val Ile Leu Thr
            130                 135                 140

Gly Gly Trp Glu Ser Gly Asp Tyr Thr Gly Gly Asp Gly Thr Lys Gly
145                 150                 155                 160

Ala Phe Lys Val Lys Phe Tyr Gly Gly Thr Val Ile Ala Glu Asp Lys
                165                 170                 175

Glu Thr Ser Val Val Phe Gly Met Pro Lys Ser Val Ile Glu Glu Gly
                180                 185                 190

Tyr Ala Asp Tyr Val Leu Pro Ala Tyr Lys Ile Pro Glu Lys Leu Ile
            195                 200                 205

Glu Leu Val
    210

<210> SEQ ID NO 68
<211> LENGTH: 212
<212> TYPE: PRT
<213> ORGANISM: Artificial Sequence
<220> FEATURE:
<223> OTHER INFORMATION: Synthetic Construct

<400> SEQUENCE: 68

Gly Ser His Met Val Ser Gly Lys Ile Val Ile Gly Ser Ser Thr
 1               5                  10                  15

Gly Gly Pro Arg Ser Leu Asp Met Ile Ile Pro Asn Leu Pro Lys Asn
                 20                  25                  30

Phe Pro Ala Pro Ile Val Val Gln His Gly Trp Trp Ser Trp Gly
             35                  40                  45

Trp Arg Gly Trp Gly Thr Lys Ser Leu Ala Gln Arg Leu Asp Ser Thr
 50                  55                  60

Ser Glu Leu Thr Val Lys Glu Ala Glu Asp Gly Glu Glu Val Lys Pro
 65                  70                  75                  80

Gly Phe Val Tyr Ile Ala Pro Gly Asp Phe His Leu Gly Leu Lys Ala
                 85                  90                  95

Gln Asn Gly Lys Val Phe Phe Leu Asp Lys Ser Gly Arg Thr Asp
            100                 105                 110

Trp Gly Tyr Glu Tyr Trp Gly Val Arg Pro Ala Val Asp Phe Thr Leu
            115                 120                 125

Asp Lys Ala Ala Glu Ile Tyr Lys Glu Lys Thr Ile Ala Val Ile Leu
            130                 135                 140

Thr Gly Gly Ala Trp Glu Gly Ser Ala Tyr Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
            195                 200                 205
```

Ile Glu Leu Val
    210

<210> SEQ ID NO 69
<211> LENGTH: 212
<212> TYPE: PRT
<213> ORGANISM: Artificial Sequence
<220> FEATURE:
<223> OTHER INFORMATION: Synthetic Construct

<400> SEQUENCE: 69

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Val Gln His Gly His Asp Trp Ser Gly
        35                  40                  45

Ser Ser Gly Trp Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Phe Leu Asp Lys Ser Gly Trp Val Ser
            100                 105                 110

Trp Gly Trp Thr Asn Asn Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Gly Arg Tyr Glu Gly Val Leu Leu Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 70
<211> LENGTH: 212
<212> TYPE: PRT
<213> ORGANISM: Artificial Sequence
<220> FEATURE:
<223> OTHER INFORMATION: Synthetic Construct

<400> SEQUENCE: 70

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Val Gln His Gly Trp Tyr Trp Gly Gly
        35                  40                  45

Val Arg Gly Glu Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

-continued

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Asp Trp Tyr
            100                 105                 110

Trp Gly Trp Gly Asp Trp Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Gly Glu Asp Tyr Gly Ala Ala Asp Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 71
<211> LENGTH: 212
<212> TYPE: PRT
<213> ORGANISM: Artificial Sequence
<220> FEATURE:
<223> OTHER INFORMATION: Synthetic Construct

<400> SEQUENCE: 71

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Trp Glu Arg Val Gly
        35                  40                  45

Leu Arg Leu Ser Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Phe Leu Asp Lys Ser Gly Ala Trp Ala
            100                 105                 110

Trp Gly Asn Val Trp Trp Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Gly Ala Trp Leu Gly Glu Thr Val Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

```
<210> SEQ ID NO 72
<211> LENGTH: 212
<212> TYPE: PRT
<213> ORGANISM: Artificial Sequence
<220> FEATURE:
<223> OTHER INFORMATION: Synthetic Construct

<400> SEQUENCE: 72

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Val Gln His Gly Glu Val Leu Asp Gly
        35                  40                  45

Ala Tyr Glu Glu Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Cys Arg Tyr
            100                 105                 110

Glu Gly Tyr Gly Thr Leu Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Gly Tyr Ser Glu Gly Asn Tyr Ala Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 73
<211> LENGTH: 212
<212> TYPE: PRT
<213> ORGANISM: Artificial Sequence
<220> FEATURE:
<223> OTHER INFORMATION: Synthetic Construct

<400> SEQUENCE: 73

Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Val Gln His Gly Ala Gly Trp Tyr Gly
        35                  40                  45

Gly Gly Ala Ala Gly Thr Lys Ser Leu Ala Gln Arg Leu Asp Ser Thr
    50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
```

Gln Asn Gly Lys Val Phe Phe Leu Asp Lys Ser Gly Asn Ser Val
                85                  90                  95

Ala Gly Arg Trp Tyr Trp Gly Val Arg Pro Ala Val Asp Phe Thr Leu
        100                 105                 110

Asp Lys Ala Ala Glu Ile Tyr Lys Glu Lys Thr Ile Ala Val Ile Leu
        130                 135                 140

Thr Gly Gly Glu Val Glu Gly Tyr Asp Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
            195                 200                 205

Ile Glu Leu Val
    210

<210> SEQ ID NO 74
<211> LENGTH: 212
<212> TYPE: PRT
<213> ORGANISM: Artificial Sequence
<220> FEATURE:
<223> OTHER INFORMATION: Synthetic Construct

<400> SEQUENCE: 74

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Glu Gly Trp Tyr Gly
            35                  40                  45

Gly Gly Ala Val Gly Thr Lys Ser Leu Ala Gln Arg Leu Asp Ser Thr
        50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Arg Gly Leu
        100                 105                 110

Arg Gly Gly Trp Ser Trp Gly Val Arg Pro Ala Val Asp Phe Thr Leu
        115                 120                 125

Asp Lys Ala Ala Glu Ile Tyr Lys Glu Lys Thr Ile Ala Val Ile Leu
        130                 135                 140

Thr Gly Gly Ala Ala Thr Gly Ser Ser Asn Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
            195                 200                 205

Ile Glu Leu Val
    210

```
<210> SEQ ID NO 75
<211> LENGTH: 212
<212> TYPE: PRT
<213> ORGANISM: Artificial Sequence
<220> FEATURE:
<223> OTHER INFORMATION: Synthetic Construct

<400> SEQUENCE: 75
```

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Asp Gly Trp Tyr Gly
        35                  40                  45

Gly Gly Ala Val Gly Thr Lys Ser Leu Ala Gln Arg Leu Asp Ser Thr
50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Gly Ser Tyr
            100                 105                 110

Thr Gly Glu Trp Thr Trp Gly Val Arg Pro Ala Val Asp Phe Thr Leu
        115                 120                 125

Asp Lys Ala Ala Glu Ile Tyr Lys Glu Lys Thr Ile Ala Val Ile Leu
130                 135                 140

Thr Gly Gly Ala Arg Tyr Gly Asp Leu Arg Gly Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

```
<210> SEQ ID NO 76
<211> LENGTH: 212
<212> TYPE: PRT
<213> ORGANISM: Artificial Sequence
<220> FEATURE:
<223> OTHER INFORMATION: Synthetic Construct

<400> SEQUENCE: 76
```

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Val Ser Trp Trp Gly
        35                  40                  45

Gly Gly Ser Trp Gly Thr Lys Ser Leu Ala Gln Arg Leu Asp Ser Thr
50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

```
Gln Asn Gly Lys Val Phe Phe Leu Asp Lys Ser Gly Arg Thr Tyr
            100                 105                 110

Tyr Gly Leu Ala Ala Trp Gly Val Arg Pro Ala Val Asp Phe Thr Leu
        115                 120                 125

Asp Lys Ala Ala Glu Ile Tyr Lys Glu Lys Thr Ile Ala Val Ile Leu
    130                 135                 140

Thr Gly Gly Asp Ala Glu Gly Trp Tyr Leu Gly Asp Gly Thr Lys
145                 150                 155                 160

Gly Ala Phe Lys Val Lys Phe Tyr Gly Gly Thr Val Ile Ala Glu Asp
                165                 170                 175

Lys Glu Thr Ser Val Val Phe Gly Met Pro Lys Ser Val Ile Glu Glu
            180                 185                 190

Gly Tyr Ala Asp Tyr Val Leu Pro Ala Tyr Lys Ile Pro Glu Lys Leu
        195                 200                 205

Ile Glu Leu Val
    210

<210> SEQ ID NO 77
<211> LENGTH: 213
<212> TYPE: PRT
<213> ORGANISM: Artificial Sequence
<220> FEATURE:
<223> OTHER INFORMATION: Synthetic Construct

<400> SEQUENCE: 77

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Gln His Gly Gly His Pro Gln Gly
        35                  40                  45

Asp Asp Leu Arg Gly Gly Thr Lys Ser Leu Ala Gln Arg Leu Asp Ser
    50                  55                  60

Thr Ser Glu Leu Thr Val Lys Glu Ala Glu Asp Gly Glu Glu Val Lys
65                  70                  75                  80

Pro Gly Phe Val Tyr Ile Ala Pro Gly Asp Phe His Leu Gly Leu Lys
                85                  90                  95

Ala Gln Asn Gly Lys Val Phe Phe Leu Asp Lys Ser Gly Tyr Trp
            100                 105                 110

Tyr Gly Gly Trp Ser Trp Tyr Gly Val Arg Pro Ala Val Asp Phe Thr
        115                 120                 125

Leu Asp Lys Ala Ala Glu Ile Tyr Lys Glu Lys Thr Ile Ala Val Ile
    130                 135                 140

Leu Thr Gly Gly Trp Tyr Ser Gly Ala Gly Leu Gly Gly Asp Gly Thr
145                 150                 155                 160

Lys Gly Ala Phe Lys Val Lys Phe Tyr Gly Gly Thr Val Ile Ala Glu
                165                 170                 175

Asp Lys Glu Thr Ser Val Val Phe Gly Met Pro Lys Ser Val Ile Glu
            180                 185                 190

Glu Gly Tyr Ala Asp Tyr Val Leu Pro Ala Tyr Lys Ile Pro Glu Lys
        195                 200                 205

Leu Ile Glu Leu Val
    210

<210> SEQ ID NO 78
<211> LENGTH: 214
```

<212> TYPE: PRT
<213> ORGANISM: Artificial Sequence
<220> FEATURE:
<223> OTHER INFORMATION: Synthetic Construct

<400> SEQUENCE: 78

```
Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Val Gln His Gly Gly His Pro Gln Gly
        35                  40                  45

Asp Ile Asn Arg Gly Gly Thr Lys Ser Leu Ala Gln Arg Leu Asp Ser
50                  55                  60

Thr Ser Glu Leu Thr Val Lys Glu Ala Glu Asp Gly Glu Glu Val Lys
65                  70                  75                  80

Pro Gly Phe Val Tyr Ile Ala Pro Gly Asp Phe His Leu Gly Leu Lys
                85                  90                  95

Ala Gln Asn Gly Lys Val Phe Phe Leu Asp Lys Ser Gly Gly Ala
            100                 105                 110

Met Asn Tyr Gly His Ala Trp Gly Gly Val Arg Pro Ala Val Asp Phe
            115                 120                 125

Thr Leu Asp Lys Ala Ala Glu Ile Tyr Lys Glu Lys Thr Ile Ala Val
130                 135                 140

Ile Leu Thr Gly Gly Asn Val Glu Gly Val Trp Glu Gly Gly Asp Gly
145                 150                 155                 160

Thr Lys Gly Ala Phe Lys Val Lys Phe Tyr Gly Gly Thr Val Ile Ala
                165                 170                 175

Glu Asp Lys Glu Thr Ser Val Val Phe Gly Met Pro Lys Ser Val Ile
            180                 185                 190

Glu Glu Gly Tyr Ala Asp Tyr Val Leu Pro Ala Tyr Lys Ile Pro Glu
            195                 200                 205

Lys Leu Ile Glu Leu Val
    210
```

<210> SEQ ID NO 79
<211> LENGTH: 212
<212> TYPE: PRT
<213> ORGANISM: Artificial Sequence
<220> FEATURE:
<223> OTHER INFORMATION: Synthetic Construct

<400> SEQUENCE: 79

```
Gly Ser His Met Val Ser Gly Lys Ile Val Val Ile Gly Ser Ser Thr
1               5                   10                  15

Gly Gly Pro Arg Ser Leu Asp Met Ile Ile Pro Asn Leu Pro Lys Asn
            20                  25                  30

Phe Pro Ala Pro Ile Val Val Val Gln His Gly Glu Trp Glu Ser Gly
        35                  40                  45

Asn Asp Glu Asn Gly Thr Lys Ser Leu Ala Gln Arg Leu Asp Ser Thr
50                  55                  60

Ser Glu Leu Thr Val Lys Glu Ala Glu Asp Gly Glu Glu Val Lys Pro
65                  70                  75                  80

Gly Phe Val Tyr Ile Ala Pro Gly Asp Phe His Leu Gly Leu Lys Ala
                85                  90                  95

Gln Asn Gly Lys Val Phe Phe Leu Asp Lys Ser Gly Tyr Trp Trp
            100                 105                 110
```

Glu Gly Thr Asn Arg Trp Gly Val Arg Pro Ala Val Asp Phe Thr Leu
            115                 120                 125

Asp Lys Ala Ala Glu Ile Tyr Lys Glu Lys Thr Ile Ala Val Ile Leu
    130                 135                 140

Thr Gly Gly Trp Tyr Gly Tyr Glu Trp Gly Asp Gly Thr Lys
145                 150                 155                 160

Gly Ala Phe Lys Val Lys Phe Tyr Gly Thr Val Ile Ala Glu Asp
                165                 170                 175

Lys Glu Thr Ser Val Val Phe Gly Met Pro Lys Ser Val Ile Glu Glu
                180                 185                 190

Gly Tyr Ala Asp Tyr Val Leu Pro Ala Tyr Lys Ile Pro Glu Lys Leu
                195                 200                 205

Ile Glu Leu Val
    210

<210> SEQ ID NO 80
<211> LENGTH: 193
<212> TYPE: PRT
<213> ORGANISM: Artificial Sequence
<220> FEATURE:
<223> OTHER INFORMATION: Synthetic Construct

<400> SEQUENCE: 80

Gly Ser His Met Val Ser Gly Lys Ile Val Ile Gly Ser Ser Thr
1               5                   10                  15

Gly Gly Pro Arg Ser Leu Asp Met Ile Ile Pro Asn Leu Pro Lys Asn
                20                  25                  30

Phe Pro Ala Pro Ile Val Val Gln His Met Pro Pro Gly Phe Thr
            35                  40                  45

Lys Ser Leu Ala Met Arg Leu Asp Ser Thr Ser Glu Leu Thr Val Lys
50                  55                  60

Glu Ala Glu Asp Gly Glu Val Lys Pro Gly Phe Val Tyr Ile Ala
65                  70                  75                  80

Pro Gly Asp Phe His Leu Gly Leu Lys Ala Gln Asn Gly Lys Val Phe
                85                  90                  95

Phe Phe Leu Asp Lys Ser Asp Lys Ile Asn Asn Val Arg Pro Ala Val
                100                 105                 110

Asp Phe Thr Leu Asp Lys Ala Ala Glu Ile Tyr Lys Ser Lys Thr Ile
            115                 120                 125

Ala Val Ile Leu Thr Gly Met Gly Lys Asp Gly Thr Lys Gly Ala Phe
    130                 135                 140

Lys Val Lys Phe Tyr Gly Gly Thr Val Ile Ala Glu Asp Lys Glu Thr
145                 150                 155                 160

Cys Val Val Phe Gly Met Pro Lys Ser Val Ile Glu Glu Gly Tyr Ala
                165                 170                 175

Asp Tyr Val Leu Pro Ala Tyr Lys Ile Pro Glu Lys Leu Ile Glu Leu
                180                 185                 190

Val

<210> SEQ ID NO 81
<211> LENGTH: 126
<212> TYPE: DNA
<213> ORGANISM: Artificial Sequence
<220> FEATURE:
<223> OTHER INFORMATION: Synthetic Construct

<400> SEQUENCE: 81

```
ggttctcaca tggtttctgg taaaatcgtt gttatcggtt cttctaccgg tggtccgcgt    60
tctctggaca tgatcatccc gaacctgccg aaaaacttcc cggctccgat cgttgttgtt   120
cagcac                                                              126
```

<210> SEQ ID NO 82
<211> LENGTH: 165
<212> TYPE: DNA
<213> ORGANISM: Artificial Sequence
<220> FEATURE:
<223> OTHER INFORMATION: Synthetic Construct

<400> SEQUENCE: 82

```
accaaatctc tggctcagcg tctggactct acctctgaac tgaccgttaa agaagctgaa    60
gacggtgaag aagttaaacc gggtttcgtt tacatcgctc cgggtgactt ccacctgggt   120
ctgaaagctc agaacggtaa agttttcttc ttcctggaca aatct                   165
```

<210> SEQ ID NO 83
<211> LENGTH: 81
<212> TYPE: DNA
<213> ORGANISM: Artificial Sequence
<220> FEATURE:
<223> OTHER INFORMATION: Synthetic Construct

<400> SEQUENCE: 83

```
gttcgtccgg ctgttgactt caccctggac aaagctgctg aaatctacaa agaaaaaacc    60
atcgctgtta tcctgaccgg t                                              81
```

<210> SEQ ID NO 84
<211> LENGTH: 168
<212> TYPE: DNA
<213> ORGANISM: Artificial Sequence
<220> FEATURE:
<223> OTHER INFORMATION: Synthetic Construct

<400> SEQUENCE: 84

```
gacggtacta agggcgcgtt caaagttaaa ttttacggtg gtactgttat cgctgaagac    60
aaagaaacct ctgttgtttt cggtatgccg aaatctgtta tcgaagaagg ttacgctgac   120
tacgttctgc cggcttacaa aatcccggaa aaactgatcg aactggtt               168
```

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct

<400> SEQUENCE: 85

Gly Gly Leu Asp Asn Gly Ser Tyr Thr Gly Gly
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct

<400> SEQUENCE: 86

Gly Gly Asp Arg Asn Gly Tyr Ser Ala Gly Gly
1               5                   10

```
<210> SEQ ID NO 87
<211> LENGTH: 10
<212> TYPE: PRT
<213> ORGANISM: Artificial Sequence
<220> FEATURE:
<223> OTHER INFORMATION: Synthetic Construct

<400> SEQUENCE: 87

Gly Leu Val Asp Gly Arg Glu Ala Gly Gly
1               5                   10
```